United States Patent
Baker et al.

(10) Patent No.: US 10,988,514 B2
(45) Date of Patent: Apr. 27, 2021

(54) POLYPEPTDES CAPABLE OF FORMING HOMO-OLIGOMERS WITH MODULAR HYDROGEN BOND NETWORK-MEDIATED SPECIFICITY AND THEIR DESIGN

(71) Applicant: UNIVERSITY OF WASHINGTON, Seattle, WA (US)

(72) Inventors: David Baker, Seattle, WA (US); Scott Boyken, Seattle, WA (US); Zibo Chen, Seattle, WA (US); Chunfu Xu, Seattle, WA (US); Sherry Bermeo, Seattle, WA (US); Robert Langan, Seattle, WA (US)

(73) Assignee: University of Washington, Seattle, WA (US)

( * ) Notice: Subject to any disclaimer, the term of this patent is extended or adjusted under 35 U.S.C. 154(b) by 20 days.

(21) Appl. No.: 16/088,686

(22) PCT Filed: Mar. 31, 2017

(86) PCT No.: PCT/US2017/025532
§ 371 (c)(1),
(2) Date: Sep. 26, 2018

(87) PCT Pub. No.: WO2017/173356
PCT Pub. Date: Oct. 5, 2017

(65) Prior Publication Data
US 2019/0112345 A1    Apr. 18, 2019

Related U.S. Application Data

(60) Provisional application No. 62/317,190, filed on Apr. 1, 2016.

(51) Int. Cl.
| | | |
|---|---|---|
| C07K 14/00 | (2006.01) | |
| C07K 14/435 | (2006.01) | |
| C07K 1/113 | (2006.01) | |
| G16B 15/20 | (2019.01) | |
| C07K 2/00 | (2006.01) | |
| C07K 16/18 | (2006.01) | |

(52) U.S. Cl.
CPC ............ *C07K 14/435* (2013.01); *C07K 1/113* (2013.01); *C07K 2/00* (2013.01); *C07K 14/001* (2013.01); *C07K 16/18* (2013.01); *G16B 15/20* (2019.02)

(58) Field of Classification Search
None
See application file for complete search history.

(56) References Cited

U.S. PATENT DOCUMENTS

| | | | |
|---|---|---|---|
| 6,188,965 B1 | 2/2001 | Mayo et al. | |
| 7,574,306 B1 | 8/2009 | Baker et al. | |
| 2004/0031072 A1* | 2/2004 | La Rosa | C07H 21/04 800/278 |
| 2005/0202510 A1 | 9/2005 | Brandman et al. | |
| 2011/0224404 A1 | 9/2011 | Blaber et al. | |
| 2013/0225488 A1 | 8/2013 | Bahekar et al. | |
| 2015/0356240 A1 | 12/2015 | Baker et al. | |

FOREIGN PATENT DOCUMENTS

| | | | |
|---|---|---|---|
| WO | WO 2010/066740 | | 6/2010 |
| WO | WO 2014/124301 | * | 8/2014 |

OTHER PUBLICATIONS

Acharya et al., Stability of 100 homo and heterotypic coiled-coil a-a' pairs for ten amino acids (A, L, I, V, N, K, S, T, E, and R). Biochemistry. 45, 11324-11332 (2006).
Acharya et al., A heterodimerizing leucine zipper coiled coil system for examining the specificity of a position interactions: amino acids I, V, L, N, A, and K. Biochemistry. 41, 14122-14131 (2002).
Adams et al., PHENIX: a comprehensive Python-based system for macromolecular structure solution. Acta Crystallogr D Biol Crystallogr. 66, 213-221 (2010).
Afonine et al., Joint X-ray and neutron refinement with phenix.refine. Acta Crystallogr D Biol Crystallogr. 66, 1153-1163 (2010).
Akey et al., Buried polar residues in coiled-coil interfaces. Biochemistry. 40, 6352-6360 (2001).
Baker et al., Local and macroscopic electrostatic interactions in single α-helices. Nat Chem Biol. 11, 221-228 (2015).
Bartel et al., A protein linkage map of *Escherichia coli* bacteriophage T7. Nat Genet. 12, 72-77 (1996).
Betz et al., De novo design of native proteins: characterization of proteins intended to fold into antiparallel, rop-like, four-helix bundles. Biochemistry. 36, 2450-2458 (1997).
Boyken et al. "Supplementary Materials for: De novo design of protein homo-oligomers with modular hydrogen-bond network-mediated specificity", Science, vol. 352 Issue 6286, May 6, 2016, pp. 680-687.
Boyle & Woolfson, De novo designed peptides for biological applications. Chem Soc Rev. 40, 4295-4306 (2011).

(Continued)

*Primary Examiner* — Ronald T Niebauer
(74) *Attorney, Agent, or Firm* — McDonnell Boehnen Hulbert & Berghoff LLP

(57) ABSTRACT

Methods and apparatus for identifying and screening hydrogen bond networks are provided. A computing device can determine a search space for hydrogen bond networks related to one or more molecules, where the search space can include a plurality of energy terms related to a plurality of residues related to the hydrogen bond networks. The computing device can search the search space to identify one or more hydrogen bond networks based on the plurality of energy terms. The computing device can screen the identified hydrogen bond networks to identity one or more screened hydrogen bond networks based on scores for the identified hydrogen bond networks. An output can be generated that is related to the one or more screened hydrogen bond networks. Also provided are polypeptides that can form homo-oligomers with modular hydrogen bond network-mediated specificity.

21 Claims, 8 Drawing Sheets

Specification includes a Sequence Listing.

(56) References Cited

OTHER PUBLICATIONS

Burkhard et al., Coiled coils: a highly versatile protein folding motif. Trends Cell Biol. 11, 82-88 (2001).
Chakrabarti et al., Sequence optimization and designability of enzyme active sites. 12035-12040 (2005). Proc Natl Acad Sci USA. 102, 12035-12040 (2005).
Chen et al., DNA nanotechnology from the test tube to the cell. Nat Nanotechnol. 10, 748-760 (2015).
Chien et al., The two-hybrid system: a method to identify and clone genes for proteins that interact with a protein of interest. Proc Natl Acad Sci USA. 88, 9578-9582 (1991).
Crick, The packing of [alpha]-helices: simple coiled-coils. Acta Cryst (1953). Q6, 689-697. 6, 1-9 (1953).
Dahiyat & Mayo, Protein design automation. Protein Sci. 5, 895-903 (1996).
Dahiyat, De Novo Protein Design: Fully Automated Sequence Selection, Science, vol. 278: 82-87 (Oct. 1997).
Davis et al., MolProbity: all-atom contacts and structure validation for proteins and nucleic acids. Nucleic Acids Res. 35, W375-83 (2007).
Dimaio et al., Modeling symmetric macromolecular structures in Rosetta3. PLoS One 6, e20450 (2011).
Dyer et al., High-throughput SAXS for the characterization of biomolecules in solution: a practical approach. Methods Mol Biol. 1091, 245-258 (2014).
Eckert et al., Crystal structure of GCN4-pIQI, a trimeric coiled coil with buried polar residues. J Mol Biol. 284, 859-865 (1998).
Emsley et al., Coot: model-building tools for molecular graphics. Acta Crystallogr D Biol Crystallogr. 60, 2126-2132 (2004).
Eng et al., An approach to correlate tandem mass spectral data of peptides with amino acid sequences in a protein database. Journal of the American Society for Mass Spectrometry. 5, 976-989 (1994).
Fields & Song, A novel genetic system to detect protein-protein interactions. Nature. 340, 245-246 (1989).
Fleishman et al., Computational design of proteins targeting the conserved stem region of influenza hemagglutinin. Science. 332, 816-821 (2011).
Fleishman et al., RosettaScripts: A Scripting Language Interface to the Rosetta Macromolecular Modeling Suite. PLoS ONE. 6, e20161 (2011).
Fletcher et al., A basis set of de novo coiled-coil peptide oligomers for rational protein design and synthetic biology. ACS Synth Biol. 1, 240-250 (2012).
Fleming & Rose, Do all backbone polar groups in proteins form hydrogen bonds? Protein Sci. 14, 1911-1917 (2005).
Go et al. "Structure and dynamics of de novo proteins from a designed superfamily of 4-helix bundles" Protein Science, 17, 2008, 821-832.
Gonzalez et al., Buried polar residues and structural specificity in the GCN4 leucine zipper. Nat. Struct. Biol. 3, 1011-1018 (1996).
Gradišar & Jerala, De novo design of orthogonal peptide pairs forming parallel coiled-coil heterodimers. J. Pept. Sci. 17, 100-106 (2011).
Gibson et al., Enzymatic assembly of DNA molecules up to several hundred kilobases. Nat Methods. 6, 343-345 (2009).
Gish, States, Identification of protein coding regions by database similarity search. Nat Genet. 3, 266-272 (1993).
Grigoryan et al., Design of protein-interaction specificity gives selective bZIP-binding peptides. Nature. 458, 859-864 (2009).
Grigoryan & Keating, Structural specificity in coiled-coil interactions. Curr Opin Struct Biol. 18, 477-483 (2008).
Grigoryan & DeGrado, Probing designability via a generalized model of helical bundle geometry. J Mol Biol. 405, 1079-1100 (2011).
Gruber & Lupas, Historical review: another 50th anniversary—new periodicities in coiled coils. Trends Biochem Sci. 28, 679-685 (2003).
Hallen et al. "OSPREY 3.0: Open-source protein redesign for you, with powerful new features" Journal of Computational Chemistry, 39, 2008, 2494-2507.
Harbury et al., A switch between two-, three-, and four-stranded coiled coils in GCN4 leucine zipper mutants. Science. 262, 1401-1407 (1993).
Harbury et al., High-resolution protein design with backbone freedom. Science. 282, 1462-1467 (1998).
Huang et al., High thermodynamic stability of parametrically designed helical bundles. Science. 346, 481-485 (2014).
Huang et al., A de novo designed protein protein interface. Protein Sci. 16, 2770-2774 (2007).
Huang et al., RosettaRemodel: A Generalized Framework for Flexible Backbone Protein Design. PLoS ONE. 6, e24109 (2011).
Jacak et al., Computational protein design with explicit consideration of surface hydrophobic patches. Proteins. 80, 325-838 (2012).
Jaramillo et al. "Computational Protein Design Is a Challenge for Implicit Solvation Models" vol. 88, Issue 1, Jan. 2005, 156-171.
Joachimiak et al., Computational design of a new hydrogen bond network and at least a 300-fold specificity switch at a protein-protein interface. J Mol Biol. 361, 195-208 (2006).
Joh et al., De novo design of a transmembrane $Zn^{2+}$-transporting four-helix bundle. Science. 346, 1520-1524 (2014).
Judd et al., Hydrogen bonding networks tune proton-coupled redox steps during the enzymatic six-electron conversion of nitrite to ammonia. Biochemistry. 53, 5638-5646 (2014).
Käll et al., Semi-supervised learning for peptide identification from shotgun proteomics datasets. Nat Methods. 4, 323-925 (2007).
Kaplan et al., Increasing the affinity of selective bZIP-binding peptides through surface residue redesign. Protein Science. 23, 940-953 (2014).
Karanicolas et al., A de novo protein binding pair by computational design and directed evolution. Mol Cell. 42, 250-260 (2011).
King, Computational Design of Self-Assembling Protein Nanomaterials with Atomic Level Accuracy, Science, vol. 336: 1171-1174 (Jun. 2012).
Koga et al., Principles for designing ideal protein structures. Nature. 491, 222-227 (2012).
Kortemme et al., Computational redesign of protein-protein interaction specificity. Nat Struct Mol Biol. 11, 371-379 (2004).
Kuhlman, Design of a Novel Globular Protein Fold with Atomic-Level Accuracy. Science. 302, 1364-1368 (2003).
Kuhlman & Baker, Native protein sequences are close to optimal for their structures. Proc Natl Acad Sci USA. 97, 10383-10388 (2000).
Leaver-Fay et al., ROSETTA3: an object-oriented software suite for the simulation and design of macromolecules. Meth Enzymol. 487, 545-574 (2011).
Liu et al., Fast determination of the optimal rotational matrix for macromolecular superpositions. J. Comput. Chem. 31, 1561-1563 (2010).
Lumb & Kim, A buried polar interaction imparts structural uniqueness in a designed heterodimeric coiled coil. Biochemistry. 34, 8642-8648 (1995).
Zhang et al., Structural DNA nanotechnology: state of the art and future perspective. J Am Chem Soc. 136, 11198-11211 (2014).
McCoy et al., Phaser crystallographic software. Journal of applied crystallography. 40, 658-674 (2007).
Minami et al., MICAN: a protein structure alignment algorithm that can handle Multiple-chains, Inverse alignments, C (α) only models, Alternative alignments, and Non-sequential alignments. BMC Bioinformatics. 14, 24 (2013).
Ogata et al. "Automatic sequence design of major histocompatibility complex class I binding peptides impairing CD8+ T cell recognition" The Journal of Biological Chemistry, 278(2) Jan. 10, 2003, 1281-1290.
Ogihara et al., The crystal structure of the designed trimeric coiled coil coil-VaLd: implications for engineering crystals and supramolecular assemblies. Protein Sci. 6, 80-88 (1997).
O'Meara et al., A Combined Covalent-Electrostatic Model of Hydrogen Bonding Improves Structure Prediction with Rosetta. J. Chem. Theory Comput. 11, 609-622 (2015).
Otwinowski et al., Processing of X-ray Diffraction Data Collected in Oscillation Mode, Methods in Enzymology vol. 276 Part A. 276, 307-326 (1997).
Procko et al., Computational design of a protein-based enzyme inhibitor. J Mol Biol. 425, 3563-3575 (2013).

(56) References Cited

OTHER PUBLICATIONS

Rambo & Tainer, Characterizing flexible and intrinsically unstructured biological macromolecules by SAS using the Porod-Debye law. Biopolymers. 95, 559-571 (2011).
Reinke et al., Networks of bZIP protein-protein interactions diversified over a billion years of evolution. Science. 340, 730-734 (2013).
Reinke et al., A synthetic coiled-coil interactome provides heterospecific modules for molecular engineering. J Am Chem Soc. 132, 6025-6031 (2010).
Rothemund, Folding DNA to create nanoscale shapes and patterns. Nature. 440, 297-302 (2006).
Sánchez-Azqueta et al., A hydrogen bond network in the active site of Anabaena ferredoxin-NADP(+) reductase modulates its catalytic efficiency. Biochim Biophys Acta. 1837, 251-263 (2014).
Schneidman-Duhovny et al., FoXS: a web server for rapid computation and fitting of SAXS profiles. Nucleic Acids Res. 38, W540-4 (2010).
Schneidman-Duhovny et al., Accurate SAXS profile computation and its assessment by contrast variation experiments. Biophys J. 105, 962-974 (2013).
Sheinerman & Honig, On the role of electrostatic interactions in the design of protein-protein interfaces. J Mol Biol. 318, 161-177 (2002).
Stranges & Kuhlman, A comparison of successful and failed protein interface designs highlights the challenges of designing buried hydrogen bonds. Protein Science (2012).
Street & Mayo, Computational protein design. Structure. 7, R105-9 (1999).
Tatko et al., Polar networks control oligomeric assembly in membranes. J Am Chem Soc. 128, 4170-4171 (2006).
Thomas et al., A set of de novo designed parallel heterodimeric coiled coils with quantified dissociation constants in the micromolar to sub-nanomolar regime. J Am Chem Soc. 135, 5161-5166 (2013).
Thomson et al., Computational design of water-soluble α-helical barrels. Science. 346, 485-488 (2014).
Wei et al., Complex shapes self-assembled from single-stranded DNA tiles. Nature. 485, 623-626 (2012).
Wernisch et al. "Automatic protein design with all atom force-fields by exact and heuristic optimization" Journal of Molecular Biology, vol. 301, Issue 3, Aug. 18, 2000, 713-736.
Winfree et al., Design and self-assembly of two-dimensional DNA crystals. Nature. 394, 539-544 (1998).
Woolfson & Alber, Predicting oligomerization states of coiled coils. Protein Sci. 4, 1596-1607 (1995).
Xu et al., Hydrogen bonds and salt bridges across protein-protein interfaces. Protein Eng. 10, 999-1012 (1997).
Zhang et al., Proteomic parsimony through bipartite graph analysis improves accuracy and transparency. J Proteome Res. 6, 3549-3557 (2007).
The International Search Report (ISR) with Written Opinion for PCT/US2017/025532 dated Aug. 11, 2017, pp. 1-14.
Canutescu, Adrian A. et al. "A graph-theory algorithm for rapid protein side-chain prediction" Protein Science (2003) vol. 12, pp. 2001-2014.
Boyken, Scott E. et al. "De novo design of protein homo-oligomers with modular hydrogen-bond network-mediated specificity" Science (2016) vol. 325, pp. 680-687.
Das, Rhiju et al. "Simultaneous prediction of protein folding and docking at high resolution" PNAS (2009) vol. 106, pp. 18978-18983.
Pace et al., "Forces stabilizing proteins" FEBS Letters 588(14):2177-84 (May 2014).
Song et al., "High-Resolution Comparative Modeling with RosettaCM" Structure 21(10):1735-42 (Oct. 2013).
The PyMOL Molecular Graphics System, version 1.7.4, released Dec. 3, 2014, (Schrödinger, LLC) pp. 1-9.

\* cited by examiner

SEQUENCE LISTING

```
<160> NUMBER OF SEQ ID NOS: 94

<210> SEQ ID NO 1
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is R, K, E, D
<220> FEATURE:
<221> NAME/KEY: MISC_FEATURE
<222> LOCATION: (3)..(5)
<223> OTHER INFORMATION: X is N, Q, E, D, R, K, S, or T
<220> FEATURE:
<221> NAME/KEY: MISC_FEATURE
<222> LOCATION: (7)..(8)
<223> OTHER INFORMATION: X is S, T, N, Q, E, or D
<220> FEATURE:
<221> NAME/KEY: MISC_FEATURE
<222> LOCATION: (9)..(9)
<223> OTHER INFORMATION: X is S, T, N, or D
<220> FEATURE:
<221> NAME/KEY: MISC_FEATURE
<222> LOCATION: (11)..(11)
<223> OTHER INFORMATION: X is E, D, R, or K
<220> FEATURE:
<221> NAME/KEY: MISC_FEATURE
<222> LOCATION: (13)..(13)
<223> OTHER INFORMATION: X is E, D, R, or K

<400> SEQUENCE: 1

Xaa Leu Xaa Xaa Xaa Gly Xaa Xaa Xaa Glu Xaa Val Xaa
1               5                   10

<210> SEQ ID NO 2
<211> LENGTH: 75
<212> TYPE: PRT
<213> ORGANISM: Artificial Sequence
<220> FEATURE:
<223> OTHER INFORMATION: Synthetic

<400> SEQUENCE: 2

Thr Arg Thr Arg Ser Leu Arg Glu Gln Glu Glu Ile Ile Arg Glu Leu
1               5                   10                  15

Glu Arg Ser Leu Arg Glu Gln Glu Glu Leu Leu Arg Glu Leu Glu Arg
                20                  25                  30

Leu Gln Arg Glu Gly Ser Ser Asp Glu Asp Val Arg Glu Leu Leu Arg
            35                  40                  45

Glu Ile Lys Lys Leu Ala Arg Glu Gln Lys Tyr Leu Val Glu Glu Leu
        50                  55                  60

Lys Lys Leu Ala Arg Glu Gln Lys Arg Gln Asp
65                  70                  75
```

<210> SEQ ID NO 3
<211> LENGTH: 75
<212> TYPE: PRT
<213> ORGANISM: Artificial Sequence
<220> FEATURE:
<223> OTHER INFORMATION: Synthetic

<400> SEQUENCE: 3

```
Thr Arg Thr Glu Ile Ile Arg Glu Leu Glu Arg Ser Leu Arg Glu Gln
1               5                   10                  15

Glu Arg Ser Leu Arg Glu Gln Glu Leu Leu Arg Glu Leu Glu Arg
            20                  25                  30

Leu Gln Arg Glu Gly Ser Ser Asp Glu Asp Val Arg Glu Leu Leu Arg
            35                  40                  45

Glu Ile Lys Lys Leu Ala Arg Glu Gln Lys Lys Leu Ala Arg Glu Gln
        50                  55                  60

Lys Tyr Leu Val Glu Glu Leu Lys Arg Gln Asp
65                  70                  75
```

<210> SEQ ID NO 4
<211> LENGTH: 75
<212> TYPE: PRT
<213> ORGANISM: Artificial Sequence
<220> FEATURE:
<223> OTHER INFORMATION: Synthetic

<400> SEQUENCE: 4

```
Thr Arg Thr Glu Ile Ile Arg Glu Leu Glu Arg Ser Leu Arg Glu Gln
1               5                   10                  15

Glu Glu Leu Ala Lys Arg Leu Lys Arg Ser Leu Arg Glu Gln Glu Arg
            20                  25                  30

Leu Gln Arg Glu Gly Ser Ser Asp Glu Asp Val Arg Lys Leu Ala Arg
            35                  40                  45

Glu Gln Lys Glu Leu Val Glu Glu Ile Glu Lys Leu Ala Arg Glu Gln
        50                  55                  60

Lys Tyr Leu Val Glu Glu Leu Lys Arg Gln Asp
65                  70                  75
```

<210> SEQ ID NO 5
<211> LENGTH: 75
<212> TYPE: PRT
<213> ORGANISM: Artificial Sequence
<220> FEATURE:
<223> OTHER INFORMATION: Synthetic

<400> SEQUENCE: 5

```
Thr Arg Thr Glu Ile Ile Arg Glu Leu Glu Leu Ala Lys Arg Leu
1               5                   10                  15

Lys Arg Ser Leu Arg Glu Gln Glu Ser Leu Arg Glu Gln Glu Arg
            20                  25                  30

Leu Gln Arg Glu Gly Ser Ser Asp Glu Asp Val Arg Lys Leu Ala Arg
            35                  40                  45

Glu Gln Lys Lys Leu Ala Arg Glu Gln Lys Glu Leu Val Glu Glu Ile
        50                  55                  60

Glu Tyr Leu Val Glu Glu Leu Lys Arg Gln Asp
65                  70                  75
```

<210> SEQ ID NO 6
<211> LENGTH: 76
<212> TYPE: PRT
<213> ORGANISM: Artificial Sequence

```
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 6

Gly Thr Ala Ile Glu Ala Asn Ser Arg Met Leu Lys Ala Leu Ile Glu
1               5                   10                  15

Ile Ala Lys Ala Ile Trp Lys Ala Leu Trp Ala Asn Ser Leu Leu Leu
                20                  25                  30

Glu Ala Thr Ser Arg Gly Asp Thr Glu Arg Met Arg Gln Trp Ala Glu
            35                  40                  45

Glu Ala Arg Glu Ile Tyr Lys Glu Ala Lys Lys Ile Ile Asp Glu Ala
    50                  55                  60

Asp Glu Ile Val Lys Glu Ala Lys Glu Arg His Asp
65                  70                  75

<210> SEQ ID NO 7
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (86)..(87)
<223> OTHER INFORMATION: optionally absent

<400> SEQUENCE: 7

Ser Glu Glu Leu Arg Ala Val Ala Asp Leu Gln Arg Leu Asn Ile Glu
1               5                   10                  15

Leu Ala Arg Lys Leu Leu Glu Ala Val Ala Arg Leu Gln Glu Leu Asn
                20                  25                  30

Ile Asp Leu Val Arg Lys Thr Ser Glu Leu Thr Asp Glu Lys Thr Ile
            35                  40                  45

Arg Glu Glu Ile Arg Lys Val Lys Glu Ser Lys Arg Ile Val Glu
    50                  55                  60

Glu Ala Glu Glu Glu Ile Arg Arg Ala Lys Glu Glu Ser Arg Tyr Ile
65                  70                  75                  80

Ala Asp Glu Ser Arg Gly Ser
                85

<210> SEQ ID NO 8
<211> LENGTH: 77
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 8

Gly Thr Ser Asp Tyr Ile Ile Glu Gln Ile Gln Arg Asp Gln Glu Glu
1               5                   10                  15

Ala Arg Lys Lys Val Glu Glu Ala Glu Glu Arg Leu Glu Arg Val Lys
                20                  25                  30

Glu Ala Ser Lys Arg Gly Val Ser Asp Gln Leu Leu Asp Leu Ile
            35                  40                  45
```

```
Arg Glu Leu Ala Glu Ile Ile Glu Leu Ile Arg Ile Ile Arg Arg
 50                  55                  60

Ser Asn Glu Ala Ile Lys Glu Leu Ile Lys Asn Gln Ser
 65                  70                  75
```

<210> SEQ ID NO 9
<211> LENGTH: 77
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 9

```
Gly Ser Glu Asp Tyr Lys Leu Arg Glu Ala Gln Arg Glu Leu Asp Lys
 1               5                  10                  15

Gln Arg Lys Asp Thr Glu Glu Ile Arg Lys Arg Leu Lys Glu Ile Gln
                20                  25                  30

Arg Leu Thr Asp Glu Arg Thr Ser Thr Ala Asp Glu Leu Ile Lys Glu
            35                  40                  45

Leu Arg Glu Ile Ile Arg Arg Leu Gln Glu Gln Ser Glu Lys Leu Arg
 50                  55                  60

Glu Ile Ile Glu Glu Leu Glu Lys Ile Ile Arg Lys Arg
 65                  70                  75
```

<210> SEQ ID NO 10
<211> LENGTH: 76
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 10

```
Gly Thr Arg Thr Glu Ile Ile Arg Glu Leu Glu Arg Ser Leu Arg Glu
 1               5                  10                  15

Gln Glu Glu Leu Ala Lys Arg Leu Lys Glu Leu Leu Arg Glu Leu Glu
                20                  25                  30

Arg Leu Gln Arg Glu Gly Ser Ser Asp Glu Val Arg Glu Leu Leu
            35                  40                  45

Arg Glu Ile Lys Glu Leu Val Glu Glu Ile Glu Lys Leu Ala Arg Glu
 50                  55                  60

Gln Lys Tyr Leu Val Glu Glu Leu Lys Arg Gln Asp
 65                  70                  75
```

<210> SEQ ID NO 11
<211> LENGTH: 77
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 11

```
Gly Thr Asp Thr Asp Glu Leu Leu Arg Leu Ala Lys Glu Gln Ala Glu
```

```
                1               5                   10                  15
Leu Leu Lys Glu Ile Lys Lys Leu Val Glu Glu Ile Ala Arg Leu Val
                20                  25                  30

Lys Glu Ile Gln Glu Asp Pro Ser Asp Glu Leu Leu Lys Thr Leu Ala
                35                  40                  45

Glu Leu Val Arg Lys Leu Lys Glu Leu Val Glu Asp Met Glu Arg Ser
            50                  55                  60

Met Lys Glu Gln Leu Tyr Ile Ile Lys Gln Lys Ser
65                  70                  75
```

<210> SEQ ID NO 12
<211> LENGTH: 71
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 12

```
Gly Ser Lys Asp Thr Glu Asp Ser Arg Lys Ile Trp Glu Asp Ile Arg
1               5                   10                  15

Arg Leu Leu Glu Glu Ala Arg Lys Asn Ser Glu Glu Ile Trp Lys Glu
                20                  25                  30

Ile Thr Lys Asn Pro Asp Thr Ser Glu Ile Ala Arg Leu Leu Ser Glu
                35                  40                  45

Gln Leu Leu Glu Ile Ala Glu Met Leu Val Arg Ile Ala Glu Leu Leu
            50                  55                  60

Ser Arg Gln Thr Glu Gln Arg
65                  70
```

<210> SEQ ID NO 13
<211> LENGTH: 75
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 13

```
Gly Thr Lys Tyr Glu Ile Arg Glu Ala Leu Lys Glu Ala Gln Lys Gln
1               5                   10                  15

Leu Glu Asp Leu Lys Arg Met Leu Asp Glu Leu Arg Arg Asn Leu Glu
                20                  25                  30

Glu Leu Lys Arg Asn Pro Ser Glu Asp Ala Leu Val Glu Asn Asn Glu
                35                  40                  45

Leu Ile Val Arg Val Leu Glu Val Ile Val Glu Asn Asn Arg Ser Ile
            50                  55                  60

Ile Glu Ile Leu Lys Leu Leu Ala Lys Ser Asp
65                  70                  75
```

<210> SEQ ID NO 14
<211> LENGTH: 75
<212> TYPE: PRT
<213> ORGANISM: Artificial Sequence
<220> FEATURE:
<223> OTHER INFORMATION: Synthetic

```
<220> FEATURE:
<221> NAME/KEY: MISC_FEATURE
<222> LOCATION: (1)..(1)
<223> OTHER INFORMATION: optionally absent

<400> SEQUENCE: 14

Gly Thr Lys Tyr Lys Ile Arg Glu Met Leu Glu Ala Lys Arg Ser
1               5                   10                  15

Leu Glu Glu Leu Arg Arg Ile Leu Glu Lys Leu Lys Glu Ser Leu Arg
            20                  25                  30

Glu Leu Arg Arg Asn Pro Ser Glu Asp Ala Leu Val Asn Asn Asn Glu
        35                  40                  45

Val Ile Val Lys Ala Ile Glu Ala Ser Val Glu Asn Gln Arg Ile Ile
    50                  55                  60

Ile Glu Leu Ala Arg Met Leu Ala Glu Ser Asp
65                  70                  75

<210> SEQ ID NO 15
<211> LENGTH: 75
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 15

Gly Thr Lys Tyr Arg Ile Lys Asp Thr Leu Arg Glu Leu Lys Arg Ala
1               5                   10                  15

Leu Glu Glu Leu Lys Lys Ile Leu Glu Glu Leu Gln Arg Ser Leu Glu
            20                  25                  30

Glu Leu Arg Arg Asn Pro Ser Glu Asp Ala Leu Val Asn Asn Asn Glu
        35                  40                  45

Val Ile Val Lys Ala Ile Glu Ala Ala Val Arg Ala Ile Glu Ile Ser
    50                  55                  60

Ala Glu Asn Gln Arg Met Leu Ala Glu Ser Asp
65                  70                  75

<210> SEQ ID NO 16
<211> LENGTH: 75
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 16

Gly Thr Lys Tyr Glu Ala Arg Lys Gln Leu Glu Glu Met Lys Lys Gln
1               5                   10                  15

Leu Lys Asp Leu Lys Arg Ser Leu Glu Arg Leu Arg Glu Ile Leu Glu
            20                  25                  30

Arg Leu Glu Glu Asn Pro Ser Glu Asp Val Ile Val Glu Ala Ile Arg
        35                  40                  45

Ala Ile Val Glu Asn Asn Lys Gln Ile Val Glu Asn Asn Arg Ser Ile
    50                  55                  60

Ile Glu Asn Asn Glu Thr Ile Ile Arg Ser Asp
65                  70                  75
```

<210> SEQ ID NO 17
<211> LENGTH: 75
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 17

```
Gly Thr Lys Tyr Glu Leu Arg Arg Gln Leu Glu Glu Leu Glu Lys Leu
1               5                   10                  15

Leu Arg Glu Leu Arg Lys Ser Leu Asp Glu Leu Arg Lys Ile Leu Glu
                20                  25                  30

Glu Leu Glu Arg Asn Pro Ser Glu Asp Val Ile Val Arg Ala Ile Lys
            35                  40                  45

Ala Ser Val Lys Asn Gln Glu Ile Ile Val Glu Val Leu Arg Ala Ile
        50                  55                  60

Ile Glu Asn Asn Lys Thr Ile Ala Lys Ser Asp
65                  70                  75
```

<210> SEQ ID NO 18
<211> LENGTH: 75
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 18

```
Gly Thr Lys Tyr Glu Leu Arg Arg Ala Leu Glu Glu Leu Glu Lys Ala
1               5                   10                  15

Leu Gln Glu Leu Arg Glu Met Leu Arg Lys Leu Lys Glu Ser Leu Glu
                20                  25                  30

Glu Leu Lys Lys Asn Pro Ser Glu Asp Ala Leu Val Arg Asn Asn Glu
            35                  40                  45

Leu Ile Val Glu Val Leu Arg Val Ile Val Glu Val Leu Ser Ile Ile
        50                  55                  60

Ala Arg Val Leu Glu Ile Asn Ala Arg Ser Asp
65                  70                  75
```

<210> SEQ ID NO 19
<211> LENGTH: 75
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 19

```
Gly Thr Lys Tyr Glu Leu Arg Arg Ala Leu Glu Glu Leu Glu Lys Ala
1               5                   10                  15

Leu Arg Glu Leu Lys Lys Ser Leu Asp Glu Leu Glu Arg Ser Leu Glu
                20                  25                  30
```

```
Glu Leu Glu Lys Asn Pro Ser Glu Asp Ala Leu Val Glu Asn Asn Arg
         35                  40                  45

Leu Asn Val Glu Asn Asn Lys Ile Ile Val Glu Val Leu Arg Ile Ile
 50                  55                  60

Ala Glu Val Leu Lys Ile Asn Ala Lys Ser Asp
 65                  70                  75
```

<210> SEQ ID NO 20
<211> LENGTH: 75
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 20

```
Gly Thr Lys Tyr Lys Ile Lys Glu Thr Leu Lys Arg Leu Glu Asp Ser
 1               5                  10                  15

Leu Arg Glu Leu Arg Arg Ile Leu Glu Glu Leu Lys Glu Met Leu Glu
                 20                  25                  30

Arg Leu Glu Lys Asn Pro Asp Lys Asp Val Ile Val Glu Val Leu Lys
         35                  40                  45

Val Ile Val Lys Ala Ile Glu Ala Ser Val Glu Asn Gln Arg Ile Ser
 50                  55                  60

Ala Glu Asn Gln Lys Ala Leu Ala Glu Ser Asp
 65                  70                  75
```

<210> SEQ ID NO 21
<211> LENGTH: 75
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 21

```
Gly Thr Lys Tyr Glu Ile Lys Lys Ala Leu Lys Glu Leu Glu Glu Ala
 1               5                  10                  15

Ile Gln Lys Leu Lys Lys Ser Leu Lys Glu Leu Lys Glu Ser Leu Lys
                 20                  25                  30

Glu Leu Gln Lys Asn Pro Ser Glu Asp Ala Leu Val Lys Asn Asn Ser
         35                  40                  45

Leu Asn Val Ala Asn Asn Glu Ile Ile Val Glu Val Leu Glu Ile Ile
 50                  55                  60

Ala Arg Ile Leu Glu Leu Leu Ala Arg Ser Asp
 65                  70                  75
```

<210> SEQ ID NO 22
<211> LENGTH: 75
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 22

Gly Thr Lys Tyr Glu Ile Lys Glu Ala Leu Arg Glu Leu Asn Arg Ala
1               5                   10                  15

Leu Lys Glu Leu Lys Glu Ala Leu Arg Glu Leu Glu Arg Ser Leu Arg
            20                  25                  30

Glu Leu Gln Lys Asn Pro Asp Lys Asp Ala Leu Val Arg Asn Asn Glu
        35                  40                  45

Leu Asn Val Asp Val Ala Arg Ile Ile Val Glu Val Leu Ser Ile Ile
    50                  55                  60

Ala Arg Val Leu Glu Leu Leu Ala Lys Ser Asp
65                  70                  75

<210> SEQ ID NO 23
<211> LENGTH: 75
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 23

Gly Thr Lys Tyr Glu Leu Arg Arg Ala Leu Glu Glu Leu Glu Lys Ala
1               5                   10                  15

Leu Gln Glu Leu Arg Glu Met Leu Arg Lys Leu Lys Glu Ser Leu Glu
            20                  25                  30

Glu Leu Lys Lys Asn Pro Ser Glu Asp Ala Leu Val Arg Asn Asn Glu
        35                  40                  45

Leu Ile Val Glu Val Leu Arg Val Ile Val Glu Val Leu Ser Ile Ile
    50                  55                  60

Ala Arg Val Leu Glu Ile Asn Ala Arg Ser Asp
65                  70                  75

<210> SEQ ID NO 24
<211> LENGTH: 75
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 24

Gly Thr Lys Tyr Glu Leu Arg Arg Ala Leu Glu Glu Leu Glu Lys Ala
1               5                   10                  15

Leu Arg Glu Leu Lys Lys Ser Leu Asp Glu Leu Glu Arg Ser Leu Glu
            20                  25                  30

Glu Leu Glu Lys Asn Pro Ser Glu Asp Ala Leu Val Glu Asn Asn Arg
        35                  40                  45

Leu Asn Val Glu Asn Asn Lys Ile Ile Val Glu Val Leu Arg Ile Ile
    50                  55                  60

Ala Glu Val Leu Lys Ile Asn Ala Lys Ser Asp
65                  70                  75

<210> SEQ ID NO 25
<211> LENGTH: 75
<212> TYPE: PRT

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 25

Gly Thr Lys Tyr Glu Leu Arg Glu Ala Ile Arg Lys Leu Glu Glu Ala
1               5                   10                  15
Leu Arg Lys Leu Lys Lys Ala Leu Asp Glu Leu Arg Lys Ser Leu Glu
                20                  25                  30
Glu Leu Lys Lys Asn Pro Ser Glu Asp Ala Leu Val Arg Asn Asn Glu
            35                  40                  45
Leu Asn Val Lys Val Ala Glu Ile Ile Val Lys Val Leu Lys Ile Ile
        50                  55                  60
Ala Glu Ala Ile Lys Ile Asn Ala Lys Ser Asp
65                  70                  75

<210> SEQ ID NO 26
<211> LENGTH: 74
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 26

Gly Thr Glu Glu Tyr Lys Leu Arg Glu Leu Leu Lys Arg His Asn Glu
1               5                   10                  15
Val Leu Lys Glu Leu Gln Lys Ala Ala Lys Glu Ala Glu Glu Val Ala
                20                  25                  30
Glu Arg Phe Lys Lys Thr Asn Asp Ile Thr Glu Ala Ile Arg Val Ile
            35                  40                  45
Ala Asp Leu Leu Arg Ala Ile Val Lys Ala Ile Glu Thr Asn Ser Arg
        50                  55                  60
Val Val Lys Met Ile Val Glu Leu Asn Glu
65                  70

<210> SEQ ID NO 27
<211> LENGTH: 75
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 27

Gly Thr Lys Tyr Ile Glu Lys Leu Leu Arg Glu Ala Gln Arg Thr Leu
1               5                   10                  15
Glu Glu Leu Lys Arg Leu Leu Glu Glu Leu Lys Glu Met Leu Lys Glu
                20                  25                  30
Leu Glu Arg Ala Asn Ala Thr Asp Ala Arg Leu Ile Ala Glu Val Ile
            35                  40                  45
Arg Val Ile Val Glu Val Leu Arg Ala Ser Val Glu Asn Gln Glu Met
        50                  55                  60
```

Ile Ile Arg Ile Leu Lys Ala Ile Thr Glu Glu
65                  70                  75

<210> SEQ ID NO 28
<211> LENGTH: 76
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (75)..(76)
<223> OTHER INFORMATION: optionally absent

<400> SEQUENCE: 28

Thr Glu Lys Asp Val Leu Arg Ile Ile Val Lys Asn Glu Ile Ile
1               5                   10                  15

Val Lys Val Leu Ser Val Ile Ala Glu Val Leu Lys Ile Ile Ala Lys
                20                  25                  30

Ile Leu Glu Asn Pro Ser Glu Tyr Met Leu Lys Glu Leu Lys Lys Ala
            35                  40                  45

Leu Lys Glu Leu Glu Lys Met Leu Lys Glu Leu Arg Lys Ser Leu Lys
50                  55                  60

Glu Leu Lys Glu Ala Leu Arg Glu Leu Glu Gly Ser
65                  70                  75

<210> SEQ ID NO 29
<211> LENGTH: 75
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 29

Gly Thr Leu Asp Tyr Lys Leu Asp Glu Met Leu Lys Lys Leu Glu Lys
1               5                   10                  15

Ser Arg Glu Glu Met Glu Lys Met Ala Gln Glu Leu Arg Arg Ala Leu
                20                  25                  30

Glu Glu Leu Glu Lys Asn Ser Asn Val Asp Lys Val Leu Lys Ile Ile
            35                  40                  45

Ile Lys Ala Ile Gln Leu Ser Ile Glu Asn Gln Lys Leu Asn Leu Glu
50                  55                  60

Ala Val Arg Leu Leu Ile Glu Ala Gln Lys Ser
65                  70                  75

<210> SEQ ID NO 30
<211> LENGTH: 75
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 30

Gly Thr Lys Tyr Lys Ile Lys Glu Thr Leu Lys Arg Leu Glu Asp Ser
1               5                   10                  15

Leu Arg Glu Leu Arg Arg Ile Leu Glu Glu Leu Lys Glu Met Leu Glu
                20                  25                  30

Arg Leu Glu Lys Asn Pro Asp Lys Asp Val Ile Val Glu Val Leu Lys
             35                  40                  45

Val Ile Val Lys Ala Ile Glu Ala Ser Val Glu Asn Gln Arg Ile Ser
 50                  55                  60

Ala Glu Asn Gln Lys Ala Leu Ala Glu Ser Asp
 65                  70                  75

<210> SEQ ID NO 31
<211> LENGTH: 77
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 31

Gly Thr Asp Glu Tyr Lys Trp Lys Glu Glu Val Arg Arg Phe Glu Glu
 1               5                  10                  15

Glu Ala Lys Lys Trp Glu Glu Leu Lys Glu Met Arg Lys Arg Ile
                20                  25                  30

Glu Asp Ala Lys Lys Gly Arg Pro Thr Leu Lys Val Asn Leu Glu Ala
             35                  40                  45

Ala Glu Ala Leu Leu Glu Ala Ala Arg Leu Ile Val Glu Ala Ala Lys
 50                  55                  60

Leu Leu Leu Ala Ala Ala Lys Leu Asn Glu Lys Gln Asn
 65                  70                  75

<210> SEQ ID NO 32
<211> LENGTH: 77
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 32

Gly Ser Asp Glu Asp Arg Lys Ala Lys Glu Leu Ile Glu Arg Gln Arg
 1               5                  10                  15

Lys Leu Thr Asp Glu Ala Glu Trp Ala Lys Gln Asn Glu Glu Ile
                20                  25                  30

Ala Lys Lys Ile Glu Lys Gln Pro Asp Thr Ser Leu Val Ala Arg Met
             35                  40                  45

Leu Ala Asn Val Ser Arg Met Leu Leu Ala Thr Asn Arg Ala Leu Leu
 50                  55                  60

Ala Asn Thr Glu Ala Leu Glu Ala Leu Ile Arg Lys Thr
 65                  70                  75

<210> SEQ ID NO 33
<211> LENGTH: 76
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE

```
<222> LOCATION: (1)..(1)
<223> OTHER INFORMATION: optionally absent

<400> SEQUENCE: 33

Gly Thr Ala Ile Glu Ala Asn Ser Arg Met Leu Lys Ala Leu Ile Glu
1               5                   10                  15

Ile Ala Lys Ala Ile Trp Lys Ala Leu Trp Ala Asn Ser Leu Leu Leu
                20                  25                  30

Glu Ala Thr Ser Arg Gly Asp Thr Glu Arg Met Arg Gln Trp Ala Glu
            35                  40                  45

Glu Ala Arg Glu Ile Tyr Lys Glu Ala Lys Lys Ile Ile Asp Glu Ala
        50                  55                  60

Asp Glu Ile Val Lys Glu Ala Lys Glu Arg His Asp
65                  70                  75

<210> SEQ ID NO 34
<211> LENGTH: 135
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (134)..(135)
<223> OTHER INFORMATION: optionally absent

<400> SEQUENCE: 34

Ser Ala Leu Glu Lys Ile Ala Lys Leu Ile Glu Ala Ala Arg Leu
1               5                   10                  15

Ser Ala Glu Leu Ala Arg Arg Ala Ala Arg Ala Ser Ala Glu Met Ala
                20                  25                  30

Arg Lys Ala Ile Glu Ala Val Ser Glu Arg Gly Ser Glu Ser Leu
            35                  40                  45

Leu Lys Ile Val Ala Asp Leu Ile Val Glu Ser Gln Glu Ala Val Val
        50                  55                  60

Arg Leu Ile Ile Glu Ser Gln Gln Ile Ala Ala Lys Leu Ala Glu Asp
65                  70                  75                  80

Leu Ile Arg Ala Ala Lys Glu Ala Ala Ser Asp Glu Ser Lys Met Glu
                85                  90                  95

Glu Val Ala Lys Glu Val Gln Glu Arg Ala Glu Arg Ala Ala Arg Asp
                100                 105                 110

Ile Glu Arg Lys Leu Lys Arg Val Leu Glu Glu Leu Asp Tyr Lys Leu
            115                 120                 125

Lys Glu Ser Arg Asp Gly Ser
        130                 135

<210> SEQ ID NO 35
<211> LENGTH: 135
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (134)..(135)
<223> OTHER INFORMATION: optionally absent

<400> SEQUENCE: 35

Thr Ala Leu Glu Ile Ala Val Arg Leu Asn Arg Glu Ala Ala Arg Glu
1               5                   10                  15

Ala Ala Arg Glu Asn Ala Asp Thr Ala Arg Lys Ala Ala Arg Arg Ile
```

```
                20                  25                  30
Ala Glu Val Ala Lys Arg Leu Ala Glu Glu Asn Arg Asp Ala Lys Leu
            35                  40                  45

Ala Ala Arg Leu Leu Ala Glu Ile Ala Arg Leu Leu Ala Glu Leu Ile
        50                  55                  60

Ala Arg Gln Ser Glu Leu Ala Glu Trp Leu Ala Thr Gln Ser Lys
65                  70                  75                  80

Leu Ala Ala Glu Leu Ala Arg Lys Asp Thr Ser Ala Thr Asp Glu Ala
                85                  90                  95

Glu Arg Ile Arg Lys Glu Ser Glu Leu Leu Asp Lys Val Arg Glu
            100                 105                 110

Glu Ile Lys Arg Leu Glu Asp Glu Val Ser Lys Thr Ile Glu Glu Leu
        115                 120                 125

Ser Glu Arg Val Arg Gly Ser
    130                 135

<210> SEQ ID NO 36
<211> LENGTH: 135
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (134)..(135)
<223> OTHER INFORMATION: optionally absent

<400> SEQUENCE: 36

Ser Ile Leu Glu Leu Ala His Glu Ser Asn Arg Ala Leu Glu Met
1               5                   10                  15

Ala Ser Arg Ala Asn Arg Glu Ala Met Lys Ala Ala Arg Glu Met Ile
            20                  25                  30

Arg Ala Ala Ser Glu Ala Ala Arg Arg Ala Gly Ser Ser Asn Asp Lys
        35                  40                  45

Asp Ser Leu Arg Met Ile Glu Glu Ala Leu Arg Leu Ala Leu Arg Met
    50                  55                  60

Ile Glu Glu Thr Asn Lys Lys Ala Val Arg Met Val Leu Glu Asn Asn
65                  70                  75                  80

Arg Lys Met Val Glu Ala Glu Lys Lys Lys Leu Ser Glu Glu Ile
            85                  90                  95

Lys Arg Ile Ala Lys Glu Thr Glu Asp Arg Met Arg Glu Ile Ala Arg
        100                 105                 110

Arg Ala Ser Glu Glu Ala Arg Arg Leu Ala Glu Glu Ile Lys Arg Glu
    115                 120                 125

Ala Asp Tyr Arg Ser Gly Ser
    130                 135

<210> SEQ ID NO 37
<211> LENGTH: 86
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (85)..(86)
<223> OTHER INFORMATION: optionally absent

<400> SEQUENCE: 37

Glu Glu Leu Arg Ala Val Ala Asp Leu Gln Arg Leu Asn Ile Glu Leu
```

```
                1               5                   10                  15
Ala Arg Lys Leu Leu Glu Ala Val Ala Arg Leu Gln Glu Leu Asn Ile
            20                  25                  30

Asp Leu Val Arg Lys Thr Ser Glu Leu Thr Asp Glu Lys Thr Ile Arg
            35                  40                  45

Glu Glu Ile Arg Lys Val Lys Glu Ser Lys Arg Ile Val Glu Glu
            50                  55                  60

Ala Glu Glu Ile Arg Arg Ala Lys Glu Ser Arg Tyr Ile Ala
65                  70                  75                  80

Asp Glu Ser Arg Gly Ser
                85

<210> SEQ ID NO 38
<211> LENGTH: 85
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 38

Gly Thr Glu Arg Lys Asp Arg Leu Arg Lys Glu Leu Lys Arg Ile Ala
1               5                   10                  15

Glu Glu Thr Asp Lys Trp Val Glu Glu Leu Lys Glu Glu Leu Glu Arg
            20                  25                  30

Ile Leu Arg Thr Ile Glu Glu Leu Arg Lys Asp Pro Ser Ser Glu Val
            35                  40                  45

Ile Val Asp Ile Ala Arg Ile Gln Leu Glu Ala Leu Arg Glu Val Ile
            50                  55                  60

Arg Val Val Ala Glu Asn Ser Lys Ala Ile Leu Glu Ala Ile His Arg
65                  70                  75                  80

Val Ile Glu Glu Gly
                85

<210> SEQ ID NO 39
<211> LENGTH: 92
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (91)..(92)
<223> OTHER INFORMATION: optionally absent

<400> SEQUENCE: 39

Ser Lys Glu Val Arg Leu Gln Lys Leu Asn Ala Glu Ile Met Lys Glu
1               5                   10                  15

Ile Met Glu Leu Ile Ile Arg Leu Gln Glu Ala Asn Ala Arg Ile Ile
            20                  25                  30

Glu Glu Leu Val Arg Leu Ile Ile Asp Leu Glu Arg Ser Thr Asp Ser
            35                  40                  45

Lys Arg Met Ile Glu Ile Arg Val Ala Glu Arg Ala Ile Glu
            50                  55                  60

Glu Ser Lys Arg Leu Leu Glu Glu Ala Glu Lys Ala Met Arg Arg Ala
65                  70                  75                  80

Ile Tyr Glu Ser Glu Asp Ala Leu Arg Glu Gly Ser
```

<210> SEQ ID NO 40
<211> LENGTH: 87
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 40

Gly Ser Lys Val Glu Glu Leu Leu Arg Lys Ser Glu Glu Ala Ala Glu
1               5                   10                  15

Arg Ala Lys Arg Glu Leu Glu Arg Leu Leu Glu Glu Ser Glu Arg Ile
            20                  25                  30

Val Ala Glu Ala Gln Ala Leu Ala Glu Lys Tyr Glu Ser Gln Lys Val
        35                  40                  45

Trp Val Arg Ile Leu Ile Glu Leu Ile Arg Ala Thr Asn Arg Met Leu
    50                  55                  60

Ala Glu Ile Ala Arg Ile Leu Leu Glu Met Ile Glu Val Thr Asn Arg
65                  70                  75                  80

Met Ile Ala Glu Ser Thr Lys
                85

<210> SEQ ID NO 41
<211> LENGTH: 92
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (91)..(92)
<223> OTHER INFORMATION: optionally absent

<400> SEQUENCE: 41

Ser Glu Gln Leu Lys Glu Ile Ala Arg Ile Leu Ile Lys Leu Ile Glu
1               5                   10                  15

Ser Leu Thr Arg Phe Ile Leu Glu Val Ala Arg Ile Leu Ile Glu Leu
            20                  25                  30

Ile Glu Glu Thr Gln Arg Leu Ile Val Ala Ser Thr Asp Ser Asp Glu
        35                  40                  45

Ser Glu Leu Glu Arg Ile Ala Arg Glu Ser Lys Lys Lys Ala Lys Lys
    50                  55                  60

Ala Leu Asp Glu Leu Lys Lys Ile Val Asp Asp Gln Arg Arg Glu Ala
65                  70                  75                  80

Lys Lys Ala Ile Glu Glu Leu Glu Tyr Asp Gly Ser
                85                  90

<210> SEQ ID NO 42
<211> LENGTH: 71
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 42

Gly Ser Lys Asp Thr Glu Asp Ser Arg Lys Ile Trp Glu Asp Ile Arg
1               5                   10                  15

Arg Leu Leu Glu Glu Ala Arg Lys Asn Ser Glu Ile Trp Lys Glu
            20                  25                  30

Ile Thr Lys Asn Pro Asp Thr Ser Glu Ile Ala Arg Leu Leu Ser Glu
            35                  40                  45

Gln Leu Leu Glu Ile Ala Glu Met Leu Val Arg Ile Ala Glu Leu Leu
        50                  55                  60

Ser Arg Gln Thr Glu Gln Arg
65              70

<210> SEQ ID NO 43
<211> LENGTH: 76
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 43

Gly Thr Ala Tyr Glu Leu Leu Arg Lys Ala Glu Glu Leu Glu Lys Lys
1               5                   10                  15

Gln Gln Glu Leu Leu Lys Arg Gln Glu Leu Ala Lys Thr Ala Glu
            20                  25                  30

Glu Leu Arg Lys Lys Gly Gly Asn Ala Asp Ser Met Met Lys Ile Ile
            35                  40                  45

Lys Glu Ser Thr Arg Ile Val Arg Glu Ser Thr Glu Ile Val Lys Glu
        50                  55                  60

Leu Leu Lys Ile Ile Arg Glu Leu Arg Arg Gln Ser
65              70                  75

<210> SEQ ID NO 44
<211> LENGTH: 77
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 44

Gly Thr Arg Thr Glu Tyr Leu Lys Lys Leu Ala Glu Glu Ala Lys Glu
1               5                   10                  15

Leu Ala Lys Arg Ser Arg Glu Leu Ser Lys Glu Ser Arg Arg Leu Ser
            20                  25                  30

Glu Glu Ala Arg Arg Asp Pro Asp Lys Glu Lys Leu Leu Arg Val Val
            35                  40                  45

Lys Lys Leu Gln Glu Val Ile Glu Glu Leu Gln Arg Val Ile Glu Glu
        50                  55                  60

Leu Leu Arg Val Ile Lys Glu Ala Leu Glu Asn Gln Ser
65              70                  75

<210> SEQ ID NO 45
<211> LENGTH: 77
<212> TYPE: PRT
<213> ORGANISM: Artificial Sequence

```
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 45

Gly Thr Glu Thr Glu Tyr Gln Arg Glu Leu Ala Arg Glu Ala Arg Arg
1               5                   10                  15

Leu Ala Lys Arg Ser Arg Glu Leu Ser Glu Arg Ser Arg Lys Leu Ser
            20                  25                  30

Glu Asp Ala Lys Arg Asp Pro Asp Lys Asp Lys Leu Leu Glu Val Val
        35                  40                  45

Glu Arg Leu Gln Gln Val Ile Glu Glu Leu Gln Lys Val Ile Glu Glu
    50                  55                  60

Leu Leu Arg Val Ile Glu Ser Ser Leu Lys Thr Ile Ser
65                  70                  75

<210> SEQ ID NO 46
<211> LENGTH: 77
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 46

Gly Thr Ser Asp Tyr Ile Ile Glu Gln Ile Gln Arg Asp Gln Glu Glu
1               5                   10                  15

Ala Arg Lys Lys Val Glu Glu Ala Glu Glu Arg Leu Glu Arg Val Lys
            20                  25                  30

Glu Ala Ser Lys Arg Gly Val Ser Ser Asp Gln Leu Leu Asp Leu Ile
        35                  40                  45

Arg Glu Leu Ala Glu Ile Ile Glu Glu Leu Ile Arg Ile Ile Arg Arg
    50                  55                  60

Ser Asn Glu Ala Ile Lys Glu Leu Ile Lys Asn Gln Ser
65                  70                  75

<210> SEQ ID NO 47
<211> LENGTH: 77
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 47

Gly Thr Glu Glu Tyr Arg Arg Lys Glu Gln Glu Glu Arg Thr Lys Glu
1               5                   10                  15

Gln Gln Glu Arg Thr Glu Arg Gln Arg Lys Thr Glu Glu Leu Lys
            20                  25                  30

Arg Ala Thr Lys Glu Gly Thr Leu Thr Pro Glu Glu Ala Ile Arg Gln
        35                  40                  45

Ala Gln Lys Gln Ser Glu Asn Ala Glu Arg Gln Ser Arg Glu Ala Glu
    50                  55                  60
```

Lys Gln Ser Arg Glu Ala Asn Glu Ala Leu Arg Lys Arg
65                  70                  75

<210> SEQ ID NO 48
<211> LENGTH: 77
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 48

Gly Ser Glu Asp Tyr Lys Leu Arg Glu Ala Gln Arg Glu Leu Asp Lys
1               5                   10                  15

Gln Arg Lys Asp Thr Glu Glu Ile Arg Lys Arg Leu Lys Glu Ile Gln
                20                  25                  30

Arg Leu Thr Asp Glu Arg Thr Ser Thr Ala Asp Glu Leu Ile Lys Glu
            35                  40                  45

Leu Arg Glu Ile Ile Arg Arg Leu Gln Glu Gln Ser Glu Lys Leu Arg
        50                  55                  60

Glu Ile Ile Glu Glu Leu Glu Lys Ile Ile Arg Lys Arg
65                  70                  75

<210> SEQ ID NO 49
<211> LENGTH: 77
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 49

Gly Ser Glu Asp Tyr Lys Leu Lys Glu Leu Gln Lys Arg Asn Lys Lys
1               5                   10                  15

Gln Glu Glu Glu Ala Lys Arg Asn Asp Asp Arg Lys Lys Ile Glu
                20                  25                  30

Glu Leu Thr Arg Lys Arg Thr Ser Thr Ala Asp Glu Leu Ile Arg Glu
            35                  40                  45

Leu Gln Arg Ser Asn Glu Glu Met Gln Arg Ser Gln Arg Glu Met Gln
        50                  55                  60

Asp Gln Ser Arg Arg Leu Glu Asp Ile Ile Arg Lys Arg
65                  70                  75

<210> SEQ ID NO 50
<211> LENGTH: 77
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 50

Gly Thr Glu Asp Tyr Lys Arg Arg Glu Ala Glu Arg Lys Leu Gln Lys
1               5                   10                  15

Gln Gln Glu Glu Leu Lys Glu Leu Lys Arg Lys Leu Glu Glu Ile Arg

```
                     20                  25                  30

Glu Leu His Glu Lys Gly Val Gly Ser Pro Asp Arg Leu Ile Arg Glu
             35                  40                  45

Leu Glu Arg Ile Ile Arg Glu Leu Gln Arg Met Gln Lys Glu Asn Glu
         50                  55                  60

Lys Ile Ile Lys Glu Leu Gln Arg Ile Ile Lys Lys Arg
 65                  70                  75

<210> SEQ ID NO 51
<211> LENGTH: 85
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 51

Gly Thr Glu Ser Lys Tyr Leu Leu Glu Glu Ala Arg Arg Leu Lys Asp
 1               5                  10                  15

Glu Ala Arg Lys Leu Lys Glu Glu Ala Lys Lys Val Lys Glu Glu Ser
             20                  25                  30

Arg Lys Leu Ile Glu Arg Ile Asp Arg Gly Glu Asp Ser Asp Arg Glu
         35                  40                  45

Leu Leu Glu Arg Leu Lys Glu Gln Asn Asn Arg Leu Leu Glu Ile Ile
     50                  55                  60

Glu Arg Leu Leu Glu Ile Ile Glu Arg Leu Leu Lys Leu Ile Glu Glu
 65                  70                  75                  80

Trp Thr Arg Asp Ser
             85

<210> SEQ ID NO 52
<211> LENGTH: 85
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 52

Gly Thr Glu Glu Asp Tyr Ala Glu Arg Glu Ile Arg Lys Met Lys Glu
 1               5                  10                  15

Glu Gln Lys Arg Gln Arg Lys Arg Leu Glu Glu Leu Glu Arg Glu Leu
             20                  25                  30

Gln Glu Met Gln Glu Lys Lys Arg Glu Gly Thr Ser Asp Ala Lys Glu
         35                  40                  45

Val Ile Asp Gln Leu Glu Arg Ile Ile Arg Glu Leu Gln Glu Ile Ile
     50                  55                  60

Arg Ser Gln Glu Asp Ile Thr Arg Lys Leu Glu Glu Ile Ile Arg Arg
 65                  70                  75                  80

Met Lys Glu Asn Ser
             85

<210> SEQ ID NO 53
<211> LENGTH: 77
<212> TYPE: PRT
```

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 53

Gly Thr Asn Lys Glu Glu Leu Lys Arg Thr Met Glu Glu Gln Gln Arg
1               5                   10                  15

Ile Leu Glu Lys Leu Leu Arg Thr Ile Lys Glu Gln Lys Glu Ile Leu
                20                  25                  30

Arg Lys Gln Glu Glu Gly Arg Ala Thr Lys Glu Leu Lys Arg Leu
        35                  40                  45

Thr Lys Leu Ala Gln Glu Gln Glu Arg Met Met Arg Glu Leu Ile Asp
    50                  55                  60

Leu Ala Arg Lys Gln Ala Tyr Leu Leu Lys Arg Glu Ser
65                  70                  75

<210> SEQ ID NO 54
<211> LENGTH: 77
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 54

Gly Thr Arg Glu Glu Lys Ile Arg Arg Ile Leu Glu Glu Ile Gln Lys
1               5                   10                  15

Ile Met Glu Glu Ile Lys Arg Ile Met Glu Glu Ile Lys Arg Thr Gln
                20                  25                  30

Glu Glu Ala Glu Lys His Gly Ser Ser Lys Lys Ala Ile Glu Lys Gln
        35                  40                  45

Lys Glu Leu Leu Arg Arg Leu Glu Glu Leu Leu Arg Lys Leu Glu Arg
    50                  55                  60

Leu Leu Arg Glu Leu Glu Tyr Leu Met Arg Asp Glu Lys
65                  70                  75

<210> SEQ ID NO 55
<211> LENGTH: 77
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 55

Gly Thr Arg Glu Glu Trp Leu Tyr Arg Ile Leu Glu Leu Ile Glu Arg
1               5                   10                  15

Ile Glu Arg Leu Ile Lys Glu Ile Glu Arg Leu Ser Arg Arg Ala Leu
                20                  25                  30

Glu Leu Leu Glu Asn Asn Ala Ser Asn Glu Glu Trp Ala Gln Glu Ile
        35                  40                  45

Lys Glu Met Gln Arg Lys Ile Gln Glu Trp Leu Lys Gln Ile Leu Glu
    50                  55                  60
```

```
Trp Leu Lys Lys Ile Lys Glu Trp Ile Arg Glu Ser Gln
65                  70                  75
```

<210> SEQ ID NO 56
<211> LENGTH: 76
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 56

```
Gly Thr Arg Thr Glu Ile Ile Arg Glu Leu Glu Arg Ser Leu Arg Glu
1               5                   10                  15

Gln Glu Glu Leu Ala Lys Arg Leu Lys Glu Leu Leu Arg Glu Leu Glu
                20                  25                  30

Arg Leu Gln Arg Glu Gly Ser Ser Asp Glu Asp Val Arg Glu Leu Leu
            35                  40                  45

Arg Glu Ile Lys Glu Leu Val Glu Glu Ile Glu Lys Leu Ala Arg Glu
        50                  55                  60

Gln Lys Tyr Leu Val Glu Glu Leu Lys Arg Gln Asp
65                  70                  75
```

<210> SEQ ID NO 57
<211> LENGTH: 77
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 57

```
Gly Thr Asp Thr Asp Glu Leu Leu Arg Leu Ala Lys Glu Gln Ala Glu
1               5                   10                  15

Leu Leu Lys Glu Ile Lys Lys Leu Val Glu Glu Ile Ala Arg Leu Val
                20                  25                  30

Lys Glu Ile Gln Glu Asp Pro Ser Asp Glu Leu Leu Lys Thr Leu Ala
            35                  40                  45

Glu Leu Val Arg Lys Leu Lys Glu Leu Val Asp Met Glu Arg Ser
        50                  55                  60

Met Lys Glu Gln Leu Tyr Ile Ile Lys Lys Gln Lys Ser
65                  70                  75
```

<210> SEQ ID NO 58
<211> LENGTH: 85
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 58

```
Gly Thr Glu Glu Thr Lys Asn Ser Lys Arg Val Leu Asp Ile Ile Glu
1               5                   10                  15
```

Glu Leu Met Arg Gln Val Glu Glu Asn Ser Arg Glu Leu Glu Lys Arg
            20                  25                  30

Ile Lys Glu Leu Leu Arg Gln Thr Lys Glu Gly Lys Thr Lys Lys Glu
        35                  40                  45

Leu Glu Arg Asp Val Arg Arg Thr Ile Glu Glu Gln Lys Lys Glu Leu
50                      55                  60

Arg Arg Leu Lys Glu Gln Val Arg Lys Thr Lys Glu Glu Gln Arg Glu
65                  70                  75                  80

Glu Gln Tyr Arg Ser
            85

<210> SEQ ID NO 59
<211> LENGTH: 85
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 59

Gly Thr Arg Thr Glu Lys Leu Met Lys Glu Val Glu Glu Ile Gln Arg
1               5                   10                  15

Arg Gln Ile Glu Leu Leu Lys Lys Leu Met Lys Glu Val Glu Asp Ser
            20                  25                  30

Ser Lys Arg Asn Gln Glu Ala Thr Glu Arg Gly Thr Thr Lys Lys Lys
        35                  40                  45

Trp Lys Glu Glu Gln Glu Lys Ile Leu Glu Asp Leu Lys Arg Glu Val
50                  55                      60

Arg Arg Ile Ile Glu Glu Ser Arg Lys Trp Leu Glu Asp Leu Lys Lys
65                  70                  75                  80

Lys Val Tyr Glu Ser
            85

<210> SEQ ID NO 60
<211> LENGTH: 85
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 60

Gly Thr Glu Lys Tyr Arg Leu Arg Glu Glu Val Arg Arg Thr Ile Glu
1               5                   10                  15

Glu Gln Lys Glu Asn Leu Glu Arg Leu Lys Gln Glu Val Lys Glu Thr
            20                  25                  30

Glu Arg Lys Thr Glu Glu Trp Arg Glu Arg Asn Thr Thr Glu Glu Asp
        35                  40                  45

Ala Gln Arg Glu Gln Ile Lys Ile Ile Arg Arg Leu Met Lys Glu Val
50                  55                      60

Glu Arg Asn Ser Arg Arg Leu Glu Lys Glu Leu Arg Arg Leu Val Glu
65                  70                  75                  80

Glu Thr Arg Glu Ser
            85

```
<210> SEQ ID NO 61
<211> LENGTH: 85
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 61

Gly Thr Glu Lys Tyr Arg Leu Ile Arg Glu Ser Glu Arg Ala Leu Arg
1               5                  10                  15

Glu Leu Lys Arg Lys Val Arg Glu Leu Glu Asp Gln Arg Glu Arg
            20                  25                  30

Leu Asp Glu Gln Arg Lys Lys Val Glu Glu Gly Gln Thr Thr Asp Glu
        35                  40                  45

Leu Leu Arg Gln Asn Glu Glu Asn Ser Arg Arg Met Leu Lys Glu Thr
    50                  55                  60

Lys Lys Leu Leu Arg Glu Ile Glu Arg Ile Gln Arg Glu Gln Gln Arg
65                  70                  75                  80

Gln Asn Gln Glu Asn
                85

<210> SEQ ID NO 62
<211> LENGTH: 85
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 62

Gly Thr Glu Lys Glu Lys Glu Ile Glu Lys Asn Ser Arg Glu Val Ile
1               5                  10                  15

Lys Gln Val Glu Asp Ile Leu Arg Glu Ile Lys Glu Asn Ser Lys Arg
            20                  25                  30

Asn Ile Glu Ile Ile Lys Glu Leu Gln Lys Asp Pro Ser Asp Glu Lys
        35                  40                  45

Met Arg Glu Thr Ile Glu Gln Gln Arg Glu Asn Leu Glu Arg Leu Glu
    50                  55                  60

Arg Lys Ala Arg Glu Leu Ile Arg Arg Gln Arg Asn Leu Arg Glu
65                  70                  75                  80

Thr Gln Tyr Lys Asp
                85

<210> SEQ ID NO 63
<211> LENGTH: 85
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 63

Gly Thr Glu Lys Tyr Arg Ile Ile Glu Glu Gln Arg Arg Asn Leu Glu
```

```
                1               5                  10                  15
Asp Leu Glu Arg Glu Ile Arg Glu Ile Ile Lys Lys Leu Lys Glu Ala
                    20                  25                  30

Leu Glu Arg Leu Arg Glu Leu Val Glu Arg Asn Ser Thr Asn Asp Arg
            35                  40                  45

Leu Leu Asp Glu Val Arg Lys Ile Ile Glu Glu Ala Ile Glu Asp Met
        50                  55                  60

Lys Arg Leu Leu Glu Lys Val Glu Arg Ser Ile Arg Gln Asn Ile Glu
65                  70                  75                  80

Glu Leu Arg Arg Ser
                85
```

<210> SEQ ID NO 64
<211> LENGTH: 85
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 64

```
Gly Thr Asn Lys Glu Tyr Leu Arg Arg Lys Val Lys Glu Leu Lys Asp
1               5                  10                  15

Gln Gln Lys Arg Asn Leu Glu Glu Leu Glu Arg Glu Val Arg Arg Leu
            20                  25                  30

Ile Lys Glu Ile Glu Glu Trp Arg Glu Arg Asn Thr Thr Thr Asp Arg
        35                  40                  45

Ala Leu Lys Glu Ile Ile Arg Gln Ile Gln Arg Leu Leu Glu Glu Ala
        50                  55                  60

Arg Arg Asn Ser Glu Glu Val Leu Arg Gln Ile Glu Glu Ile Met Glu
65                  70                  75                  80

Glu Thr Arg Glu Ser
                85
```

<210> SEQ ID NO 65
<211> LENGTH: 85
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 65

```
Gly Thr Glu Glu Arg Ala Leu Glu Arg Ile Ile Arg Ala Ile Arg
1               5                  10                  15

Glu Leu Met Arg Glu Val Glu Arg Asn Ser Lys Glu Val Leu Gln Trp
            20                  25                  30

Ile Lys Glu Met Leu Arg Leu Thr Lys Glu Asn Ser Ser Thr Lys Glu
        35                  40                  45

Leu Glu Glu Arg Trp Arg Glu Ile Glu Glu Arg Gln Arg Arg Asn Leu
        50                  55                  60

Glu Lys Leu Lys Glu Glu Val Arg Arg Leu Glu Asp Glu Ile Arg Gln
65                  70                  75                  80

Glu Thr Tyr Arg Ser
```

```
<210> SEQ ID NO 66
<211> LENGTH: 85
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: optionally absent

<400> SEQUENCE: 66
```

Gly Thr Glu Thr Lys Lys Leu Val Glu Val Glu Arg Ala Leu Arg
 1               5                  10                  15

Glu Leu Leu Lys Thr Ser Glu Asp Leu Val Arg Lys Val Glu Lys Ala
                20                  25                  30

Leu Arg Glu Leu Leu Glu Leu Ile Arg Arg Gly Gly Thr Lys Asp Lys
            35                  40                  45

Ile Glu Glu Lys Ile Arg Arg Val Leu Glu Ile Lys Arg Glu Leu
 50                  55                  60

Glu Arg Gln Lys Arg Lys Ile Glu Asp Val Leu Arg Gln Ile Lys Glu
 65                  70                  75                  80

Glu Leu Tyr Arg Ser
                85

```
<210> SEQ ID NO 67
<211> LENGTH: 111
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (110)..(111)
<223> OTHER INFORMATION: optionally absent

<400> SEQUENCE: 67
```

Ser Asp Tyr Leu Arg Leu Ala Thr Glu His Asn Lys Leu Ala Val Glu
 1               5                  10                  15

Ala Asn Arg Leu Ala Ile Glu Leu Ala Lys Ser Ala Val Glu Leu Ala
                20                  25                  30

Glu Thr Asp Pro Ser Lys Thr Ala Leu Glu His Ala Glu Leu Ala Ala
                35                  40                  45

Arg Leu Leu Glu Met Met Val Gln Phe Thr Lys Ala Ala Gln Glu Leu
 50                  55                  60

Thr Arg Glu Ala Ile Arg Lys Glu Gly Arg Asn Glu Glu Ser Glu Lys
 65                  70                  75                  80

Val Leu Arg Lys Ser Lys Glu Ala Tyr Lys Glu Ser Glu Lys Ala Leu
                85                  90                  95

Glu Asp Ala Arg Arg Leu Leu Asp Glu Leu Arg Lys Lys Gly Ser
                100                 105                 110

```
<210> SEQ ID NO 68
<211> LENGTH: 111
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (110)..(111)
```

<223> OTHER INFORMATION: optionally absent

<400> SEQUENCE: 68

Ser Glu Glu Leu Arg Lys Ala Ala Glu Asn Glu Leu Ala Val Arg
1               5                   10                  15

Leu Ala Glu Ala Ala Leu Arg Met Ala Arg Ser Ala Leu His Leu Phe
            20                  25                  30

Glu Glu Asn Pro Ser Asp Glu Met Leu Lys Phe Leu Glu Leu Ala Met
        35                  40                  45

Glu Val Ala Lys Met Ala Ala Glu Leu Leu Lys Ala Ser Leu Lys Met
    50                  55                  60

Leu Lys Lys Ala Ala Glu Glu Arg Gly Ser Asp Glu Ser Val Lys Tyr
65                  70                  75                  80

Leu Ala Asp Lys Ser Arg Asp Ile Met Arg Gln Ile Thr Glu Leu
                85                  90                  95

Lys Lys Leu Glu Glu Glu Ala Lys Arg Ala Gln Lys Arg Gly Ser
            100                 105                 110

<210> SEQ ID NO 69
<211> LENGTH: 112
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (111)..(112)
<223> OTHER INFORMATION: optionally absent

<400> SEQUENCE: 69

Ser Glu Lys Ala Arg Ile Ala Val Glu Asn Leu Glu Ala Ala Leu Arg
1               5                   10                  15

Leu Asn Arg Ala Ala Ala Glu Met Gln Lys Ser Ala Ile Lys Ile Met
            20                  25                  30

Asp Asp Asn Arg Ser Asp Glu Lys Ala Leu Arg Tyr Leu Arg Leu Thr
        35                  40                  45

Thr Lys Val Leu Arg Met Ser Val Glu Leu Leu Arg Ala Ser Leu Glu
    50                  55                  60

Leu Ala Glu Lys Ala Leu Arg Glu Gly Ser Asp Asp Ser Ala Glu
65                  70                  75                  80

Lys Val Arg Lys Glu Ala Glu Ile Leu Lys Glu Ser Thr Glu Ile
                85                  90                  95

Leu Lys Glu Ala Asp Lys Glu Thr Lys Arg Ala Asp Glu Glu Gly Ser
            100                 105                 110

<210> SEQ ID NO 70
<211> LENGTH: 112
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (111)..(112)
<223> OTHER INFORMATION: optionally absent

<400> SEQUENCE: 70

Ser Arg Arg Leu Glu Leu Ala Ala Arg Ile Asn Lys Ala Ala Ala Glu
1               5                   10                  15

Asn Ala Arg Ser Ala Ile Glu Ile Gln Glu Leu Ala Ala Arg Leu Ala
            20                  25                  30

```
Asp Glu Leu Ser Ser Lys Lys Val Ile Asp Phe Ala Arg Ala Thr
            35                  40                  45

Thr Glu Val Leu Arg Met Ser Val Lys Leu Leu Lys Leu Ser Leu Glu
 50                  55                  60

Met Leu Glu Glu Ala Ala Arg Gln Asp Gly Arg Ser Glu Glu Val Arg
 65                  70                  75                  80

Tyr Leu Ala Glu Ser Lys Lys Ile Leu Glu Glu Ala Arg Lys Ala
                85                  90                  95

Leu Glu Asp Ala Asp Arg Leu Thr Lys Arg Ile Glu Glu Gly Ser
                100                 105                 110

<210> SEQ ID NO 71
<211> LENGTH: 112
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (111)..(112)
<223> OTHER INFORMATION: optionally absent

<400> SEQUENCE: 71

Thr Asp Val Leu Arg Ile Ala Ala Glu Asn Leu Lys Ala Ala Val Glu
 1               5                  10                  15

Leu Ala Lys Ala Ala Leu Glu Met Ala Lys Ser Ala Ile Glu Ile Ala
                20                  25                  30

Lys Thr Leu Thr Glu Asp Asp Glu Ala Leu Lys Phe Ala Arg Ala Ala
            35                  40                  45

Ala Glu Val Leu Arg Met Ala Ala Lys Leu Leu Lys Leu Ser Ile Glu
 50                  55                  60

Leu Ala Arg Lys Ala Ala Glu Glu Gly Ser Asp Asp Glu Val Arg
 65                  70                  75                  80

Tyr Ile Leu Asp Glu Ala Arg Lys Gln Ala Asp Glu Leu Arg Glu Ala
                85                  90                  95

Leu Lys Lys Val Asp Glu Ile Met Lys Glu Leu Asp Lys Arg Gly Ser
                100                 105                 110

<210> SEQ ID NO 72
<211> LENGTH: 70
<212> TYPE: PRT
<213> ORGANISM: Artificial Sequence
<220> FEATURE:
<223> OTHER INFORMATION: Synthetic

<400> SEQUENCE: 72

Thr Arg Arg Lys Gln Glu Met Lys Arg Leu Lys Tyr Glu Met Glu Lys
 1               5                  10                  15

Ile Arg Glu Glu Thr Glu Glu Val Lys Lys Gly Ile Glu Glu Ser Lys
                20                  25                  30

Lys Arg Pro Gln Ser Glu Ser Ala Lys Asn Leu Ile Leu Ile Met Gln
            35                  40                  45

Leu Leu Ile Asn Gln Ile Arg Leu Leu Ala Leu Gln Ile Arg Met Leu
 50                  55                  60

Ala Leu Gln Leu Gln Glu
 65                  70

<210> SEQ ID NO 73
<211> LENGTH: 70
```

-continued

```
<212> TYPE: PRT
<213> ORGANISM: Artificial Sequence
<220> FEATURE:
<223> OTHER INFORMATION: Synthetic

<400> SEQUENCE: 73

Thr Glu Asp Gln Glu Arg Leu Arg Lys Gln Met Glu Tyr Glu Arg Lys
1               5                   10                  15

His Thr Glu Lys Val Glu Lys Glu Ile Arg Lys Val Glu Gln Lys Met
            20                  25                  30

Lys Ser His Glu Asp Thr Ser Leu Arg Leu Leu Val Leu Ile Ala Arg
        35                  40                  45

Leu Leu Ile Asn Gln Ile Arg Leu Leu Ile Leu Gln Ile Arg Ser Leu
    50                  55                  60

Ser Asn Leu Glu Arg Asn
65                  70

<210> SEQ ID NO 74
<211> LENGTH: 71
<212> TYPE: PRT
<213> ORGANISM: Artificial Sequence
<220> FEATURE:
<223> OTHER INFORMATION: Synthetic

<400> SEQUENCE: 74

Thr Glu Ser Thr Leu Leu Ile Leu Ile Met Arg Leu Leu Val Gln Gln
1               5                   10                  15

Ser Glu Leu Leu Gln Leu Gln Ile Gln Met Leu Gln Leu Leu Leu Lys
            20                  25                  30

Ala Asn Asn Gly Thr Asn Lys Thr Glu Ile Glu Arg Arg Ser Lys Glu
        35                  40                  45

Met Glu Glu Glu Leu Lys Arg Met Lys Glu Ser Asn Arg Glu Met Thr
    50                  55                  60

Lys Arg Ile Lys Glu Met Glu
65                  70

<210> SEQ ID NO 75
<211> LENGTH: 71
<212> TYPE: PRT
<213> ORGANISM: Artificial Sequence
<220> FEATURE:
<223> OTHER INFORMATION: Synthetic

<400> SEQUENCE: 75

Thr Glu Ser Asp Leu Leu Arg Gln Ile Ser Lys Leu Leu Ile Ile Gln
1               5                   10                  15

Ile Arg Leu Leu Leu Leu Gln Ile Gln Met Leu Ile Leu Leu Leu Lys
            20                  25                  30

Met Asn Thr Gly Thr Asn Thr Thr Gln Ile Thr Lys Glu Ala Lys Arg
        35                  40                  45

Ile Glu Lys Glu Ala Gln Glu Ala Arg Lys Glu Leu Glu Lys Met Gln
    50                  55                  60

Glu Ser Asn Lys Lys Gln Thr
65                  70

<210> SEQ ID NO 76
<211> LENGTH: 72
<212> TYPE: PRT
<213> ORGANISM: Artificial Sequence
<220> FEATURE:
<223> OTHER INFORMATION: Synthetic
```

```
<400> SEQUENCE: 76

Thr Glu Asp Glu Ile Arg Lys Leu Arg Lys Leu Leu Glu Glu Ala Glu
1               5                   10                  15

Lys Lys Leu Tyr Lys Leu Glu Asp Lys Thr Arg Arg Ser Glu Glu Ile
                20                  25                  30

Ser Lys Thr Asp Asp Pro Lys Ala Gln Ser Leu Gln Leu Ile Ala
        35                  40                  45

Glu Ser Leu Met Leu Ile Ala Glu Ser Leu Leu Ile Ile Ala Ile Ser
    50                  55                  60

Leu Leu Leu Ser Ser Arg Asn Gly
65                  70

<210> SEQ ID NO 77
<211> LENGTH: 72
<212> TYPE: PRT
<213> ORGANISM: Artificial Sequence
<220> FEATURE:
<223> OTHER INFORMATION: Synthetic

<400> SEQUENCE: 77

Thr Glu Asp Glu Leu Gln Arg Val Glu Glu Ile Arg Glu Leu
1               5                   10                  15

Glu Arg Lys Ala Lys Glu Leu His Tyr Lys Ser Glu Glu Ile Arg Lys
                20                  25                  30

Lys Val Asn Gly Arg Ser Pro Gln Ala Glu Ala Leu Leu Met Ile Ala
        35                  40                  45

Gln Ala Leu Leu Asn Ile Ser Glu Ser Leu Leu Ala Ile Ala Lys Ala
    50                  55                  60

Leu Leu Met Ile Ala Arg Ser Thr
65                  70

<210> SEQ ID NO 78
<211> LENGTH: 70
<212> TYPE: PRT
<213> ORGANISM: Artificial Sequence
<220> FEATURE:
<223> OTHER INFORMATION: Synthetic

<400> SEQUENCE: 78

Thr Asp Glu Arg Glu Ile Ile Lys Arg Val Lys Arg Leu Leu Glu Glu
1               5                   10                  15

Val Glu Tyr Leu Ile Glu Arg Leu Arg Asp Gln Ile Glu Lys Ala Glu
                20                  25                  30

Lys Gly Leu Leu Asp Ser Arg Lys Ala Gln Gln Asn Ala Glu Ala Leu
        35                  40                  45

Val Asn Leu Ile Lys Ala Met Val Leu Val Leu Lys Ala Leu Leu Leu
    50                  55                  60

Ala Lys Glu Leu Glu Arg
65                  70

<210> SEQ ID NO 79
<211> LENGTH: 70
<212> TYPE: PRT
<213> ORGANISM: Artificial Sequence
<220> FEATURE:
<223> OTHER INFORMATION: Synthetic

<400> SEQUENCE: 79

Thr Glu Glu Gln Tyr Ile Ile Glu Glu Val Lys Lys Leu Leu Glu Glu
```

```
                1               5                  10                  15
Val Lys Lys Leu Ile Glu Glu Leu Lys Lys Gln Ile Glu Lys Ala Glu
                20                  25                  30

Lys Gly Glu Glu Asp Ser Arg Lys Ala Gln Gln Asn Ala Glu Ala Leu
            35                  40                  45

Val Asn Leu Ile Lys Ala Met Val Leu Val Leu Lys Ala Leu Leu Leu
    50                  55                  60

Ala Lys Glu Leu Glu Arg
65              70

<210> SEQ ID NO 80
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa can be R, K, E, D, S, T, N, Q, Y, or A.

<400> SEQUENCE: 80

Xaa Xaa Xaa
1

<210> SEQ ID NO 81
<211> LENGTH: 13
<212> TYPE: PRT
<213> ORGANISM: Artificial Sequence
<220> FEATURE:
<223> OTHER INFORMATION: Synthetic

<400> SEQUENCE: 81

Arg Leu Gln Arg Glu Gly Ser Ser Asp Glu Asp Val Arg
1               5                   10

<210> SEQ ID NO 82
<211> LENGTH: 7
<212> TYPE: PRT
<213> ORGANISM: Artificial Sequence
<220> FEATURE:
<223> OTHER INFORMATION: Synthetic

<400> SEQUENCE: 82

Arg Ser Leu Arg Glu Gln Glu
1               5

<210> SEQ ID NO 83
<211> LENGTH: 7
<212> TYPE: PRT
<213> ORGANISM: Artificial Sequence
<220> FEATURE:
<223> OTHER INFORMATION: Synthetic

<400> SEQUENCE: 83

Glu Ile Ile Arg Glu Leu Glu
1               5
```

```
<210> SEQ ID NO 84
<211> LENGTH: 7
<212> TYPE: PRT
<213> ORGANISM: Artificial Sequence
<220> FEATURE:
<223> OTHER INFORMATION: Synthetic

<400> SEQUENCE: 84

Glu Leu Leu Arg Glu Leu Glu
1               5

<210> SEQ ID NO 85
<211> LENGTH: 7
<212> TYPE: PRT
<213> ORGANISM: Artificial Sequence
<220> FEATURE:
<223> OTHER INFORMATION: Synthetic

<400> SEQUENCE: 85

Glu Leu Ala Lys Arg Leu Lys
1               5

<210> SEQ ID NO 86
<211> LENGTH: 7
<212> TYPE: PRT
<213> ORGANISM: Artificial Sequence
<220> FEATURE:
<223> OTHER INFORMATION: Synthetic

<400> SEQUENCE: 86

Lys Leu Ala Arg Glu Gln Lys
1               5

<210> SEQ ID NO 87
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is Y or E

<400> SEQUENCE: 87

Xaa Leu Val Glu Glu Leu Lys
1               5

<210> SEQ ID NO 88
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is Y or E

<400> SEQUENCE: 88

Xaa Leu Leu Arg Glu Ile Lys
1               5

<210> SEQ ID NO 89
<211> LENGTH: 7
<212> TYPE: PRT
<213> ORGANISM: Artificial Sequence
<220> FEATURE:
<223> OTHER INFORMATION: Synthetic
```

```
<220> FEATURE:
<221> NAME/KEY: MISC_FEATURE
<222> LOCATION: (1)..(1)
<223> OTHER INFORMATION: X is Y or E

<400> SEQUENCE: 89

Xaa Leu Val Glu Glu Ile Glu
1               5

<210> SEQ ID NO 90
<211> LENGTH: 7
<212> TYPE: PRT
<213> ORGANISM: Artificial Sequence
<220> FEATURE:
<223> OTHER INFORMATION: Synthetic

<400> SEQUENCE: 90

Glu Leu Val Glu Glu Leu Lys
1               5

<210> SEQ ID NO 91
<211> LENGTH: 7
<212> TYPE: PRT
<213> ORGANISM: Artificial Sequence
<220> FEATURE:
<223> OTHER INFORMATION: Synthetic

<400> SEQUENCE: 91

Glu Leu Leu Arg Glu Ile Lys
1               5

<210> SEQ ID NO 92
<211> LENGTH: 7
<212> TYPE: PRT
<213> ORGANISM: Artificial Sequence
<220> FEATURE:
<223> OTHER INFORMATION: Synthetic

<400> SEQUENCE: 92

Glu Leu Val Glu Glu Ile Glu
1               5

<210> SEQ ID NO 93
<211> LENGTH: 38
<212> TYPE: PRT
<213> ORGANISM: Artificial Sequence
<220> FEATURE:
<223> OTHER INFORMATION: Synthetic

<400> SEQUENCE: 93

Ser Ser Asp Tyr Leu Arg Glu Thr Ile Glu Glu Leu Arg Glu Arg Ile
1               5                   10                  15

Arg Glu Leu Glu Arg Glu Ile Arg Arg Ser Asn Glu Glu Ile Glu Arg
            20                  25                  30

Leu Arg Glu Glu Lys Ser
        35

<210> SEQ ID NO 94
<211> LENGTH: 34
<212> TYPE: PRT
<213> ORGANISM: Artificial Sequence
<220> FEATURE:
<223> OTHER INFORMATION: Synthetic

<400> SEQUENCE: 94

Thr Glu Arg Glu Asn Asn Tyr Arg Asn Glu Glu Asn Asn Arg Lys Ile
```

-continued

```
1               5              10              15
Glu Glu Glu Ile Arg Glu Ile Lys Lys Glu Ile Lys Lys Asn Lys Glu
                20              25              30
Arg Asp
```

.

POLYPEPTDES CAPABLE OF FORMING HOMO-OLIGOMERS WITH MODULAR HYDROGEN BOND NETWORK-MEDIATED SPECIFICITY AND THEIR DESIGN

RELATED APPLICATION

This application is a U.S. national phase of International Application No. PCT/US2017/025532, filed on Mar. 31, 2017, which claims priority to U.S. Provisional Application No. 62/317,190, filed Apr. 1, 2016, both of which are incorporated by reference herein in their entirety.

BACKGROUND

Hydrogen bonds play key roles in the structure, function, and interaction specificity of biomolecules. There are two main challenges facing do novo design of hydrogen bonding interactions: first, hydrogen bonding atoms are geometrically restricted to narrow ranges of orientation and distance, and second, nearly all polar atoms must participate in hydrogen bonds either with other macromolecular polar atoms, or with solvent—if not, there is a considerable energetic penalty associated with stripping away water upon folding or binding. The DNA double helix elegantly resolves both challenges; paired bases come together such that all buried polar atoms make hydrogen bonds that are self-contained between the two bases and have near ideal geometry. In proteins, meeting these challenges is more complicated because backbone geometry is highly variable and pairs of polar amino acids cannot generally interact as to fully satisfy their mutual hydrogen bonding capabilities; hence sidechain hydrogen bonding usually involves networks of multiple amino acids with variable geometry and composition, and there are generally very different networks at different sites within a single protein or interface pre-organizing polar residues for binding and catalysis.

SUMMARY OF THE INVENTION

In nature, structural specificity in DNA and proteins is encoded quite differently: in DNA, specificity arises from modular hydrogen bonds in the core of the double helix, whereas in proteins, specificity arises largely from buried hydrophobic packing complemented by irregular peripheral polar interactions. Herein is described a general approach for designing a wide range of protein homo-oligomers with specificity determined by modular arrays of central hydrogen bond networks. This approach can be used to design dimers, trimers, and tetramers comprising two concentric rings of helices, including previously not seen triangular, square, and supercoiled topologies. X-ray crystallography confirms that the structures overall, and the hydrogen bond networks in particular, are nearly identical to the design models, and the networks confer interaction specificity in vivo. The ability to design extensive hydrogen bond networks with atomic accuracy is a milestone for protein design and enables the programming of protein interaction specificity for a broad range of synthetic biology applications. Also described herein is a class of protein oligomers with regular arrays of hydrogen bond networks that enable programming of interaction specificity.

In one aspect, a method is provided. A computing device determines a search space for hydrogen bond networks related to one or more molecules. The search space includes a plurality of energy terms related to a plurality of residues related to the hydrogen bond networks. The computing device searches the search space to identify one or more hydrogen bond networks based on the plurality of energy terms. The computing device screens the identified one or more hydrogen bond networks to identify one or more screened hydrogen bond networks based on scores for the one or more identified hydrogen bond networks. The computing device generates an output related to the one or more screened hydrogen bond networks.

In another aspect, a computing device is provided. The computing device includes one or more data processors and a computer-readable medium. The computer-readable medium is configured to store at least computer-readable instructions that, when executed, cause the computing device to perform functions. The functions include: determining a search space for hydrogen bond networks related to one or more molecules, where the search space includes a plurality of energy terms related to a plurality of residues related to the hydrogen bond networks; searching the search space to identify one or more hydrogen bond networks based on the plurality of energy terms; screening the identified one or more hydrogen bond networks to identify one or more screened hydrogen bond networks based on scores for the one or more identified hydrogen bond networks; and generating an output related to the one or more screened hydrogen bond networks.

In another aspect, a computer-readable medium is provided. The computer-readable medium is configured to store at least computer-readable instructions that, when executed by one or more processors of a computing device, cause the computing device to perform functions. The functions include: determining a search space for hydrogen bond networks related to one or more molecules, where the search space includes a plurality of energy terms related to a plurality of residues related to the hydrogen bond networks; searching the search space to identify one or more hydrogen bond networks based on the plurality of energy terms; screening the identified one or more hydrogen bond networks to identify one or more screened hydrogen bond networks based on scores for the one or more identified hydrogen bond networks; and generating an output related to the one or more screened hydrogen bond networks.

In another aspect, an apparatus is provided. The apparatus includes: means for determining a search space for hydrogen bond networks related to one or more molecules, where the search space includes a plurality of energy terms related to a plurality of residues related to the hydrogen bond networks; means for searching the search space to identify one to or more hydrogen bond networks based on the plurality of energy terms; means for screening the identified one or more hydrogen bond networks to identify one or more screened hydrogen bond networks based on scores for the one or more identified hydrogen bond networks; and means for generating an output related to the one or more screened hydrogen bond networks.

In one aspect, the invention provides polypeptides comprising an amino acid sequence that is at least 75% identical over its full length to the amino acid sequence selected from the group consisting of SEQ ID NOS:2-79.

In another aspect, the invention provides polypeptides comprising or consisting of the amino acid sequence of Formula I:

Z1-Z2-Z3-Z4-Z5, wherein:

Z1 is a helix initiating sequence comprising the amino acid sequence of Formula 2: J1-J2-J3, wherein
J1 is selected from the group consisting of S, T, N, and D;

J2 is selected from the group consisting of P, E, R, K, L, A; and

J3 is selected from the group consisting of E, D, R, K, I, L, V, A, S, T, Y, or is absent;

Z3 is a helix connecting sequence having the amino acid sequence of Formula 3:

(SEQ ID NO: 1)
[RKED]-L-[NQEDRKST]-[NQEDRKST]-[NQEDRKST]-G-
[STNQED]-[STNQED]-[STND]-E-[EDRK]-V-[RKED];

Z5 is a helix terminating sequence comprising the amino acid sequence of Formula 4:

xx-xx-[RKEDSTNQYA];

Z2 is selected from the group consisting of general formulae $BX_1BX_2$, $X_1BBX_2$, $X_1BX_2B$, $X_1X_2B$, $BX_1X_2B$, and $BBX_1X_2$, wherein:

B is xx-S-L-xx-xx-Q-xx;

$X_1$ and $X_2$ independently have the amino acid sequence of Formula 5:

$O_1O_2O_3O_4O_5O_6O_7$ wherein:

$O_1$, $O_4$, $O_5$, and $O_7$ are xx;

$O_2$ and $O_3$ are independently selected from the group consisting of I, L, and A; and $O_6$ is L; and Z4 is selected from the group consisting of general formulae $B_2X_3B_2X_4$, $X_3B_2B_2X_4$, $X_3B_2X_4B_2$, $X_3X_4B_2B_2$, $B_2X_3X_4B_2$, and $B_2B_2X_3X_4$, wherein $B_2$ is xx-L-A-xx-xx-Q-xx; and $X_3$ and $X_4$ independently have the amino acid sequence of Formula 6:

$O_{10}O_{11}O_{12}O_{13}O_{14}O_{15}O_{16}$ wherein $O_{10}$, $O_{13}$, $O_{14}$, and $O_{16}$ are xx $O_{11}$ is L, and $O_{12}$ and $O_{15}$ are independently selected from the group consisting of I, L, V, and A;

wherein xx is any amino acid, and wherein:

(i) when Z2 is $BX_1BX_2$ then Z4 is $X_3B_2X_4B_2$;
(ii) when Z2 is $X_1BBX_2$ then Z4 is $X_3B_2B_2X_4$;
(iii) when Z2 is $X_1BX_2B$ then Z4 is $B_2X_3B_2X_4$;
(iv) when Z2 is $X_1X_2BB$ then Z4 is $B_2X_3X_4B_2$;
(v) when Z2 is $BX_1X_2B$ then Z4 is $B_2X_3X_4B_2$; and
(vi) when Z2 is $BBX_1X_2$ then Z4 is $X_3X_4B_2B_2$.

In other aspects, the invention provides nucleic acids that encode the polypeptides of the invention, expression vectors comprising the nucleic acids of the invention operatively linked to a promoter sequence, and host cells comprising the expression vectors.

Schematics of hydrogen bond networks from 2L6HC3_13 (A) and 5L6HC3_1 (F). The indicated hydrogen bonds are present in both design model and crystal structure.

Figure 3:
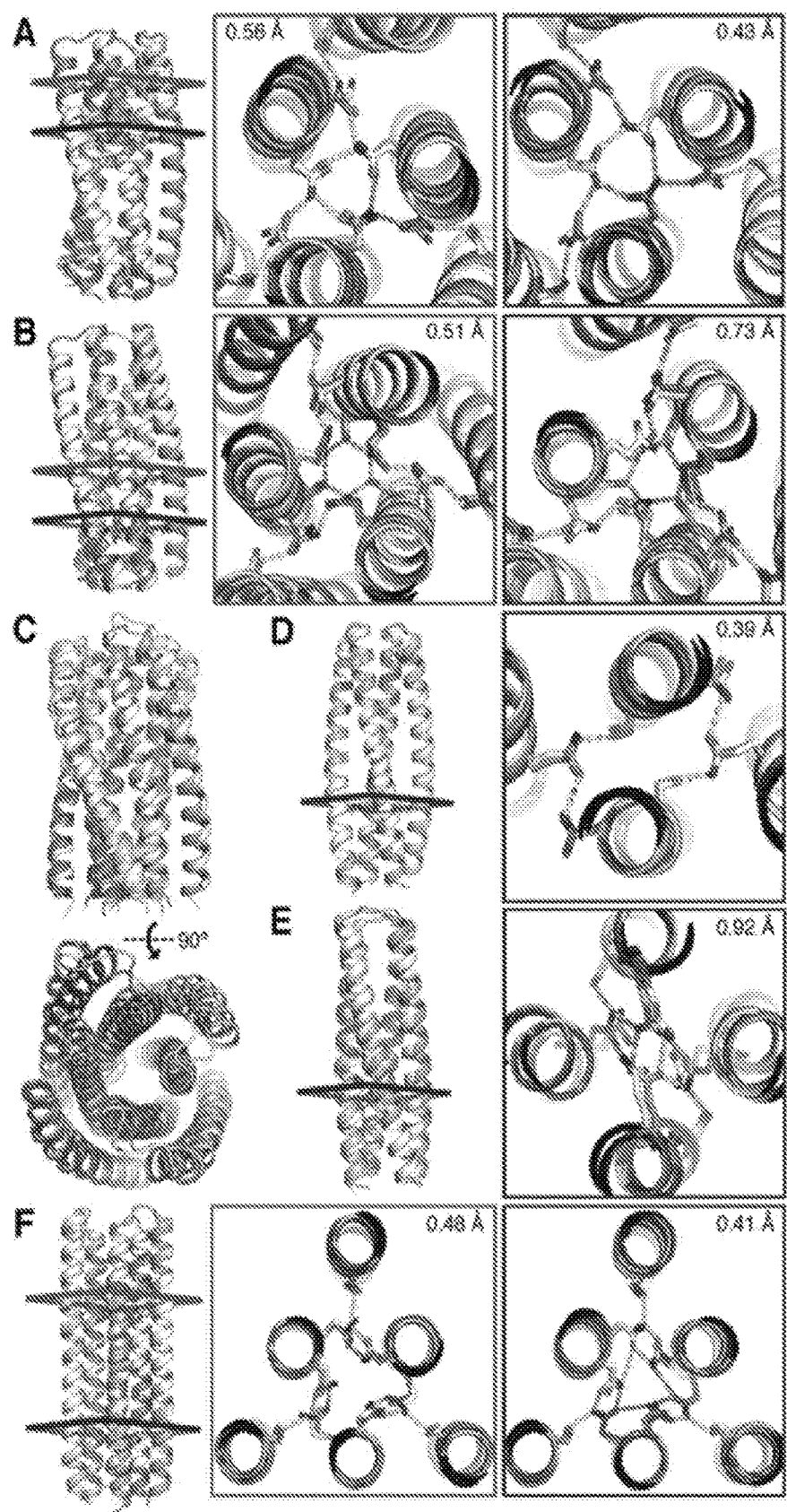
Figure 4:
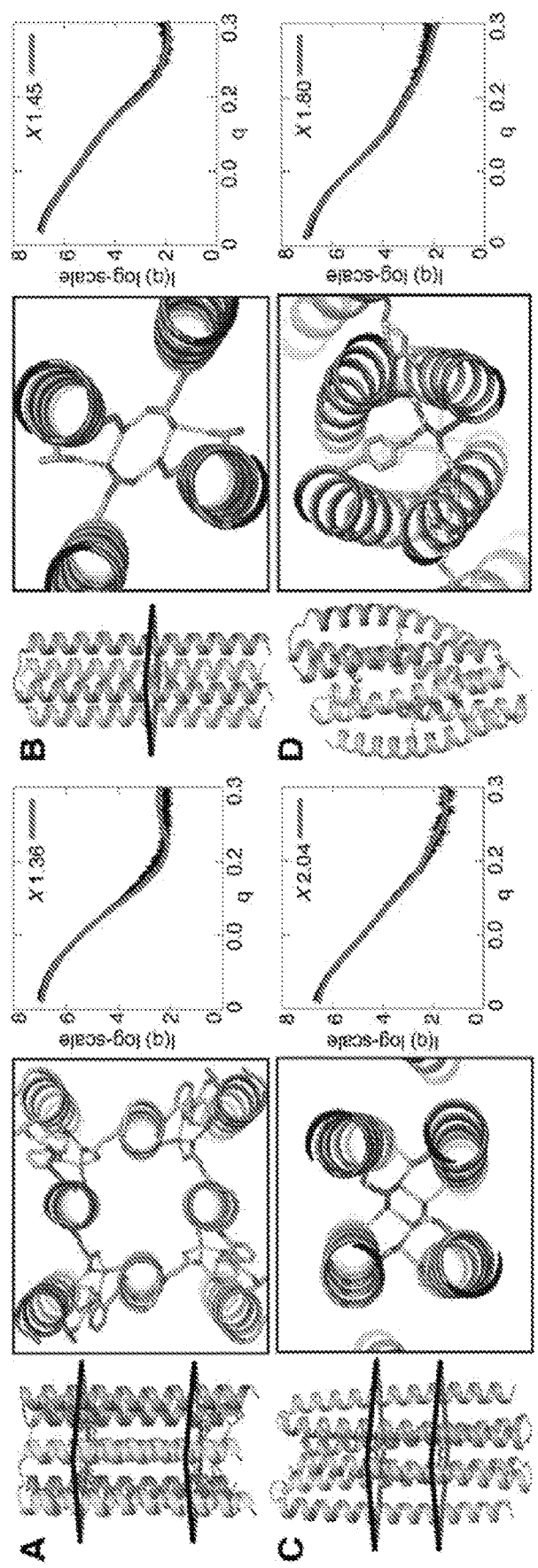

FIG. 4 Structural characterization by small angle x-ray scattering (SAXS). (left) backbones and (middle) h-bond networks for the design models are displayed as in FIG. 3; (right) design models were fit to experimental scattering data (black) using FoXS; Chi2 values of fit (X) indicated inside each panel. (A) 5L8HC4_6 (X=1.36), an untwisted C4 homotetramer with two identical h-bond networks. (B) 5L4HC2_12 (X=1.45), an untwisted C2 homodimer with a single h-bond network. (C) 3L6HC2_4 (X=2.04), a parallel right-handed C2 homodimer with two repeated networks and two inner helices, one outer helix. (D) 2L6Hanti_3 (X=1.80), a left-handed anti parallel homodimer with two inner helices, one outer helix; because of the anti-parallel geometry, the same network occurs in two locations.

Figure 5:
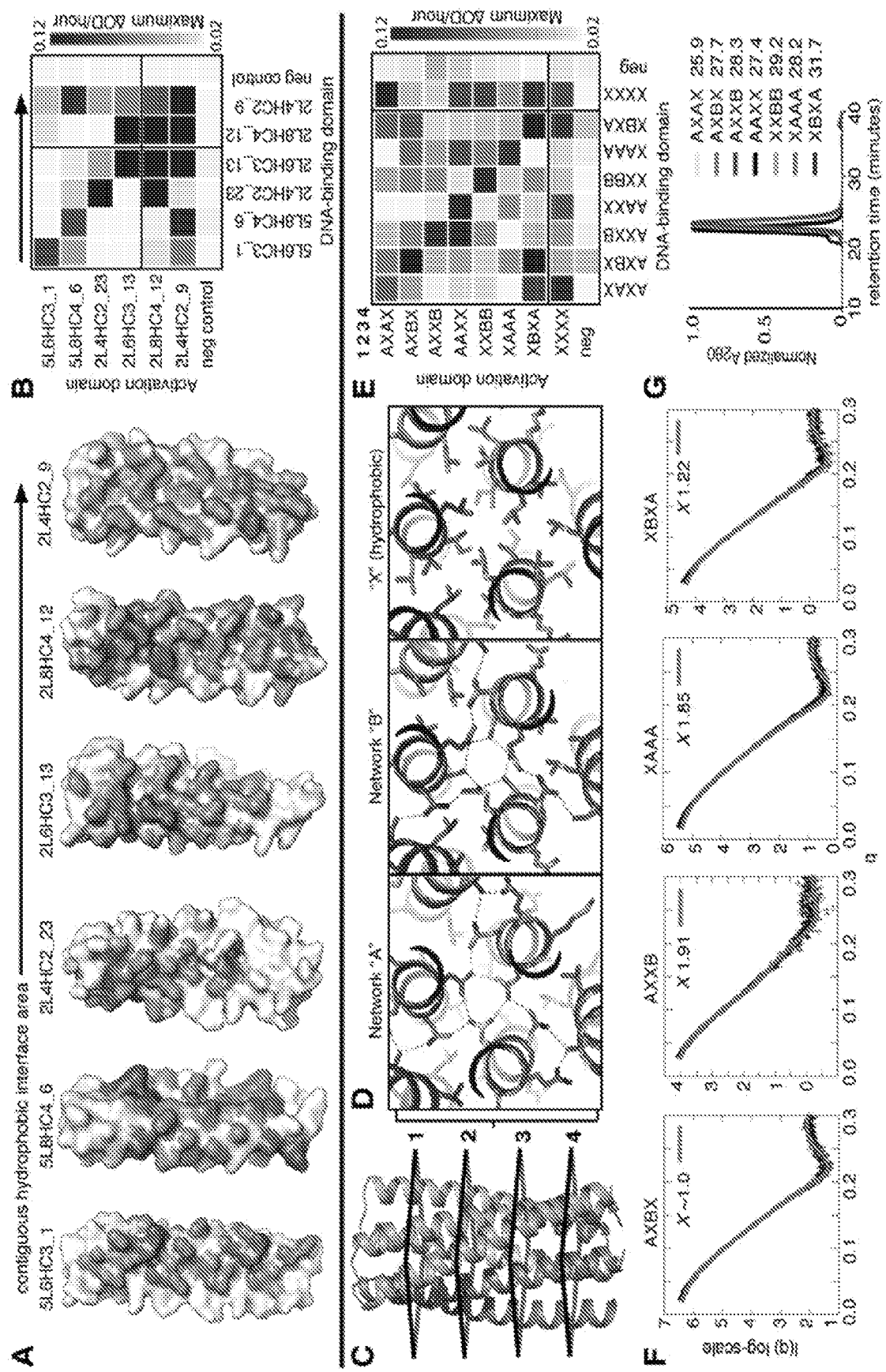

FIG. 5. The hydrogen bond networks confer specificity. (A) Interaction surfaces of monomer subunits for six structurally verified designs, ordered by increasing contiguous hydrophobic interface area, as calculated by h-patch; hydrogen bond network residues are colored. (B) Binding heat-map from yeast two-hybrid assay. Designs in (A) were fused to both DNA-binding domain and Activation domain constructs and binding measured by determining the cell growth rate (maximum ΔOD/hour): darker cells indicate more rapid growth, hence stronger binding; values are the average of at least 3 biological replicates. The heat-map is ordered as in (A), and designs with more extensive networks and better-partitioned hydrophobic interface area exhibit higher interaction specificity. (C-G) Modular networks confer specificity in a programmable fashion. (C) The backbone corresponding to designs 2L6HC3_13 (FIG. 3A) and 2L6HC3_6 (FIG. 3B) can accommodate different networks at each of four repeating geometric cross-sections. (D) Three possibilities for each cross-section: Network "A", Network "B", or hydrophobic, "X". (E) Combinatorial designs using this three letter "alphabet" were tested for interaction specificity using the yeast two-hybrid assay as in (B). Axis labels denote the network pattern; for example, "AXBX" indicates Network A at cross-section 1, Network B at cross-section 3, and X (hydrophobic) at the two others. (F) SAXS profiles for combinatorial designs as in FIG. 4; (G) SEC chromatograms and estimated molecular weights (from MALS); designs range from ~27-30 kDa. AAXX, XXBB, and XXXX correspond to designs 2L6HC3_13, 2L6HC3_6, and 2L6HC3_hydrophobic_1, respectively.

Figure 6:
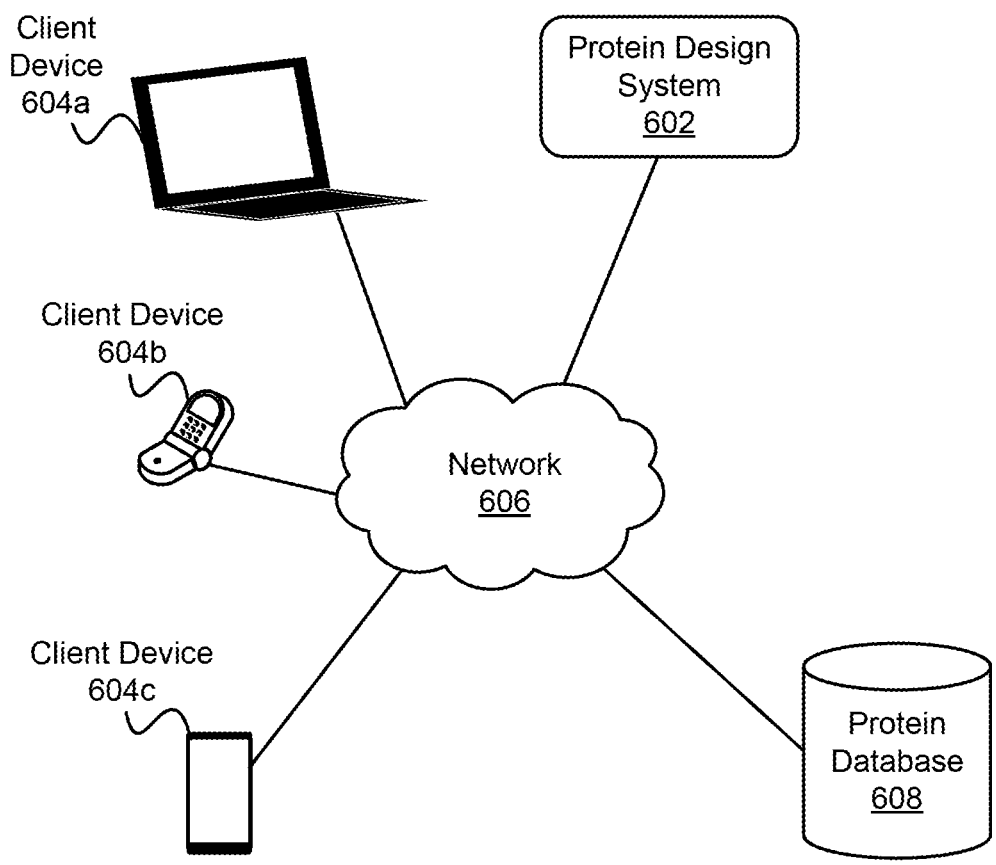

FIG. 6 is a block diagram of an example computing network, in accordance with an example embodiment.

Figure 7A:
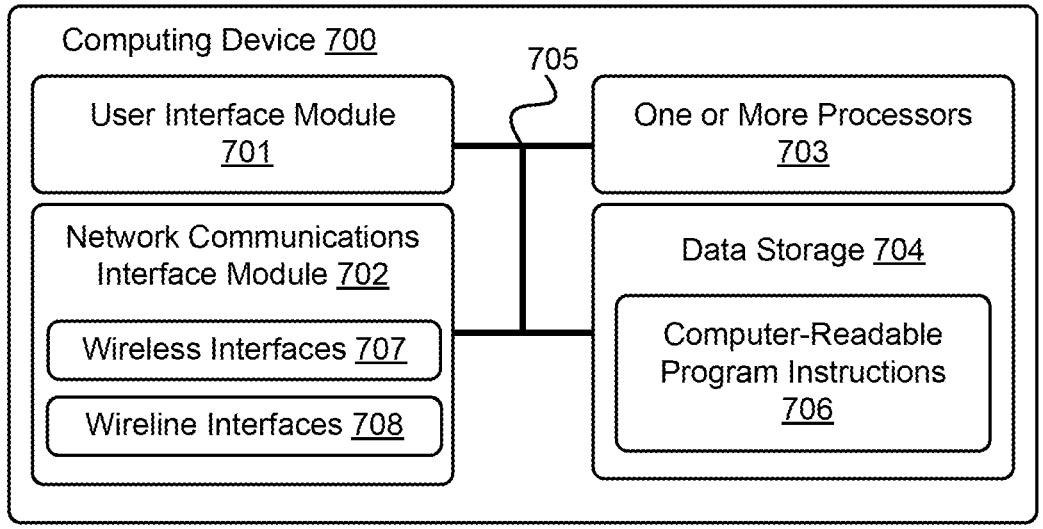

FIG. 7A is a block diagram of an example computing device, in accordance with an example embodiment.

Figure 7B:
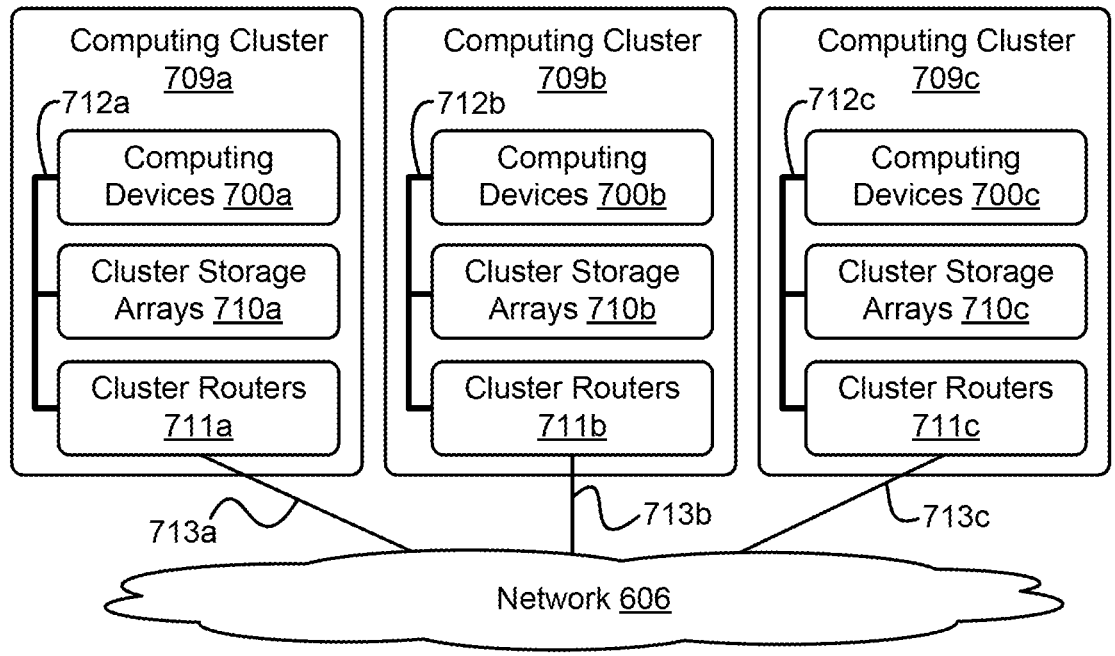

FIG. 7B depicts a network of computing devices arranged as a cloud-based server system, in accordance with an example embodiment.

Figure 8:
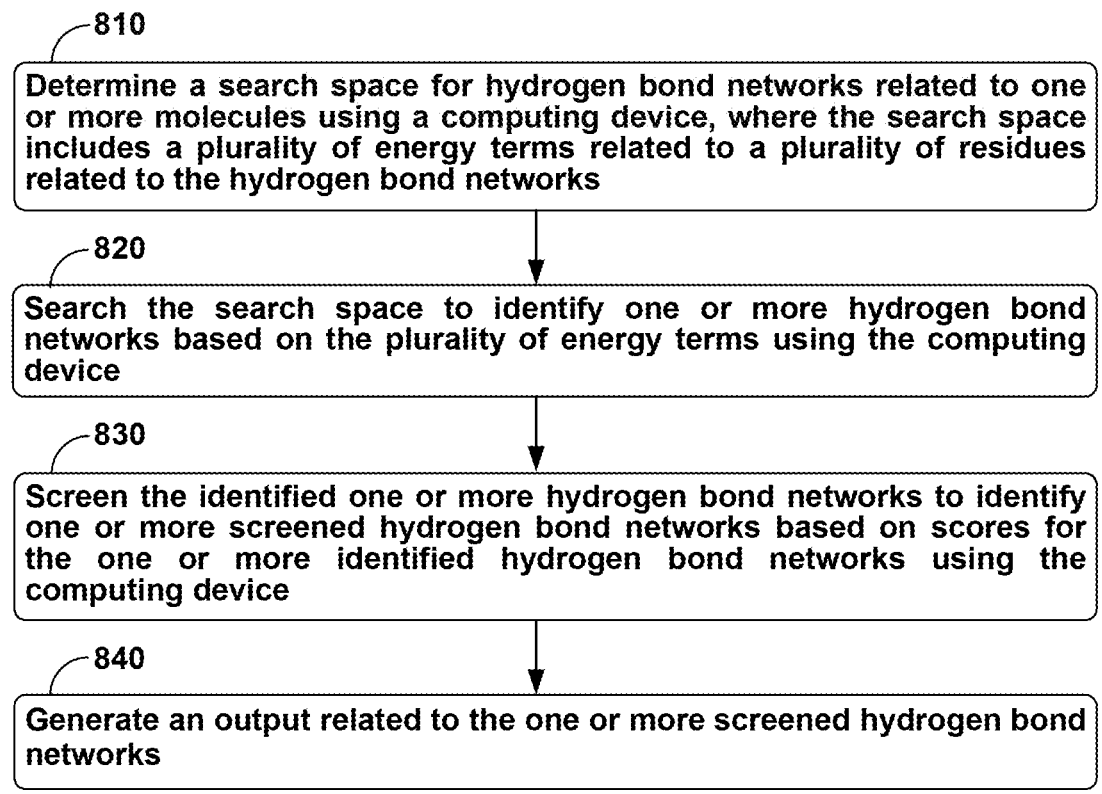

FIG. 8 is a flowchart of a method, in accordance with an example embodiment.

DETAILED DESCRIPTION OF THE INVENTION

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique, 2nd Ed.* (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise. "And" as used herein is interchangeably used with "or" unless expressly stated otherwise.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys K), methionine (Met; M), phenylalanine (Phe; F), proline (Pro; P), serine (Ser, S), threonine (Thr; T), tryptophan (Trp; W), tyrosine (Tyr, Y), and valine (Val; V).

All embodiments of any aspect of the invention can be used in combination, unless the context clearly dictates otherwise.

In one aspect, the invention provides polypeptides comprising an amino acid sequence that is at least 75% identical over its full length to the amino acid sequence selected from the group consisting of SEQ ID NOS:2-79.

```
AXAX
                                        (SEQ ID NO: 2)
TRTRSLREQEEIIRELERSLREQEELLRELERLQREGSSDEDVRE
LLREIKKLAREQKYLVEELKKLAREQKRQD;

XAAX
                                        (SEQ ID NO: 3)
TRTEIIRELERSLREQERSLREQEELLRELERLQREGSSDEDVRE
LLREIKKLAREQKKLAREQKYLVEELKRQD;

XAXA
                                        (SEQ ID NO: 4)
TRTEIIRELERSLREQEELAKRLKRSLREQERLQREGSSDEDVRK
LAREQKELVEEIEKLAREQKYLVEELKRQD;
and XXAA
                                        (SEQ ID NO: 5)
TRTEIIRELEELAKRLKRSLREQERSLREQERLQREGSSDEDVRK
LAREQKKLAREQKELVEEIEYLVEELKRQD
```

Polypeptide Nomenclature:

The name of the polypeptides shown below indicates oligomerization state and topology, and sequences below are organized by topology and oligomerization state. The first two characters indicate supercoil geometry: '2L' refers to a two-layer heptad repeat that results in a left-handed supercoil; '3L' refers to a three-layer 11-residue repeat with a right-handed supercoil; and '5L' refers to untwisted designs with a five-layer 18-residue repeat and straight helices (no supercoiling), where "layer" in this context is the number of unique repeating geometric slices, or layers, along the supercoil axis. The middle two characters indicate the total number of helices, and the final two indicate symmetry. Thus. "2L6HC3" denotes a left-handed, six-helix trimer with C3 symmetry. Underlined residues are optional.

2L8HC4_12

(SEQ ID NO: 6)
GTAIEANSRMLKALIEIAKAIWKALWANSLLLEATSRGDTERMRQ
WAEEAREIYKEAKKIIDEADEIVKEAKERHD

5L6HC3_1

(SEQ ID NO: 7)
SEELRAVADLQRLNIELARKLLEAVARLQELNIDLVRKTSELTDE
KTIREEIRKVKEESKRIVEEAEEEIRRAKEESRYIADESRGS

2L4HC2_9

(SEQ ID NO: 8)
GTSDYIIEQIQRDQEEARKKVEEAEERLERVKEASKRGVSSDQLL
DLIRELAEIIEELIRIIRRSNEAIKELIKNQS

2L4HC2_11

(SEQ ID NO: 9)
GSEDYKLREAQRELDKQRKDTEEIRKRLKEIQRLTDERTSTADEL
IKELREIIRRLQEQSEKLREIIEELEKIIRKR

2L4HC2_23

(SEQ ID NO: 10)
GTRTEIIRELERSLREQEELAKRLKELLRELERLQREGSSDEDVR
ELLREIKELVEEIEKLAREQKYLVEELKRQD

2L4HC2_24

(SEQ ID NO: 11)
GTDTDELLRLAKEQAELLKEIKKLVEEIARLVKEIQEDPSDELLK
TLAELVRKLKELVEDMERSMKEQLYIIKKQKS

5L8HC4_6

(SEQ ID NO: 12)
GSKDTEDSRKIWEDIRRLLEEARKNSEEIWKEITKNPDTSEIARL
LSEQLLEIAEMLVRIAELLSRQTEQR

2L6HC3_AXAX (SEQ ID NO: 13)
GTKYEIREALKEAQKQLEDLKRMLDELRRNLEELKRNPSEDALVE
NNELIVRVLEVIVENNRSIIEILKLLAKSD

2L6HC3_AXBX (SEQ ID NO: 14)
GTKYKIREMLEEAKRSLEELRRILEKLKESLRELRRNPSEDALVN
NNEVIVKAIEASVENQRIIIELARMLAESD

2L6HC3_AXXB (SEQ ID NO: 15)
GTKYRIKDTLRELKRALEELKKILEELQRSLEELRRNPSEDALVN
NNEVIVKAIEAAVRAIEISAENQRMLAESD

2L6HC3_XAAA (SEQ ID NO: 16)
GTKYEARKQLEEMKKQLKRSLERLREILERLEENPSEDVIVEAIR
AIVENNKQIVENNRSIIENNETIIRSD

2L6HC3_XBXA (SEQ ID NO: 17)
GTKYELRRQLEELEKLLRELRKSLDELRKILEELERNPSEDVIVR
AIKASVKNQEIIVEVLRAIIENNKTIAKSD

2L6HC3_12

(SEQ ID NO: 18)
GTKYELRRALEELEKALQELREMLRKLKESLEELKKNPSEDALVR
NNELIVEVLRVIVEVLSIIARVLEINARSD

2L6HC3_13

(SEQ ID NO: 19)
GTKYELRRALEELEKALRELKKSLDELERSLEELEKNPSEDALVE
NNRLNVENNKIIVEVLRIIAEVLKINAKSD

2L6HC3_6

(SEQ ID NO: 20)
GTKYKIKETLKRLEDSLRELRRILEELKEMLERLEKNPDKDVIVE
VLKVIVKAIEASVENQRISAENQKALAESD

2L6HC3_10

(SEQ ID NO: 21)
GTKYEIKKALKELEEAIQKLKKSLKELKESLKELQKNPSEDALVK
NNSLNVANNEIIVEVLEIIARILELLARSD

2L6HC3_11

(SEQ ID NO: 22)
GTKYEIKEALRELNRALKELKEALRELERSLRELQKNPDKDALVR
NNELNVDVARIIVEVLSIIARVLELLAKSD

2L6HC3_12

(SEQ ID NO: 23)
GTKYELRRALEELEKALQELREMLRKLKESLEELKKNPSEDALVR
NNELIVEVLRVIVEVLSIIARVLEINARSD

2L6HC3_13

(SEQ ID NO: 24)
GTKYELRRALEELEKALRELKKSLDELERSLEELEKNPSEDALVE
NNRLNVENNKIIVEVLRIIAEVLKINAKSD

2L6HC3_14

(SEQ ID NO: 25)
GTKYELREAIRKLEEALRKLKKALDELRKSLEELKKNPSEDALVR
NNELNVKAEIIVKVLKIIAEAIKINAKSD

2L6HC3_19

(SEQ ID NO: 26)
GTEEYKLRELLKRHNEVLKELQKAAKEAEEVAERFKKTNDITEAI
RVIADLLRAIVKAIETNSRVVKMIVELNE

2L6HC3_2

(SEQ ID NO: 27)
GTKYIEKLLREAQRTLEELKRLLEELKEMLKELERANATDARLIA
EVIRVIVEVLRASVENQEMIIRILKAITEE

2L6HC3_23

(SEQ ID NO: 28)
TEKDVLRIIVKNNEIIVKVLSVIAEVLKIIAKILENPSEYMLKEL
KKALKELEKMLKELRKSLKELKEALRELEGS

2L6HC3_37

(SEQ ID NO: 29)
GTLDYKLDEMLKKLEKSREEMEKMAQELRRALEELEKNSNVDKVL
KIIIKAIQLSIENQKLNLEAVRLLIEAQKS

2L6HC3_6

(SEQ ID NO: 30)
GTKYKIKETLKRLEDSLRELRRILEELKEMLERLEKNPDKDVIVE
VLKVIVKAIEASVENQRISAENQKALAESD

2L8HC4_3

(SEQ ID NO: 31)
GTDEYKWKEEVRRFEEEAKKWEEELKEMRKRIEDAKKGRPTLKVN
LEAAEEALLEAARLIVEAAKLLLAAAKLNEKQN

2L8HC4_9

(SEQ ID NO: 32)
GSDEDRKAKELIERQRKLTDEAEEWAKQNEEIAKKIEKQPDTSLV
ARMLANVSRMLLATNRALLANTEALEALIRKT

2L8HC4_12

(SEQ ID NO: 33)
GTAIEANSRMLKALIEIAKAIWKALWANSLLLEATSRGDTERMRQ
WAEEAREIYKEAKKIIDEADEIVKEAKERHD

3L6HC2_4

(SEQ ID NO: 34)
SALEKIAKLIIEAARLSAELARRAARASAEMARKAIEAVSEERGS
ESLLKIVADLIVESQEAVVRLIIESQQIAAKLAEDLIRAAKEAAS
DESKMEEVAKEVQERAERAARDIERKLKRVLEELDYKLKESRDGS

3L6HC2_6

(SEQ ID NO: 35)
TALEIAVRLNREAAREAARENADTARKAARRIAEVAKRLAEENRD
AKLAARLLAEIARLLAELIARQSELLAEWLATQSKLAAELARKDT
SATDEAERIRKESEELLDKVREEIKRLEDEVSKTIEELSERVRGS

3L6HC2_7

(SEQ ID NO: 36)
SILELAHESNRRALEMASRANREAMKAAREMIRAASEAARRAGSS
NDKDSLRMIEEALRLALRMIEETNKKAVRMVLENNRKMVEAEKKK
LSEEEIKRIAKETEDRMREIARRASEEARRLAEEIKREADYRSGS

5L6HC3_1

(SEQ ID NO: 37)
SEELRAVADLQRLNIELARKLLEAVARLQELNIDLVRKTSELTDE
KTIREEIRKVKEESKRIVEEAEEEIRRAKEESRYIADESR<u>GS</u>

5L6HC3_3

(SEQ ID NO: 38)
<u>GT</u>ERKDRLRKELKRIAEETDKWVEELKEELERILRTIEELRKDPS
SEVIVDIARIQLEALREVIRVVAENSKAILEAIHRVIEEG

5L6HC3_5

(SEQ ID NO: 39)
SKEVRLQKLNAEIMKEIMELIIRLQEANARIIEELVRLIIDLERS
TDSKRMIEEIRKVAERAIEESKRLLEEAEKAMRRAIYESEDALRE
<u>GS</u>

5L8HC4_1

(SEQ ID NO: 40)
<u>GS</u>KVEELLRKSEEAAERAKRELERLLEESERIVAEAQALAEKYES
QKVWVRILIELIRATNRMLAEIARILLEMIEVTNRMIAESTK

5L8HC4_2

(SEQ ID NO: 41)
SEQLKEIARILIKLIESLTRFILEVARILIELIEETQRLIVASTD
SDESELERIARESKKKAKKALDELKKIVDDQRREAKKAIEELEYD
<u>GS</u>

5L8HC4_6

(SEQ ID NO: 42)
<u>GS</u>KDTEDSRKIWEDIRRLLEEARKNSEEIWKEITKNPDTSEIARL
LSEQLLEIAEMLVRIAELLSRQTEQR

2L4HC2_1

(SEQ ID NO: 43)
<u>GT</u>AYELLRKAEELEKKQQELLKRQEELAKTAEELRKKGGNADSMM
KIIKESTRIVRESTEIVKELLKIIRELRRQS

2L4HC2_5

(SEQ ID NO: 44)
<u>GT</u>RTEYLKKLAEEAKELAKRSRELSKESRRLSEEARRDPDKEKLL
RVVKKLQEVIEELQRVIEELLRVIKEALENQS

2L4HC2_6

(SEQ ID NO: 45)
<u>GT</u>ETEYQRELAREARRLAKRSRELSERSRKLSEDAKRDPDKDKLL
EVVERLQQVIEELQKVIEELLRVIESSLKTIS

2L4HC2_9

(SEQ ID NO: 46)
<u>GT</u>SDYIIEQIQRDQEEARKKVEEAEEERLERVKEASKRGVSSDQLL
DLIRELAEIIEELIRIIRRSNEAIKELIKNQS

2L4HC2_10

(SEQ ID NO: 47)
<u>GT</u>EEYRRKEQEERTKEQQERTERQRRKTEELKRATKEGTLTPEEA
IRQAQKQSENAERQSREAEKQSREANEALRKR

2L4HC2_11

(SEQ ID NO: 48)
<u>GS</u>EDYKLREAQRELDKQRKDTEEIRKRLKEIQRLTDERTSTADEL
IKELREIIRRLQEQSEKLREIIEELEKIIRKR

2L4HC2_12

(SEQ ID NO: 49)
<u>GS</u>EDYKLKELQKRNKKQEEEAKRNDDERKKIEELTRKRTSTADEL
IRELQRSNEEMQRSQREMQDQSRRLEDIIRKR

2L4HC2_14

(SEQ ID NO: 50)
<u>GT</u>EDYKRREAERKLQKQQEELKELKRKLEEIRELHEKGVGSPDRL
IRELERIIRELQRMQKENEKIIKELQRIIKKR

2L4HC2_18

(SEQ ID NO: 51)
<u>GT</u>ESKYLLEEARRLKDEARKLKEEAKKVKEESRKLIERIDRGEDS
DRELLERLKEQNNRLLEIIERLLEIIERLLKLIEEWTRDS

2L4HC2_19

(SEQ ID NO: 52)
<u>GT</u>EEDYAEREIRKMKEEQKRQRKRLEELERELQEMQEKKREGTSD
AKEVIDQLERIIRELQEIIRSQEDITRKLEEIIRRMKENS

2L4HC2_20

(SEQ ID NO: 53)
<u>GT</u>NKEELKRTMEEQQRILEKLLRTIKEQKEILRKQEEGRATKEEL
KRLTKLAQEQERMMRELIDLARKQAYLLKRES

2L4HC2_21

(SEQ ID NO: 54)
<u>GT</u>REEKIRRILEEIQKIMEEIKRIMEEIKRTQEEAEKHGSSKKAI
EKQKELLRRLEELLRKLERLLRELEYLMRDEK

2L4HC2_22

(SEQ ID NO: 55)
<u>GT</u>REEWLYRILELIERIERLIKEIIRLSRRALELLENNASNEEWA
QEIKEMQRKIQEWLKQILEWLKKIKEWIRESQ

2L4HC2_23

(SEQ ID NO: 56)
<u>GT</u>RTEIIRELERSLREQEELAKRLKELLRELERLQREGSSDEDVR
ELLREIKELVEEIEKLAREQKYLVEELKRQD

2L4HC2_24

(SEQ ID NO: 57)
<u>GT</u>DTDELLRLAKEQAELLKEIKKLVEEIARLVKEIQEDPSDELLK
TLAELVRKLKELVEDMERSMKEQLYIIKKQKS

5L4HC2_1

(SEQ ID NO: 58)
<u>GT</u>EETKNSKRVLDIIEELMRQVEENSRELEKRIKELLRQTKEGKT
KKELERDVRRTIEEQKKELRRLKEQVRKTKEEQREEQYRS

5L4HC2_2

(SEQ ID NO: 59)
<u>GT</u>RTEKLMKEVEEIQRRQIELLKKLMKEVEDSSKRNQEATERGTT
KKKWKEEQEKILEDLKREVRRIIEESRKWLEDLKKKVYES

5L4HC2_3

(SEQ ID NO: 60)
<u>GT</u>EKYRLREEVRRTIEEQKENLERLKQEVKETERKTEEWRERNTT
TEDAQREQIKIIRRLMKEVERNSRRLEKELRRLVEETRES

5L4HC2_6

(SEQ ID NO: 61)
<u>GT</u>EKYRLIRESERALRELKRKVRELEEDQRERLDEQRKKVEEGQT
TDELLRQNEENSRRMLKETKKLLREIERIQREQQRQNQEN

5L4HC2_7

(SEQ ID NO: 62)
<u>GT</u>EKEKEIEKNSREVIKQVEDILREIKENSKRNIEIIKELQKDPS
DEKMRETIEQQRENLERLERKARELIRRQERNLRETQYKD

5L4HC2_9

(SEQ ID NO: 63)
<u>GT</u>EKYRIIEEQRRNLEDLEREIREIIKKLKEALERLRELVERNST
NDRLLDEVRKIIEEAIEDMKRLLEKVERSIRQNIEELRRS

5L4HC2_10

(SEQ ID NO: 64)
<u>GT</u>NKEYLRRKVKELKDQQKRNLEELEREVRRLIKEIEEWRERNTT
TDRALKEIIRQIQRLLEEARRNSEEVLRQIEEIMEETRES

5L4HC2_11

(SEQ ID NO: 65)
<u>GT</u>EEERAERIIRAIRELMREVERNSKEVLQWIKEMLRLTKENSST
KELEERWREIEERQRRNLEKLKEEVRRLEDEIRQETYRS

5L4HC2_12

(SEQ ID NO: 66)
<u>GT</u>ETKKLVEEVERALRELLKTSEDLVRKVEKALRELLELIRRGGT
KDKIEEKIRRVLEEIKRELERQRKRKIEDVLRQIKEELYRS

2L6Hanti_1

(SEQ ID NO: 67)
SDYLRLATEHNKLAVEANRLAIELAKSAVELAETDPSKTALEHAE
LAARLLEMMVQFTKAAQELTREAIRKEGRNEESEKVLRKSKEAYK
ESEKALEDARRLLDELRKK<u>GS</u>

-continued

2L6Hanti_2
(SEQ ID NO: 68)
SEELRKAAENNELAVRLAEAALRMARSALHLFEENPSDEMLKFLE
LAMEVAKMAAELLKASLKMLKKAAEERGSDESVKYLADKSRDIMR
QITEELKKLEEEAKRAQKRGS 2L6Hanti_3
(SEQ ID NO: 69)
SEKARIAVENLEAALRLNRAAAEMQKSAIKIMDDNRSDEKALRYL
RLTTKVLRMSVELLRASLELAEKALREEGSDDSAEKVRKEAEEIL
KESTEILKEADKETKRADEEGS 2L6Hanti_4
(SEQ ID NO: 70)
SRRLELAARINKAAAENARSAIEIQELAARLADELSSSKKVIDFA
RATTEVLRMSVKLLKLSLEMLEEAARQDGRSEEVRYLAEESKKIL
EEARKALEDADRLTKRIEEEGS 2L6Hanti_5
(SEQ ID NO: 71)
TDVLRIAAENLKAAVELAKAALEMAKSAIEIAKTLTEDDEALKFA
RAAAEVLRMAAKLLKLSIELARKAAEEEGSDDEVRYILDEARKQA
DELREALKKVDEIMKELDKRGS 5H2LD_10
(SEQ ID NO: 72)
TRRKQEMKRLKYEMEKIREETEEVKKEIEESKKRPQSESAKNLIL
IMQLLINQIRLLALQIRMLALQLQE 5H2LD_13
(SEQ ID NO: 73)
TEDQERLRKQMEYERKHTEKVEKEIRKVEQKMKSHEDTSLRLLVL
LIARLLINQIRLLILQIRSLSNLERN 5H2LD_15
(SEQ ID NO: 74)
TESTLLILIMRLLVQQSELLQLQIQMLQLLLKANNGTNKTEIERR
SKEMEEELKRMKESNREMTKRIKEME 5H2LD_18
(SEQ ID NO: 75)
TESDLLRQISKLLIIQIRLLLLQIQMLILLLKMNTGTNTTQITKE
AKRIEKEAQEARKELEKMQESNKKQT 6H2LD_8
(SEQ ID NO: 76)
TEDEIRKLRKLLEEAEKKLYKLEDKTRRSEEISKTDDDPKAQSLQ
LIAESLMLIAESLLIIAISLLLSSRNG 7H2LD_3
(SEQ ID NO: 77)
TEDEELQRVEEEIRELERKAKELHYKSEEIRKKVNGRSPQAEALL
MIAQALLNISESLLAIAKALLMIARST 8H2LD_4
(SEQ ID NO: 78)
TDEREIIKRVKRLLEEVEYLIERLRDQIEKAEKGLLDSRKAQQNA
EALVNLIKAMVLVLKALLLAKELER 8H2LD_4_KE
(SEQ ID NO: 79)
TEEQYIIEEVKKLLEEVKKLIEELKKQIEKAEKGEEDSRKAQQNA
EALVNLIKAMVLVLKALLLAKELER The polypeptides of this aspect of the invention have been shown in the examples that follow to be capable of forming homo-oligomers with modular hydrogen bond network-mediated specificity. In various embodiments, the polypeptides comprise or consist of an amino acid sequence that is at least 75%, 80%, 85%, 90%, 91%, 92%, 93%, 94%, 95%, 96%, 97%, 98%, 99%, or 100% identical over its full length to the amino acid sequence selected from the group consisting of SEQ ID NOS:2-79.

As used throughout the present application, the term "polypeptide" is used in its broadest sense to refer to a sequence of subunit amino acids. The polypeptides of the invention may comprise L-amino acids, D-amino acids (which are resistant to L-amino acid-specific proteases in vivo), or a combination of D- and L-amino acids. The polypeptides described herein may be chemically synthesized or recombinantly expressed. The polypeptides may be linked to other compounds to promote an increased half-life in vivo, such as by PEGylation, HESylation, PASylation, glycosylation, or may be produced as an Fc-fusion or in deimmunized variants. Such linkage can be covalent or non-covalent as is understood by those of skill in the art.

As will be understood by those of skill in the art, the polypeptides of the invention may include additional residues at the N-terminus, C-terminus, or both that are not present in the polypeptides of the invention; these additional residues are not included in determining the percent identity of the polypeptides of the invention relative to the reference polypeptide.

In one embodiment, changes from the reference polypeptide are conservative amino acid substitutions. As used herein, "conservative amino acid substitution" means an amino acid substitution that does not alter or substantially alter polypeptide function or other characteristics. A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. antigen-binding activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser, Arg into Lys; Asn into Gln or into H is; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

As noted above, the polypeptides of the invention may include additional residues at the N-terminus, C-terminus, or both. Such residues may be any residues suitable for an intended use, including but not limited to detection tags (i.e.: fluorescent proteins, antibody epitope tags, etc.), linkers, ligands suitable for purposes of purification (His tags, etc.), and peptide domains that add functionality to the polypeptides.

In another aspect, the invention provides polypeptides comprising or consisting of the amino acid sequence of Formula I:

Z1-Z2-Z3-Z4-Z5, wherein:

Z1 is a helix initiating sequence comprising the amino acid sequence of Formula 2: J1-J2-J3, wherein
- J1 is selected from the group consisting of S. T, N, and D;
- J2 is selected from the group consisting of P, E, R, K, L, A; and
- J3 is selected from the group consisting of E, D, R, K, I, L, V, A, S, T, Y, or is absent;

Z3 is a helix connecting sequence having the amino acid sequence of Formula 3:

(SEQ ID NO: 1)
[RKED]-L-[NQEDRKST]-[NQEDRKST]-[NQEDRKST]-G-[STNQED]-[STNQED]-[STND]-E-[EDRK]-V-[RKED];

Z5 is a helix terminating sequence comprising the amino acid sequence of Formula 4:

xx-xx-[RKEDSTNQYA];

Z2 is selected from the group consisting of general formulae $BX_1BX_2$, $X_1BBX_2$, $X_1BX_2B$, $X_1X_2BB$, $BX_1X_2B$, and $BBX_1X_2$, wherein:
- B is xx-S-L-xx-xx-Q-xx;
- $X_1$ and $X_2$ independently have the amino acid sequence of Formula 5:

$O_1O_2O_3O_4O_5O_6O_7$ wherein:

- $O_1$, $O_4$, $O_5$, and $O_7$ are xx;
- $O_2$ and $O_3$ are independently selected from the group consisting of L, and A; and
- $O_6$ is L; and Z4 is selected from the group consisting of general formulae $B_2X_3B_2X_4$, $X_3B_2B_2X_4$, $X_3B_2X_4B_2$, $X_3X_4B_2B_2$, $B_3X_3X_4B_2$, and $B_2B_2X_3X_4$, wherein
- $B_2$ is xx-L-A-xx-xx-Q-xx; and
- $X_3$ and $X_4$ independently have the amino acid sequence of Formula 6:

$O_{10}O_{11}O_{12}O_{13}O_{14}O_{15}O_{16}$ wherein

- $O_{10}$, $O_{13}$, $O_{14}$, and $O_{16}$ are xx
- $O_{11}$ is L, and
- $O_{12}$ and $O_{15}$ are independently selected from the group consisting of I L, V, and A;

wherein xx is any amino acid, and
wherein:
(i) when Z2 is $BX_1BX_2$ then Z4 is $X_3B_2X_4B_2$;
(ii) when Z2 is $X_1BBX_2$ then Z4 is $X_3B_2B_2X_4$;
(iii) when Z2 is $X_1BX_2B$ then Z4 is $B_2X_3B_2X_4$;
(iv) when Z2 is $X_1X_2BB$ then Z4 is $B_2B_2X_3X_4$;
(v) when Z2 is $BX_1X_2B$ then Z4 is $B_2X_3X_4B_2$; and
(vi) when Z2 is $BBX_1X_2$ then Z4 is $X_3X_4B_2B_2$.

The polypeptides of this aspect of the invention have been shown in the examples that follow to be capable of forming homo-oligomers with modular hydrogen bond network-mediated specificity.

In one embodiment, J3 is present. In another embodiment, Z1 is TRT. In a further embodiment, Z3 is RLQREGSSD-EDVR (SEQ ID NO: 81). In a still further embodiment, Z5 is RQD. In another embodiment, B is RSLREQE (SEQ ID NO: 82). In a further embodiment, $O_1$, $O_4$, $O_5$, and $O_7$ are independently selected from the group consisting of E, R, and K. In a still further embodiment, $X_1$ and $X_2$ are independently selected from the group consisting of EIIRELE (SEQ ID NO: 83), ELLRELE (SEQ ID NO: 84), and ELAKRLK (SEQ ID NO: 85). In another embodiment, $B_2$ is KLAREQK (SEQ ID NO: 86). In one embodiment, $O_{12}$ and $O_{15}$ are independently selected from the group consisting of I, L, V, and A. In another embodiment, $X_3$ and $X_4$ are independently selected from the group consisting of [YE]-LVEELK (SEQ ID NO: 87), [YE]-LLREIK (SEQ ID NO: 88), and [YE]-LVEEIE (SEQ ID NO: 89). As used herein, residues in brackets are alternative residues for a given position within the recited peptide domain. In a further embodiment, $X_3$ and $X_4$ are independently selected from the group consisting of ELVEELK (SEQ ID NO: 90), ELLREIK (SEQ ID NO: 91), and ELVEEIE (SEQ ID NO: 92). In a still further embodiment, Z2 is selected from the group consisting of general formulae $BX_1BX_2$, $X_1BBX_2$, $X_1BX_2B$, and $X_1X_2BB$; and Z4 is selected from the group consisting of general formulae $B_2X_3B_2X_4$, $X_3B_2B_2X_4$, $X_3B_2X_4B_2$, and $X_3X_4B_2B_2$. In a further embodiment, the polypeptides of this aspect of the invention comprise a polypeptide that is at least 75% identical over its full length to the amino acid sequence selected from the group consisting of SEQ ID NOS:2-5.

In another embodiment of any aspect, embodiment, or combination of embodiments of the invention, the polypeptides are linked to a cargo. As used herein, the "cargo" can be any suitable component, including but not limited to nucleic acids, peptides, small molecules, amino acids, a detectable label, etc. In one non-limiting embodiment, the polypeptides of the invention can be modified to facilitate covalent linkage to a "cargo" of interest. In one non-limiting example, the polypeptides can be modified, such as by introduction of various cysteine residues at defined positions to facilitate linkage to one or more antigens of interest, such that a nanostructure of the polypeptides would provide a scaffold to provide a large number of antigens for delivery as a vaccine to generate an improved immune response. In some embodiments, some or all native cysteine residues that are present in the polypeptides but not intended to be used for conjugation may be mutated to other amino acids to facilitate conjugation at defined positions. In another non-limiting embodiment, the polypeptides of the invention may be modified by linkage (covalent or non-covalent) with a moiety to help facilitate "endosomal escape." For applications that involve delivering molecules of interest to a target cell, such as targeted delivery, a critical step can be escape from the endosome—a membrane-bound organelle that is the entry point of the delivery vehicle into the cell. Endosomes mature into lysosomes, which degrade their contents. Thus, if the delivery vehicle does not somehow "escape" from the endosome before it becomes a lysosome, it will be degraded and will not perform its function. There are a variety of lipids or organic polymers that disrupt the endosome and allow escape into the cytosol. Thus, in this embodiment, the polypeptides can be modified, for example, by introducing cysteine residues that will allow chemical conjugation of such a lipid or organic polymer to the monomer or resulting assembly surface. In another non-limiting example, the polypeptides can be modified, for example, by introducing cysteine residues that will allow chemical conjugation of fluorophores or other imaging agents that allow visualization of the nanostructures of the invention in vitro or in vivo.

In another embodiment, the invention provides homo-oligomers (i.e.: homodimer, homotrimers, homotetramer, etc.) comprising a plurality of polypeptides of the present invention having the same amino acid sequence. As shown in the examples that follow, the polypeptides of the invention are capable of forming homo-oligomers with modular hydrogen bond network-mediated specificity.

In a further aspect, the present invention provides isolated nucleic acids encoding a polypeptide of the present invention. The isolated nucleic acid sequence may comprise RNA or DNA. As used herein, "isolated nucleic acids" are those that have been removed from their normal surrounding nucleic acid sequences in the genome or in cDNA sequences. Such isolated nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the polypeptides of the invention.

In another aspect, the present invention provides recombinant expression vectors comprising the isolated nucleic acid of any aspect of the invention operatively linked to a suitable control sequence. "Recombinant expression vector" includes vectors that operatively link a nucleic acid coding region or gene to any control sequences capable of effecting expression of the gene product. "Control sequences" operably linked to the nucleic acid sequences of the invention are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type known in the art, including but not limited plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The construction of expression vectors for use in transfecting host cells is well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; *Gene Transfer and Expression Protocols*, pp. 109-128, ed. E. J. Murray, The Humana Press Inc., Clifton, N.J.), and the Ambion 1998 Catalog (Ambion, Austin, Tex.). The expression vector must be replicable in the host organisms either as an episome or by integration into host chromosomal DNA. In various embodiments, the expression vector may comprise a plasmid, viral-based to vector, or any other suitable expression vector.

In a further aspect, the present invention provides host cells that comprise the recombinant expression vectors disclosed herein, wherein the host cells can be either prokaryotic or eukaryotic. The cells can be transiently or stably engineered to incorporate the expression vector of the invention, using standard techniques in the art, including but not limited to standard bacterial transformations, calcium phosphate co-precipitation, electroporation, or liposome mediated-, DEAE dextran mediated-, polycationic mediated-, or viral mediated transfection. (See, for example, *Molecular Cloning: A Laboratory Manual* (Sambrook, et al., 1989, Cold Spring Harbor Laboratory Press; *Culture of Animal Cells: A Manual of Basic Technique*, $2^{nd}$ Ed. (R. I. Freshney. 1987. Liss, Inc. New York, N.Y.). A method of producing a polypeptide according to the invention is an additional part of the invention. The method comprises the steps of (a) culturing a host according to this aspect of the invention under conditions conducive to the expression of the polypeptide, and (b) optionally, recovering the expressed polypeptide. The expressed polypeptide can be recovered from the cell free extract, but preferably they are recovered from the culture medium. Methods to recover polypeptide from cell free extracts or culture medium are well known to the person skilled in the art.

Examples

Figure 1:
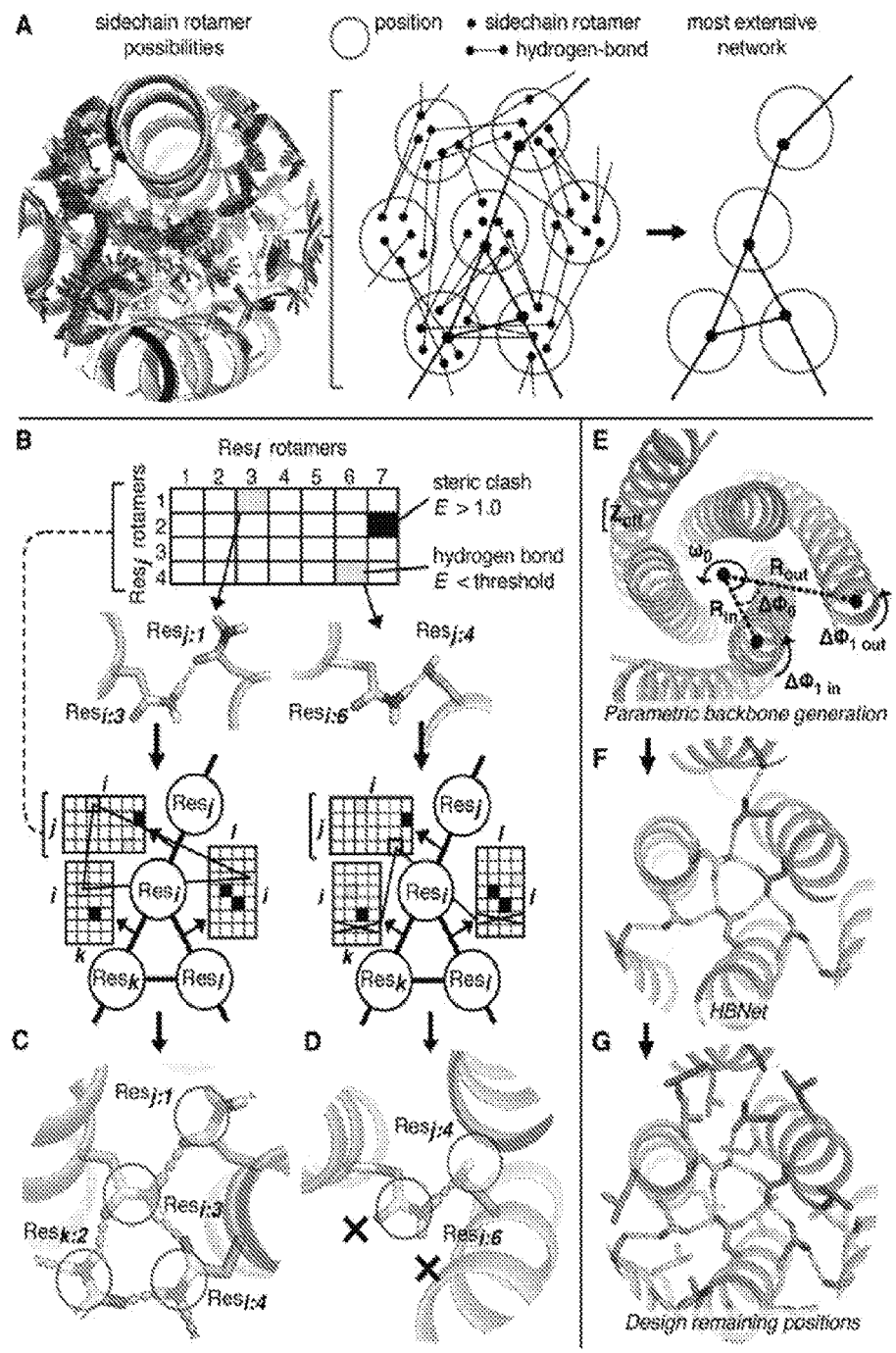
FIG. 1. Overview of the HBNet™ method and design strategy. (A) (left) All sidechain conformations (rotamers) of polar amino acid types considered for design at each residue position; (middle) many combinations of hydrogen-bonding rotamers are possible and the challenge is to traverse this space and extract (right) networks of connected hydrogen bonds. (B-D) HBNet™. (B) HBNet™ precomputes the hydrogen bond and steric repulsive interaction energies between sidechain rotamers at all pairs of positions and stores them in a graph structure; nodes are residue positions, residue pairs close enough to interact are connected by edges, and for each edge there is an interaction energy matrix; yellow indicates rotamer pairs with energies below a specified threshold (hydrogen bonds with good geometry and little steric repulsion). Traversing the graph elucidates all possible connectivities of hydrogen bonding rotamers (networks) that do not clash with each other. In the simple example shown, two pairs of sidechain rotamers at $Res_i$ and $Res_j$ make good-geometry hydrogen bonds, but graph traversal shows that only one of these (left) can be extended into a connected network: (C) $Res_i$ rotamer 3 (i:3) can also hydrogen bond to $Res_k$ rotamer 2 (k:2) and $Res_j$ rotamer 4 (l:4), yielding a "good" network of fully connected Asn residues with all heavy-atom donors and acceptors satisfied, whereas (D) would be rejected because the hydrogen-bonding rotamers i:6 (Gln) and j:4 (Ser) cannot form additional hydrogen bonds to nearby positions k and l, leaving unsatisfied buried polar atoms. (E-G) Design strategy: (E) Parametric backbone generation of two-ring coiled coils: a C3 symmetric trimer is shown, colored by monomer subunit labeled with parameters sampled: supercoil radius of inner ($R_{in}$) and outer ($R_{out}$) helices, helical phase of the inner ($\Delta\varphi_{1\ in}$) and outer ($\Delta\varphi_{1\ out}$) helices, supercoil phase of the outer helix (11cp0), z-offset between the inner and outer helices ($Z_{off}$), and the supercoil twist ($\omega_0$). (F) HBNet™ is applied to parametric backbones to identify the best hydrogen bond networks. (G) Networks are maintained while remaining residue positions are designed in context of the assembled symmetric oligomer.

The modular and predictable nature of DNA interaction specificity is central to molecular biology manipulations and DNA nanotechnology, but without parallels in nature, it has not been evident how to achieve analogous programmable specificity with proteins. There are more polar amino acids than DNA bases, each of which can adopt numerous sidechain conformations in the context of different backbones, allowing for countless network possibilities. The inventors have developed a general computational method, HBNet™ was developed to rapidly enumerate all sidechain hydrogen bond networks possible in an input backbone structure (FIG. 1A).

Traditional protein design algorithms are not well suited for this purpose because the total system energy is generally expressed as the sum of interactions between pairs of residues for computational efficiency, and hence cannot clearly distinguish a connected hydrogen bond network from a set of disconnected hydrogen bonds. HBNet™ starts by precomputing the hydrogen bonding and steric repulsion interactions between all conformations (rotameric states) of all pairs of polar sidechains. These energies are stored in a graph data structure where the nodes are residue positions, positions close in three-dimensional space are connected by edges, and for each edge there is a matrix representing the interaction energies between the different rotameric states at the two positions. HBNet™ then traverses this graph to identify all networks of three or more residues connected by low energy hydrogen bonds with little steric repulsion (FIG. 1B). The most extensive and lowest energy networks (FIG. 1C) are kept fixed in subsequent design calculations at the remaining residue positions. Networks with buried donors and acceptors not making hydrogen bonds (unsatisfied) are rejected (FIG. 1D). Details of the method, as well as scripts for carrying out the design calculations, are described herein.

Inspired by the DNA double helix, it was attempted to host the hydrogen bond networks in protein oligomers with an inherent repeat structure to enable networks to be reutilized within the same scaffold. Attention was paid to coiled-coils, which are abundant in nature, the subject of many protein design studies, and can be generated parametrically, resulting in repeating geometric cross-sections. In natural and designed coiled coils, buried polar interactions can also alter specificity; however, most of these cases involve at most one or two sidechain-sidechain hydrogen bonds with remaining polar atoms satisfied by water or ions—the relatively small cross-sectional interface area of canonical coiled-coils limits the diversity and location of possible networks. To overcome these limitations, focus was placed on oligomeric structures with two concentric rings of helices (FIG. 1E).

"Two-ring" topologies were built from helical hairpin monomer subunits comprising an inner and outer helix connected by a short loop using a generalization of the Crick coiled-coil parameterization. Wide ranges of backbones were generated by systematically sampling the radii and helical phases of the inner and outer helices, the z-offset between inner and outer helices, and the overall supercoil twist (FIG. 1E). HBNet™ was then used to search these backbones for networks that span the intermolecular interface, have all heavy atom donors and acceptors satisfied, and involve at least three sidechains (FIG. 1F; because of these stringent requirements, only a small fraction of backbones can support such networks—but by systematically varying the degrees of freedoms of the two-ring structures, tens of thousands of backbones can be generated, and the efficiency of HBNet™ makes searching for networks in large numbers of backbones computationally tractable). RosettaDesign™ was then used to optimize rotamers at the remaining residue positions in the context of the cyclic symmetry of the oligomer (FIG. 1G). Designs were ranked based on the total oligomer energy using the Rosetta™ all atom force field, filtering to remove designs with large cavities or poor packing around the networks. The top-ranked designs were evaluated using Rosetta™ "fold-and-dock" calculations. Designs with energy landscapes shaped like funnels leading into the target designed structure were identified, and a total of 114 dimeric, trimeric, and tetrameric designs spanning a broad range of superhelical parameters and hydrogen bond networks were selected for experimental characterization.

Figure 2:
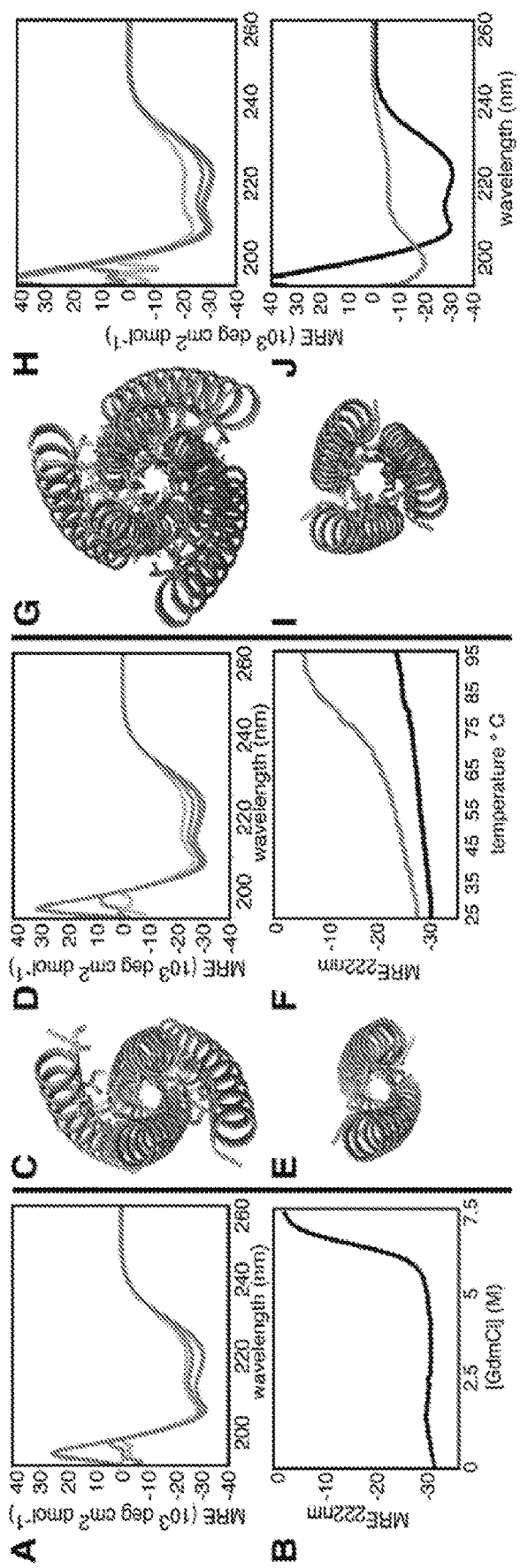
FIG. 2. The outer ring of helices increase thermostability and can overcome poor helical propensity of the inner helices. (A) CD spectrum (260-195 nm) of design 2L4HC2_23 at 25° C. (blue), 75° C. (red), 95° C. (green), and 25° C. after cooling (purple). (B) 2L4HC2_23, denaturation by GdmCl monitoring 222 nm; (C) 2L4HC2_9, a supercoiled C2 homodimer colored by chain, looking down the supercoil axis. (D) CD spectrum of 2L4HC2_9 as in (A). (E) Inner ring design of 2L4HC2_9. (F) CD temperature melt monitoring absorption at 222 nm; 2L4HC2_9 (black) is significantly more stable than 2L4HC2_9_inner (gray). (G) 2L6HC3_13, a supercoiled C3 homotrimer. (H) CD spectrum of 2L6HC3_13 at different temperatures as in (A). (I) 2L6HC3_13_inner. (3) CD spectrum of 2L6HC3_13 (black) versus 2L6HC3_13_inner (gray) shows that the inner helix by itself is primarily unfolded. All CD data is plotted in Mean Residue Ellipticity (MRE) $10^3$ deg cm$^2$ dmol$^{-1}$ FIG. 3. Structural characterization by x-ray crystallography. (A-F) Crystal structures (white) are superimposed onto the design models for six different topologies; (left) the full backbone is shown with cross-sections corresponding to the (middle) designed hydrogen bond networks; panel outline color corresponds to cross-section color on the left; RMSD over all network residue heavy-atoms is reported inside each panel. (A) 2L6HC3_13 (1.64 Å resolution; RMSD=0.51 Å over all Cα atoms) and (B) 2L6HC3_6 (2.26 Å resolution; RMSD=0.77 Å over all Cα atoms) are left-handed C3 homotrimers, each with two identical networks at different locations that span the entire interface, contacting all six helices. (C) 2L8HC4_12, a left-handed C4 homotetramer with two different hydrogen bond networks; the low (3.8 Å) resolution does not allow assessment of the hydrogen bond network sidechains. (D) 2L4HC2_9 (2.56 Å resolution; 0.39 Å RMSD over all Cα atoms) and (E) 2L4HC2_23 (1.54 Å resolution; RMSD=1.16 Å over all Cα atoms) are left-handed C2 homodimers, each with one network. (F) 5L6HC3_1 (2.36 Å resolution; RMSD=0.51 Å over all Cα atoms) is a C3 homotrimer with straight, untwisted helices and two identical networks at different cross-sections. (G, H)

Synthetic genes encoding the selected designs were obtained and the proteins expressed in *Escherichia coli*. The ~90% (101/114) of designs that were expressed and soluble were purified by affinity chromatography, and their oligomerization state evaluated by size-exclusion chromatography multi-angle light scattering (SEC-MALS). Sixty-six of the 101 were found to have the designed oligomerization state. The 101 soluble designs span eight different topologies; of these, the supercoiled tetramers have the largest buried interface area, yielded the fewest designs with all buried donors and acceptors satisfied, and had the lowest success rate (only 3 of the 13 soluble designs properly assembled). Excluding supercoiled tetramers, 72~(63/88) assembled to the designed oligomeric state, and of these, 89% (56/63) eluted as a single peak from the SEC column. The designed proteins were further characterized by circular dichroism (CD) spectroscopy; all designs tested exhibited characteristic a-helical spectra, and CD monitored unfolding experiments showed that more than 90% of these were stable at 95° C. (FIG. 2). Tested peptides include the following:

AXAX
(SEQ ID NO: 2)
TRTRSLREQEEIIRELERSLREQEELLRELERLQREGSSDEDVRE
LLREIKKLAREQKYLVEELKKLAREQKRQD;

XAAX
(SEQ ID NO: 3)
TRTEIIRELERSLREQERSLREQEELLRELERLQREGSSDEDVRE
LLREIKKLAREQKKLAREQKYLVEELKRQD;

XAXA
(SEQ ID NO: 4)
TRTEIIRELERSLREQEELAKRLKRSLREQERLQREGSSDEDVRK
LAREQKELVEEIEKLAREQKYLVEELKRQD;
and XXAA
(SEQ ID NO: 5)
TRTEIIRELEELAKRLKRSLREQERSLREQERLQREGSSDEDVRK
LAREQKKLAREQKELVEEIEYLVEELKRQD Polypeptide Nomenclature:

The name of the polypeptides shown below indicates oligomerization state and topology, and sequences below are organized by topology and oligomerization state. The first two characters indicate supercoil geometry: '2L' refers to a two-layer heptad repeat that results in a left-handed supercoil; '3L' refers to a three-layer 11-residue repeat with a right-handed supercoil; and '5.' refers to untwisted designs with a five-layer 18-residue repeat and straight helices (no supercoiling), where "layer" in this context is the number of unique repeating geometric slices, or layers, along the supercoil axis. The middle two characters indicate the total number of helices, and the final two indicate symmetry. Thus, "2L6HC3" denotes a left-handed, six-helix trimer with C3 symmetry. Underlined residues are optional.

2L8HC4_12
(SEQ ID NO: 6)
GTAIEANSRMLKALIEIAKAIWKALWANSLLLEATSRGDTERMRQ
WAEEAREIYKEAKKIIDEADEIVKEAKERHD

5L6HC3_1
(SEQ ID NO: 7)
SEELRAVADLQRLNIELARKLLEAVARLQELNIDLVRKTSELTDE
KTIREEIRKVKEESKRIVEEAEEEIRRAKEESRYIADESRGS

2L4HC2_9
(SEQ ID NO: 8)
GTSDYIIEQIQRDQEEARKKVEEAEERLERVKEASKRGVSSDQLL
DLIRELAEIIEELIRIIRRSNEAIKELIKNQS

2L4HC2_11
(SEQ ID NO: 9)
GSEDYKLREAQRELDKQRKDTEEIRKRLKEIQRLTDERTSTADEL
IKELREIIRRLQEQSEKLREIIEELEKIIRKR

2L4HC2_23
(SEQ ID NO: 10)
GTRTEIIRELERSLREQEELAKRLKELLRELERLQREGSSDEDVR
ELLREIKELVEEIEKLAREQKYLVEELKRQD

2L4HC2_24
(SEQ ID NO: 11)
GTDTDELLRLAKEQAELLKEIKKLVEEIARLVKEIQEDPSDELLK
TLAELVRKLKELVEDMERSMKEQLYIIKKQKS

5L8HC4_6
(SEQ ID NO: 12)
GSKDTEDSRKIWEDIRRLLEEARKNSEEIWKEITKNPDTSEIARL
LSEQLLEIAEMLVRIAELLSRQTEQR

2L6HC3_AXAX
(SEQ ID NO: 13)
GTKYEIREALKEAQKQLEDLKRMLDELRRNLEELKRNPSEDALVE
NNELIVRVLEVIVENNRSIIEILKLLAKSD

2L6HC3_AXBX
(SEQ ID NO: 14)
GTKYKIREMLEEAKRSLEELRRILEKLKESLRELRRNPSEDALVN
NNEVIVKAIEASVENQRIIIELARMLAESD

2L6HC3_AXXB
(SEQ ID NO: 15)
GTKYRIKDTLRELKRALEELKKILEELQRSLEELRRNPSEDALVN
NNEVIVKAIEAAVRAIEISAENQRMLAESD

-continued

2L6HC3_XAAA
(SEQ ID NO: 16)
GTKYEARKQLEEMKKQLKDLKRSLERLREILERLEENPSEDVIVE
AIRAIVENNKQIVENNRSIIENNETIIRSD

2L6HC3_XBXA
(SEQ ID NO: 17)
GTKYELRRQLEELEKLLRELRKSLDELRKILEELERNPSEDVIVR
AIKASVKNQEIIVEVLRAIIENNKTIAKSD

2L6HC3_12
(SEQ ID NO: 18)
GTKYELRRALEELEKALQELREMLRKLKESLEELKKNPSEDALVR
NNELIVEVLRVIVEVLSIIARVLEINARSD

2L6HC3_13
(SEQ ID NO: 19)
GTKYELRRALEELEKALRELKKSLDELERSLEELEKNPSEDALVE
NNRLNVENNKIIVEVLRIIAEVLKINAKSD

2L6HC3_6
(SEQ ID NO: 20)
GTKYKIKETLKRLEDSLRELRRILEELKEMLERLEKNPDKDVIVE
VLKVIVKAIEASVENQRISAENQKALAESD

2L6HC3_10
(SEQ ID NO: 21)
GTKYEIKKALKELEEAIQKLKKSLKELKESLKELQKNPSEDALVK
NNSLNVANNEIIVEVLEIIARILELLARSD

2L6HC3_11
(SEQ ID NO: 22)
GTKYEIKEALRELNRALKELKEALRELERSLRELQKNPDKDALVR
NNELNVDVARIIVEVLSIIARVLELLAKSD

2L6HC3_12
(SEQ ID NO: 23)
GTKYELRRALEELEKALQELREMLRKLKESLEELKKNPSEDALVR
NNELIVEVLRVIVEVLSIIARVLEINARSD

2L6HC3_13
(SEQ ID NO: 24)
GTKYELRRALEELEKALRELKKSLDELERSLEELEKNPSEDALVE
NNRLNVENNKIIVEVLRIIAEVLKINAKSD

2L6HC3_14
(SEQ ID NO: 25)
GTKYELREAIRKLEEALRKLKKALDELRKSLEELKKNPSEDALVR
NNELNVKVAEIIVKVLKIIAEAIKINAKSD

2L6HC3_19
(SEQ ID NO: 26)
GTEEYKLRELLKRHNEVLKELQKAAKEAEEVAERFKKTNDITEAI
RVIADLLRAIVKAIETNSRVVKMIVELNE

2L6HC3_2
(SEQ ID NO: 27)
GTKYIEKLLREAQRTLEELKRLLEELKEMLKELERANATDARLIA
EVIRVIVEVLRASVENQEMIIRILKAITEE

2L6HC3_23
(SEQ ID NO: 28)
TEKDVLRIIVKNNEIIVKVLSVIAEVLKIIAKILENPSEYMLKEL
KKALKELEKMLKELRKSLKELKEALRELEGS

2L6HC3_37
(SEQ ID NO: 29)
GTLDYKLDEMLKKLEKSREEMEKMAQELRRALEELEKNSNVDKVL
KIIIKAIQLSIENQKLNLEAVRLLIEAQKS

2L6HC3_6
(SEQ ID NO: 30)
GTKYKIKETLKRLEDSLRELRRILEELKEMLERLEKNPDKDVIVE
VLKVIVKAIEASVENQRISAENQKALAESD

2L8HC4_3
(SEQ ID NO: 31)
GTDEYKWKEEVRRFEEEAKKWEEELKEMRKRIEDAKKGRPTLKVN
LEAAEEALLEAARLIVEAAKLLLAAAKLNEKQN

2L8HC4_9
(SEQ ID NO: 32)
GSDEDRKAKELIERQRKLTDEAEEWAKQNEEIAKKIEKQPDTSLV
ARMLANVSRMLLATNRALLANTEALEALIRKT

2L8HC4_12
(SEQ ID NO: 33)
GTAIEANSRMLKALIEIAKAIWKALWANSLLLEATSRGDTERMRQ
WAEEAREIYKEAKKIIDEADEIVKEAKERHD

3L6HC2_4
(SEQ ID NO: 34)
SALEKIAKLIIEAARLSAELARRAARASAEMARKAIEAVSEERGS
ESLLKIVADLIVESQEAVVRLIIESQQIAAKLAEDLIRAAKEAAS
DESKMEEVAKEVQERAERAARDIERKLKRVLEELDYKLKESRDGS

3L6HC2_6
(SEQ ID NO: 35)
TALEIAVRLNREAAREAARENADTARKAARRIAEVAKRLAEENRD
AKLAARLLAEIARLLAELIARQSELLAEWLATQSKLAAELARKDT
SATDEAERIRKESEELLDKVREEIKRLEDEVSKTIEELSERVRGS

3L6HC2_7
(SEQ ID NO: 36)
SILELAHESNRRALEMASRANREAMKAAREMIRAASEAARRAGSS
NDKDSLRMIEEALRLALRMIEETNKKAVRMVLENNRKMVEAEKKK
LSEEEIKRIAKETEDRMREIARRASEEARRLAEEIKREADYRSGS

5L6HC3_1
(SEQ ID NO: 37)
SEELRAVADLQRLNIELARKLLEAVARLQELNIDLVRKTSELTDE
KTIREEIRKVKEESKRIVEEAEEEIRRAKEESRYIADESRGS

5L6HC3_3
(SEQ ID NO: 38)
GTERKDRLRKELKRIAEETDKWVEELKEELERILRTIEELRKDPS
SEVIVDIARIQLEALREVIRVVAENSKAILEAIHRVIEEG

5L6HC3_5
(SEQ ID NO: 39)
SKEVRLQKLNAEIMKEIMELIIRLQEANARIIEELVRLIIDLERS
TDSKRMIEEIRKVAERAIEESKRLLEEAEKAMRRAIYESEDALRE
GS

5L8HC4_1
(SEQ ID NO: 40)
GSKVEELLRKSEEAAERAKRELERLLEESERIVAEAQALAEKYES
QKVWVRILIELIRATNRMLAEIARILLEMIEVTNRMIAESTK

5L8HC4_2
(SEQ ID NO: 41)
SEQLKEIARILIKLIESLTRFILEVARILIELIEETQRLIVASTD
SDESELERIARESKKKAKKALDELKKIVDDQRREAKKAIEELEYD
GS

5L8HC4_6
(SEQ ID NO: 42)
GSKDTEDSRKIWEDIRRLLEEARKNSEEIWKEITKNPDTSEIARL
LSEQLLEIAEMLVRIAELLSRQTEQR

2L4HC2_1
(SEQ ID NO: 43)
GTAYELLRKAEELEKKQQELLKRQEELAKTAEELRKKGGNADSMM
KIIKESTRIVRESTEIVKELLKIIRELRRQS

2L4HC2_5
(SEQ ID NO: 44)
GTRTEYLKKLAEEAKELAKRSRELSKESRRLSEEARRDPDKEKLL
RVVKKLQEVIEELQRVIEELLRVIKEALENQS

2L4HC2_6
(SEQ ID NO: 45)
GTETEYQRELAREARTLAKRSRELSERSRKLSEDAKRDPDKDKLL
EVVERLQQVIEELQKVIEELLRVIESSLKTIS

2L4HC2_9
(SEQ ID NO: 46)
GTSDYIIEQIQRDQEEARKKVEEAEERLERVKEASKRGVSSDQLL
DLIRELAEIIEELIRIIRRSNEAIKELIKNQS

-continued

2L4HC2_10
(SEQ ID NO: 47)
GTEEYRRKEQEERTKEQQERTERQRRKTEELKRATKEGTLTPEEA
IRQAQKQSENAERQSREAEKQSREANEALRKR

2L4HC2_11
(SEQ ID NO: 48)
GSEDYKLREAQRELDKQRKDTEEIRKRLKEIQRLTDERTSTADEL
IKELREIIRRLQEQSEKLREIIEELEKIIRKR

2L4HC2_12
(SEQ ID NO: 49)
GSEDYKLKELQKRNKKQEEEAKRNDDERKKIEELTRKRTSTADEL
IRELQRSNEEMQRSQREMQDQSRRLEDIIRKR

2L4HC2_14
(SEQ ID NO: 50)
GTEDYKRREAERKLQKQQEELKELKRKLEEIRELHEKGVGSPDRL
IRELERIIRELQRMQKENEKIIKELQRIIKKR

2L4HC2_18
(SEQ ID NO: 51)
GTESKYLLEEARRLKDEARKLKEEAKKVKEESRKLIERIDRGEDS
DRELLERLKEQNNRLLEIIERLLEIIERLLKLIEEWTRDS

2L4HC2_19
(SEQ ID NO: 52)
GTEEDYAEREIRKMKEEQKRQRKRLEELERELQEMQEKKREGTSD
AKEVIDQLERIIRELQEIIRSQEDITRKLEEIIRRMKENS

2L4HC2_20
(SEQ ID NO: 53)
GTNKEELKRTMEEQQRILEKLLRTIKEQKEILRKQEEGRATKEEL
KRLTKLAQEQERMMRELIDLARKQAYLLKRES

2L4HC2_21
(SEQ ID NO: 54)
GTREEKIRRILEEIQKIMEEIKRIMEEIKRTQEEAEKHGSSKKAI
EKQKELLRRLEELLRKLERLLRELEYLMRDEK

2L4HC2_22
(SEQ ID NO: 55)
GTREEWLYRILELIERIERLIKEIIRLSRRALELLENNASNEEWA
QEIKEMQRKIQEWLKQILEWLKKIKEWIRESQ

2L4HC2_23
(SEQ ID NO: 56)
GTRTEIIRELERSLREQEELAKRLKELLRELERLQREGSSDEDVR
ELLREIKELVEEIEKLAREQKYLVEELKRQD

2L4HC2_24
(SEQ ID NO: 57)
GTDTDELLRLAKEQAELLKEIKKLVEEIARLVKEIQEDPSDELLK
TLAELVRKLKELVEDMERSMKEQLYIIKKQKS

5L4HC2_1
(SEQ ID NO: 58)
GTEETKNSKRVLDIIEELMRQVEENSRELEKRIKELLRQTKEGKT
KKELERDVRRTIEEQKKELRRLKEQVRKTKEEQREEQYRS

5L4HC2_2
(SEQ ID NO: 59)
GTRTEKLMKEVEEIQRRQIELLKKLMKEVEDSSKRNQEATERGTT
KKKWKEEQEKILEDLKREVRRIIEESRKWLEDLKKKVYES

5L4HC2_3
(SEQ ID NO: 60)
GTEKYRLREEVRRTIEEQKENLERLKQEVKETERKTEEWRERNTT
TEDAQREQIKIIRRLMKEVERNSRRLEKELRRLVEETRES

5L4HC2_6
(SEQ ID NO: 61)
GTEKYRLIRESERALRELKRKVRELEEDQRERLDEQRKKVEEGQT
TDELLRQNEENSRRMLKETKKLLREIERIQREQQRQNQEN

5L4HC2_7
(SEQ ID NO: 62)
GTEKEKEIEKNSREVIKQVEDILRIKENSKRNIEIIKELQKDPSD
EKMRETIEQQRENLERLERKARELIRRQERNLRETQYKD

5L4HC2_9
(SEQ ID NO: 63)
GTEKYRIIEEQRRNLEDLEREIREIIKKLKEALERLRELVERNST
NDRLLDEVRKIIEEAIEDMKRLLEKVERSIRQNIEELRRS

5L4HC2_10
(SEQ ID NO: 64)
GTNKEYLRRKVKELKDQQKRNLEELEREVRRLIKEIEEWRERNTT
TDRALKEIIRQIQRLLEEARRNSEEVLRQIEEIMEETRES

5L4HC2_11
(SEQ ID NO: 65)
GTEEERALERIIRAIRELMREVERNSKEVLQWIKEMLRLTKENSS
TKELEERWREIEERQRRNLEKLKEEVRRLEDEIRQETYRS

5L4HC2_12
(SEQ ID NO: 66)
GTETKKLVEEVERALRELLKTSEDLVRKVEKALRELLELIRRGGT
KDKIEEKIRRVLEEIKRELERQKRKIEDVLRQIKEELYRS

2L6Hanti_1
(SEQ ID NO: 67)
SDYLRLATEHNKLAVEANRLAIELAKSAVELAETDPSKTALEHAE
LAARLLEMMVQFTKAAQELTREAIRKEGRNEESEKVLRKSKEAYK
ESEKALEDARRLLDELRKKGS 2L6Hanti_2
(SEQ ID NO: 68)
SEELRKAAENNELAVRLAEAALRMARSALHLFEENPSDEMLKFLE
LAMEVAKMAAELLKASLKMLKKAAEERGSDESVKYLADKSRDIMR
QITEELKKLEEEAKRAQKRGS 2L6Hanti_3
(SEQ ID NO: 69)
SEKARIAVENLEAALRLNRAAAEMQKSAIKIMDDNRSDEKALRYL
RLTTKVLRMSVELLRASLELAEKALREEGSDDSAEKVRKEAEEIL
KESTEILKEADKETKRADEEGS 2L6Hanti_4
(SEQ ID NO: 70)
SRRLELAARINKAAAENARSAIEIQELAARLADELSSSKKVIDFA
RATTEVLRMSVKLLKLSLEMLEEAARQDGRSEEVRYLAEESKKIL
EEARKALEDADRLTKRIEEEGS 2L6Hanti_5
(SEQ ED NO: 71)
TDVLRIAAENLKAAVELAKAALEMAKSAIEIAKTLTEDDEALKFA
RAAAEVLRMAAKLLKLSIELARKAAEEEGSDDEVRYILDEARKQA
DELREALKKVDEIMKELDKRGS 5H2LD_10
(SEQ ID NO: 72)
TRRKQEMKRLKYEMEKIREETEEVKKEIEESKKRPQSESAKNLIL
IMQLLINQIRLLALQIRMLALQLQE 5H2LD_13
(SEQ ID NO: 73)
TEDQERLRKQMEYERKHTEKVEKEIRKVEQKMKSHEDTSLRLLVL
IARLLINQIRLLILQIRSLSNLERN 5H2LD_15
(SEQ ID NO: 74)
TESTLLILIMRLLVQQSELLQLQIQMLQLLLKANNGTNKTEIERR
SKEMEEELKRMKESNREMTKRIKEME 5H2LD_18
(SEQ ID NO: 75)
TESDLLRQISKLLIIQIRLLLLQIQMLILLLKMNTGTNTTQITKE
AKRIEKEAQEARKELEKMQESNKKQT 6H2LD_8
(SEQ ID NO: 76)
TEDEIRKLRKLLEEAEKKLYKLEDKTRRSEEISKTDDDPKAQSLQ
LIAESLMLIAESLLIIAISLLLSSRNG 7H2LD_3
(SEQ ID NO: 77)
TEDEELQRVEEEIRELERKAKELHYKSEEIRKKVNGRSPQAEALL
MIAQALLNISESLLAIAKALLMIARST -continued 8H2LD_4
(SEQ ID NO: 78)
TDEREIIKRVKRLLEEVEYLIERLRDQIEKAEKGLLDSRKAQQNA
EALVNLIKAMVLVLKALLLAKELER 8H2LD_4_KE
(SEQ ID NO: 79)
TEEQYIIEEVKKLLEEVKKLIEELKKQIEKAEKGEEDSRKAQQNA
EALVNLIKAMVLVLKALLLAKELER To probe the energetic contribution of the outer ring of helices, the stability of the two-ring designs was compared to corresponding designs with only the inner ring; core interface positions of the inner helices, including hydrogen bond network residues, were retained and solvent-exposed surface positions were redesigned in the same manner as the surface of the two-ring designs. 2L4HC2_9 (FIG. 2C), a supercoiled homodimer is folded and thermostable (FIG. 2D); its inner helix peptide, 2L4HC2_9 inner (FIG. 2E), also forms a homodimeric coiled-coil, but with markedly decreased thermostability (FIG. 2F). 2L6HC3_13 (FIG. 2G), a supercoiled homotrimer is also folded and thermostable (FIG. 2H); however, the corresponding inner ring peptide (FIG. 2I) in isolation is unfolded (FIG. 2J) and monomeric. The sequence of this inner helix is notable because it has four Asn residues at canonical a or d heptad packing positions where Asn is destabilizing, and also because its other a and d positions are Leu and Ile respectively, which has been found to favor homotetramers. In the presence of the outer helix and designed hydrogen bond networks, the two-ring design assembles to the intended trimeric structure as elucidated by x-ray crystallography (FIG. 3A). Together, these results suggest that the outer ring of helices not only increases thermostability but also can drive coiled-coil assembly, even in the context of an inner helix with low helical propensity and non-canonical helical packing, permitting greater sequence diversity across larger interfaces.

Structural Characterization

To assess the accuracy of the designs, ten crystal structures were determined spanning a range of oligomerization states, superhelical parameters, and hydrogen bond networks (FIG. 3A-F). Designs for which crystals were not obtained were characterized by small angle x-ray scattering (SAXS) (FIG. 4). Structures for three left-handed trimers, four left-handed dimers, a left-handed tetramer, and an untwisted triangle-shaped trimer were solved. Additional topologies characterized by SAXS include square-shaped untwisted tetramers (FIG. 4A) and dimers (FIG. 4B), as well as six-helix dimers (two inner, one outer helix) with either parallel right-handed (FIG. 4C) or antiparallel left-handed (FIG. 4D) supercoil geometry. Five of the x-ray crystallography-verified designs (FIG. 3A,C-F) were also characterized by SAXS, and the experimentally determined spectra were found to closely match those computed from the design models, suggesting that very similar structures are populated in solution.

The three left-handed trimer structures (2L6HC3_6, 2L6HC3_12, and 2L6HC3_13) are remarkably similar to the design models with sub-angstrom RMSD across all backbone Cα atoms and across all heavy atoms of the hydrogen bond networks (FIG. 3A-B). These structures are constructed with supercoil phases of 0, 120 and 240 degrees for the inner helices, and 60, 180, and 300 degrees for the outer helices; loops connect outer N-terminal helices to inner C-terminal helices (at −60 degrees from the outer helix). Extensive nine or twelve-residue networks form the intended hydrogen bonds in the crystal structures (FIGS. 3, A and B middle). Unlike previously designed single-ring trimers where three buried asparagines resulted in substantially decreased thermostability, these two-ring trimers are stable up to 95° C. and ~4.5M guanidinium chloride with numerous buried polar residues; 2L6HC3_13 has twelve completely buried asparagines, and 2L6HC3_6 has 24 buried polar residues confined to a small region of the interface, including six asparagines and six glutamines.

The four left-handed dimer crystal structures (2L4HC2_9, 2L4HC2_23, 2L4HC2_11, and 2L4HC2_24) all have the designed parallel two-ring topology. Two of the dimer structures have hydrogen bond networks in close agreement to the designs: 2L4HC2_9 (FIG. 3D) and 2L4HC2_23 (FIG. 3E) have 0.39 Å and 0.92 Å RMSD across all network residue heavy-atoms, respectively, and 0.39 Å and 1.16 Å RMSD over all Cα atoms. The other two, 2L4HC2_11 and 2L4HC2_24, have slight structural deviations from the design models caused by water displacing designed network sidechains; in the former, the interface shifts ~2 Å due to a buried water molecule bridging two network residues, and in the latter, the backbone is nearly identical to the design model but sidechains of the designed network are displaced by ordered water molecules. These two cases highlight the need for high connectivity and satisfaction (all polar atoms participating in hydrogen bonds) of the networks. The lefthanded tetramer structure has the designed overall topology (FIG. 3C), and SAXS data is in close agreement with the design model, but sidechain density was uncertain due to low (3.8 Å) resolution. The amino acid sequence is unrelated to any known sequence, and the top hit in structure-based searches of the Protein Data Bank (PDB) has a quite different helical bundle arrangement.

The five antiparallel six-helix dimers (2L6Hanti_1-5) were soluble and assembled to the designed oligomeric state, with SAXS data in agreement with the design models (FIG. 4D). Design 2L6Hanti_3 contains a hydrogen bond network with a buried Tyr at the dimer interface (FIG. 4D). Of the three right-handed six-helix dimers characterized by SAXS, 3L6HC2 4 (FIG. 4C) and 3L6HC2 7 exhibited scattering in agreement with the design models, whereas 3L6HC2 2 did not. While 3L6HC2 2 was designed to form a parallel dimer, its crystal structure revealed an antiparallel dimer interface, highlighting two design lessons: first, the importance of intermolecular hydrogen bonds at the binding interface (the 3L6HC2 2 design model has only two across the interface compared to 9 in 2L6HC3_6 (FIG. 3B)), and second, the importance of favorable hydrophobic contacts complementing the networks (the 3L6HC2 2 design model has mainly alanines at the interface).

SAXS data suggest that untwisted dimer, trimer and tetramer designs assemble into the target triangular and square conformations (FIG. 4A-B). Guinier analysis and fit of the low-q region of the scattering vector indicates that the seven untwisted dimers tested are in the correct oligomeric state, four of which have very close agreement between the experimental spectra and design models (FIG. 4B). The SAXS data on the three untwisted tetramers (5L8HC4_1, 5L8HC4_2, and 5L8HC4_6) were all in close agreement with the corresponding design models (FIG. 4A). 5L8HC4_6 has a distinctive network with a Trp making a buried hydrogen bond at one end of the network, which then propagates outwards towards solvent, connecting to an Glu on the surface (FIG. 4A). It is believed that oligomers with such uniformly straight helices do not exist in nature, nor have these topologies been designed previously.

The 2.36 Å crystal structure of the untwisted trimer (5L6HC3_1) reveals straight helices with 0.51 Å RMSD to the design model over all Cα atoms (FIG. 3F). The two hydrogen bond networks (FIG. 3F middle), as well as the hydrophobic packing residues surrounding the networks (FIG. 3F right), are nearly identical between the crystal structure and design model, with 0.41 Å and 0.48 Å RMSD over all network heavy-atoms. Like the supercoiled trimers, each of these networks contains sidechains from every helix, and helices were constructed to be uniformly symmetrical and equidistant. The helices are nearly perfectly straight in the crystal structure with supercoil twist values very close to the idealized design value of zero: $\omega_0=-0.036$ degrees/residue for the inner three helices and to $\omega_0=-0.137$ degrees/residues for the outer three helices. Blast searches with the amino acid sequence returned no matches with E-values better than 10, and the top hit in a search for similar structures in the PDB has three supercoiled helices flanked by long extended regions.

Comparison of Successful Versus Unsuccessful Network Designs

Several trends emerged distinguishing successful designs. First, in successful designs nearly all buried polar groups made hydrogen bonds. Designs with all heavy atom donors and acceptors satisfied were selected, but the networks had varying numbers of polar hydrogens unsatisfied. Networks with the largest fraction of satisfied polar groups generally had relatively high connectivity, both with respect to the total number of hydrogen bonds and number of sidechains contributing to the network. Networks with the highest connectivity and structural accuracy were those that spanned the entire cross-sectional interface, with each helix contributing at least one sidechain (FIG. 3A, 3B, 3E, 3F). Design 2L6HC3_13 also has two additional smaller networks comprising a single symmetric Asn making two hydrogen bonds but with one polar hydrogen unsatisfied; in the crystal structure, these residues move away from the design model, displaced by water molecules.

The Designed Hydrogen Bond Networks Confer Specificity

To test the role of the designed hydrogen bond networks in conferring specificity for the target oligomeric state, control design calculations were carried out using the same protein backbones without HBNet™, yielding uniformly hydrophobic interfaces. In silico, despite having lower total energy in the designed oligomeric state, these designs exhibit more pronounced alternative energy-minima in fold-and-dock and asymmetric docking calculations, consistent with the much less restrictive geometry of nonpolar packing interactions. Experimentally, these hydrophobic designs exhibited less soluble expression than their counterparts with hydrogen bond networks and tended to precipitate during purification; of those that remained in solution long enough to collect SEC-MALS data, all but one formed higher molecular weight aggregates, eluting as multiple peaks from the SEC column. These results suggest that the designed hydrogen bond networks confer specificity for the target oligomeric state and resolve the degeneracy of alternative states observed with purely hydrophobic packing (this degeneracy is considerably more pronounced for herein-described 2 ring structures than traditional single ring coiled coils, which have many fewer total hydrophobic residues and less inter-helical interface area).

An in vivo yeast-two-hybrid assay was used to further probe the interaction specificity of the designed oligomers. Sequences encoding a range of dimers, trimers, and tetramers were crossed against each other in all-by-all binding assays (FIG. 5); synthetic genes for the designs were cloned in frame with both DNA-binding domains and transcriptional activation domains in separate vectors such that binding of the designed protein interaction is necessary for cell growth. Designs in which the hydrogen bond networks partition hydrophobic interface area into relatively small regions are considerably more specific than designs with large contiguous hydrophobic patches at the helical interface (FIGS. 5, A and B). The designs with the best-partitioned hydrophobic area had networks spanning the entire oligomeric interface, with each helix contributing at least one sidechain. This unifying design principle can readily be enforced using HBNet™.

To test if regular arrays of networks can confer specificity in a modular, programmable manner, an additional set of trimers were designed, each with identical backbones and hydrophobic packing motifs, the only difference being placement and composition of the hydrogen bond networks. The designs are based on 2L6HC3_13 (FIG. 3A) and 2L6HC3_6 (FIG. 3B), which originated from the same superhelical parameters but have unique networks referred to as "A" and "B", respectively; cross-sections with only nonpolar residues are labeled "X". This three-letter code was used to generate new designs in combinatorial fashion: at each of the 4 repeating cross-sections of the supercoil (FIG. 5C), either the A, B, or X (FIG. 4D) were placed followed by the same design strategy and selection process as before. Six of these combinatorial designs were synthesized and 5/6 were found to be folded, thermostable, and assembled to the designed trimeric oligomerization state in vitro. These five, along with the two parent designs (2L6HC3_13=AAXX and 2L6HC3_6=XXBB) and an all-hydrophobic control (XXXX), were crossed in all-by-all yeast-two-hybrid binding experiments (FIG. 5E). The combinatorial designs exhibit a level of specificity that is striking given that all have identical backbones and high overall sequence similarity, whereas the hydrophobic control is relatively promiscuous; the central hydrogen bond networks are clearly responsible for mediating specificity.

Previous de novo protein design efforts have focused on jigsaw-puzzle-like hydrophobic core packing to design new structures and interactions. Unlike the multi-body problem of designing highly connected and satisfied hydrogen bond networks, hydrophobic packing is readily captured by established pairwise-decomposable potentials; consequently, most protein interface designs have been predominantly hydrophobic, and attempts to design buried hydrogen bonds across interfaces have routinely failed. Polar interfaces have been designed in specialized cases but have been difficult to generalize, with many interface design efforts requiring directed evolution to optimize polar contacts and achieve desired specificity. HBNet™ now provides a general computational method to accurately design hydrogen bond networks. This ability to precisely pre-organize polar contacts without buried unsatisfied polar atoms should be broadly useful in protein design challenges such as enzyme design, small molecule binding, and polar protein interface targeting.

Two-ring structures are a new class of protein oligomers that have the potential for programmable interaction specificity analogous to that of Watson-Crick base paring. Whereas Watson-Crick base pairing is largely limited to the antiparallel double helix, the designed protein hydrogen bond networks allow the specification of two-ring structures with a range of oligomerization states (dimers, trimers, and tetramers) and supercoil geometries. Adding an outer ring of helices to enable hydrogen bond networks extends upon elegant studies from Keating, Woolfson, and others demonstrating the designability of coiled coils with a wide range of hetero and homo-oligomeric specificities. The design models and crystal structures show that a wide range of hydrogen bond network composition and geometry are possible in repeating two-ring topologies, and that multiple networks can be engineered into the same backbone at varying positions without sacrificing thermostability, enabling stable building blocks with uniform shape but orthogonal binding interfaces (FIG. 5). The DNA nanotechnology field has demonstrated that a spectacular array of shapes and interactions can be built from a relatively limited set of hydrogen bonding interactions. It should now become possible to develop new protein-based materials with the advantages of both polymers: DNA-like programmability and tunable specificity, coupled with the geometric variability, interaction diversity, and catalytic function intrinsic to proteins.

Computational Techniques

Computational techniques related to protein design based on a Hydrogen Bond Network method (HBNet™) are described in detail below. The HBNet™ method can include three steps. First, an exhaustive but efficient search identifies the hydrogen bond networks possible within a given search space (which consists of all allowed sidechain rotamers of all amino acid types being considered for a particular backbone conformation). Second, networks are scored and ranked based on the Rosetta™ energy function, satisfaction (all buried polar atoms participating in hydrogen bonds), and user-defined options. And, third, the best networks, or combinations of the best networks, are iteratively placed onto the design scaffold and held in relative position with constraints that serve as 'seeds' for any subsequent Rosetta™ method to design around the network and optimize rotamers for the remaining positions in the scaffold.

Step 1. Exhaustive Search to Identify all Possible Hydrogen Bond Networks in the Given Search Space (FIG. 1A-B).

HBNet™ makes use of Rosetta™'s Interaction Graph (IG) data structure, initially populating it with only the sidechain hydrogen bond and Lennard-Jones (steric repulsive) energy terms. The nodes of the graph are the residue positions of all designable or packable residues, and the edges represent putative interactions between those residues, pointing to sparse matrices that store the two-body energies between all pairs of interacting rotamers (of all amino acid types being considered) at those two positions. Only using the hydrogen bond and repulsive energies allows for instant look-up of all rotamer pairs with favorable (low energy) hydrogen bond geometry and no steric clashing. In some embodiments, Monte Carlo or similar randomized methods can be used to search this rotamer interaction space.

In other embodiments, the entire rotamer interaction space can be searched. The search through the entire rotamer interaction space can be performed using a recursive depth-first search or a recursive breadth-first search of the interaction graph, enumerating all compatible, non-clashing connectivities of hydrogen bonded sidechain rotamers. Since the search traverses not only the nodes of the graph, but also matrices pointed to by each edge (multiple rotamers per each node, and multiple pairs of rotamers for each edge), implementation of a graph traversal algorithm for this graph can consider connected nodes (residues positions) of networks as well as considering hydrogen bonds between atoms of particular rotamers at each node—this latter hydrogen-bond criteria requires additional steps and behavior for this graph traversal algorithm.

Each time a new hydrogen bonding rotamer is considered, the graph traversal algorithm can check the rotamer to ensure it does not clash with any existing rotamers in that network. If it is accepted, a recursive call is made on this rotamer. These recursive calls continue until a stop condition is reached: either no additional hydrogen bonding interactions can be found, or the network connects back to one of the original starting residues.

Some polar amino acids, such as Asn and Gln, can make three or more hydrogen bonds, serving as branch points in hydrogen bond networks; depth-first search misses these branching amino acids, and to account for this, a look-back function identifies networks that share one or more identical rotamers and, after checking for clashes or conflicting residues, merges them together into complete networks. Redundant networks are eliminated.

An instance of HBNet™, "HBNetStapleInterface™", was written, in which graph traversals are initiated at residue positions at the intermolecular interface. This implementation of HBNet™ offers two advantages: first, starting the traversal at only the interface positions reduces the search space, speeding up runtime, and second, it ensures only networks at the interface are found, which was the goal of the approach in this study; requiring that at least 2 residues in each network come from different polypeptide chains ensure that network spans the intermolecular interface. For each starting residue, HBNetStapleInterface™ iterates through each edge; at each edge, networks are initiated for rotamer pairs with interaction energies less than a threshold value (default=−0.75). Because the interaction energy only consists of hydrogen bonding and repulsive contributions, a positive energy indicates clashing, and a negative energy indicates hydrogen bonding; setting a threshold allows for both selection of hydrogen bonds with favorable (low energy) geometry and faster computational runtime—because of the multiple recursive steps, runtime is exponential dependent upon the number of hydrogen bonding rotamer pairs (which increases as the threshold is made less stringent). The total number of hydrogen bonding rotamer pairs differs vastly between input structures and cannot be calculated ahead of time; through extensive empirical testing, threshold values were found ranging from −0.65 to 0.85 resulted in favorable hydrogen bonds and runtimes on the order of ~0.2-10 minutes for complete design runs that included downstream design of numerous network possibilities for a given input structure.

Step 2. Score and Rank all of the H-Bond Networks.

Once all possible networks are identified, the identified networks are scored and ranked to determine the "best" networks. For each network, buried polar atoms are identified by solvent-accessible surface area (SASA); networks with buried heavy atom donors or acceptors not making hydrogen bonds (unsatisfied) are eliminated. The remaining networks are then ranked based on the least number of unsatisfied polar hydrogens. The networks are then scored against each other in the context of a background reference structure: all designable or packable positions in the scaffold are mutated to poly-alanine, network rotamers placed onto the scaffold, and the network scored with the full Rosetta™ energy function (talaris2013).

During Step 1, sidechain-backbone hydrogen bonds are not explicitly considered because the backbone is fixed (the number of sidechain-backbone hydrogen bonds for any given rotamer is constant). During Step 2, sidechain-backbone hydrogen bonds are scored when the networks are placed onto the reference structure, and are therefore included in evaluation for satisfaction (how many of the buried polar atoms participate in hydrogen bonds). Thus, even though they are not searched for explicitly, HBNet™ captures networks with sidechain-backbone hydrogen bonds. Networks with additional hydrogen bonds to backbone polar atoms will generally score better than a similar network without h-bonds to backbone in that the connectivity and satisfaction is improved.

Step 3. For Each of the Best-Scoring H-Bond Networks, Perform Design.

The best networks as ranked by Step 2 are iteratively placed onto the input scaffold and passed back to the RosettaScripts™ protocol and for user-defined design of the remaining residue positions. Atom-pair constraints are automatically turned on for each pair of atoms making a hydrogen bonds in the network; these constraints are tracked throughout the remainder of the design run to ensure the network residues are fixed in relative position during the downstream design. HBNet™ also outputs a Rosetta™ constraint (.cst) file that can be used to specify the same constraints in subsequent Rosetta design runs.

It should be noted that these atom-pair "constraints" in Rosetta™ nomenclature are really "restraints" in that the rotamers are allowed to move, and an energy penalty is applied if the constraint is broken (i.e., if the hydrogen bond is broken). This approach—as opposed to simply fixing the coordinates of the network atoms—allows small movements of the network rotamers, allowing for a larger number of solutions for packing additional rotamers around the network. A trend that emerged that tight packing around the networks, as well as satisfaction of all buried heavy-atom donors and acceptors, is paramount to design success; it is more important to have hydrogen bonds satisfying all polar atoms in the network with mediocre h-bond geometry than it is to have ideal h-bond geometry but poor packing around them and/or unsatisfied donors/acceptors.

Combinations of multiple networks at the same interface can also be considered and specified by the user. Unlike typical Rosetta™ design, in which one input structure yields one output structure (the lowest energy solution found by sequence design and combinatorial sidechain optimization), this approach allows for hundreds of design possibilities to be output for each input structure.

Defining the Search Space (which Amino Acid Types and Sidechain Rotamers are Allowed During Network Search)

HBNet™ will only search for networks within a given search space (all possible rotamers of all possible amino acid types being considered for a given input backbone), which can be defined by the user. HBNet™ functions as a "Mover" within the RosettaScripts™ framework and can be passed "task operations" to specify which residue positions are fixed, packable (amino acid type is fixed but sidechain conformation is not), and designable—for designable positions, task operations can also specify which amino acid types are allowed at each position. The default setting in the absence of any task operations is that all residues are considered for design and all polar amino acids are considered in the network search.

All positions in the scaffold can be set to be designable; for HBNet™, buried positions (defined based on solvent-accessible surface area (SASA)) can be allowed to be any noncharged polar amino acid, and solvent-exposed positions can be allowed to be any polar amino acid.

Computational Design

A generalization of the Crick coiled-coil parameters was used to independently vary parameters of two or more helices supercoiled around the same axis, parameters defined as described previously. Each monomer subunit has at least one inner helix and an outer helix (FIG. 1D). The supercoil phase ($\Delta\varphi_{0\ in}$) and z-offset of the first inner helix were fixed to 0 to serve as a relative reference point; all other parameters varied independently between the inner and outer helices, with the exception of the supercoil twist ($\omega_0$) and helical twist ($\omega_1$). Because these two parameters are coupled and determine handedness, ideal values were used for $\omega_1$ with $\omega_0$ and $\omega_1$ held constant between the inner and outer helices for the majority of designs. A left-handed supercoil results from $\omega 0<0$ and $\omega 1=102.85$, a right-handed supercoil from $\omega_0>0$ and $\omega_1=98.18$, and a straight bundle (no supercoiling) from $\omega 0=0$ and $\omega 1=100$. For the parallel six-helix dimer designs (3L6HC2), which have two inner helices and one out helix, $\omega 0$ of the outer helix was allowed deviate from that of the inner helix, but was required to be positive to maintain a right-handed supercoil.

Additional sets of supercoiled dimer backbones were generated by constraining the pitch of the outer helix to match that of the inner helix via the following equation:

$$\omega_0' = \frac{\omega_0}{\sqrt{\frac{1+\omega_0^2(R'^2-R^2)}{d^2}}}$$

where:
$\omega_0'$: superhelical twist of outer helix
$\omega_0$: superhelical twist of inner helix
R': superhelical radius of outer helix
R: superhelical radius of outer helix
d: rise per residue (set to 1.51)

Constraining the pitch results in the outer helix maintaining more contacts to the inner helices throughout the length of the helical bundle allows for different hydrogen bond network and packing solutions.

HBNet™ is written in C++ as part of the Rosetta™ software suite: HBNet™ was developed to be modular and is compatible with all symmetric Rosetta™ applications, as well as the RosettaScripts™ XML framework so that it can be plugged into most existing design protocols, and users can customize options specific to their design tasks. HBNet™ is written as an abstract base class, from which specialized "mover" classes can be derived for specific design cases. In particular, the instance of HBNet™ described herein as "HBNetStapleInterface™" was written to search for hydrogen bond networks that span across intermolecular interfaces. AB Table 1 shows example RosettaScripts™ XML used for design calculations, example command lines and flags used for design calculations, and customized score weighting information.

TABLE 1

```
<ROSETTASCRIPTS>#Design of symmetric homo-oligomers using HBNet, updated to
work with new XSD
    <SCOREFXNS>
        <ScoreFunction name="hard_symm" weights="talaris2013_cst" symmetric="1">
            <Reweight scoretype="coordinate_constraint" weight="0.5" />
        </ScoreFunction>
```

TABLE 1-continued

```
        <ScoreFunction name="hard_bb" weights="bb_only" symmetric="1">
            <Reweight scoretype="coordinate_constraint" weight="2." />
            <Reweight scoretype="cart_bonded" weight="0.5" />
        </ScoreFunction>
        <ScoreFunction     name="hard_symm_no_cst"     weights="talaris2013"
symmetric="1"/>
    </SCOREFXNS>
    <TASKOPERATIONS>
        <InitializeFromCommandline name="init"/>
        <IncludeCurrent name="current"/>
        <LimitAromaChi2 name="arochi" />
        <ExtraRotamersGeneric name="ex1_ex2" ex1="1" ex2="1"/>
        <ExtraRotamersGeneric name="ex1" ex1="1"/>
        <RestrictAbsentCanonicalAAS name="ala_only" resnum="0" keep_aas="A" />
        <LayerDesign name="init_layers" layer="other" make_pymol_script="0">
            <TaskLayer>
                <SelectBySASA     name="symmetric_inteface_core"     state="bound"
mode="mc" core="1" probe_radius="2.0" core_asa="35" surface_asa="45" verbose="1"/>
                <all copy_layer="core" />
                <Helix append="NQSTH"/>
            </TaskLayer>
            <TaskLayer>
                <SelectBySASA     name="symmetric_inteface_surface"     state="bound"
mode="mc" surface="1"probe_radius="2.0" core_asa="35" surface_asa="45" verbose="1"/>
                <all copy_layer="surface" />
            </TaskLayer>
            <TaskLayer>
                <SelectBySASA     name="symmetric_intefacc_boundary"     state="bound"
mode="mc"    boundary="1"    probe_radius="2.0"    core_asa="35"    surface_asa="45"
verbose="1"/>
                <all copy_layer="boundary" />
                <Helix exclude="EKRW"/>
            </TaskLayer>
        </LayerDesign>
        <SelectBySASA     name="select_core"     state="bound"     mode="mc"     core="1"
probe_radius="2.0" core_asa="35" surface_asa="45" verbose="1"/>
        <SelectBySASA     name="select_boundary"     state="bound"     mode="mc"
boundary="1" probe_radius="2.0" core_asa="35" surface_asa="45" verbose="1"/>
        <SelectBySASA name="select_surface" state="bound" mode="mc" surface="1"
probe_radius="2.0" core_asa="35" surface_asa="45" verbose="1"/>
        <SelectBySASA     name="select_all"     state="bound"     mode="mc"     core="1"
boundary="1"    surface="1"    probe_radius="2.2"    core_asa="35"    surface_asa="45"
verbose="1"/>
    </TASKOPERATIONS>
    <FILTERS>
        <EnzScore     name="cst_score"     score_type="cstE"     scorefxn="hard_symm"
whole_pose="1" energy_cutoff="10.0"/>
        <SymUnsatHbonds name="uhb" cutoff="1000"/>
        <Holes name="holes" threshold="1.8" confidence="0"/>
        <PackStat name="packstat" threshold="0.65" confidence="0"/>
        <PackStat name="init_pstat" threshold="0.575" confidence="0"/>
        <ScoreType     name="cart_bonded_filter"     scorefxn="hard_symm"
score_type="cart_bonded" threshold="30." confidence="1." />
        <Geometry name="geo" omega="165" cart_bonded="35" confidence="1"/>
    </FILTERS>
<MOVERS>
        #define symmetry of homo-oligomer; in this example, it's C3 symmetry
        <SetupForSymmetry name="setup_symm" definition="C3_Z.sym"/>
        <SymPackRotamersMover     name="transform_sc"     scorefxn="hard_symm"
task_operations="ala_only" />
        <AddConstraintsToCurrentConformationMover     name="add_cst"
use_distance_cst="0"max_distance="12." coord_dev="2.5" min_seq_sep="8" />
        <ClearConstraintsMover name="clearconstraints"/>
        <SymMinMover     name="hardmin_bb"     scorefxn="hard_bb"
type="lbfgs_armijo_nonmonotone" tolerance="0.0001" chi="1" bb="1" bondangle="1"
bondlength="1" jump="all" cartesian="1"/>
        #HBNet Mover definition
        <HBNetStapleInterface     name="hbnet_interf"     hb_threshold="-0.75"
upper_score_limit="3.5"    write_network_pdbs="1"    pore_radius="3.5"    minimize="0"
min_helices_contacted_by_network="6"    min_network_size="6"    max_unsat="2"
max_staples_per_interface="4"    combos="2"    stringent_satisfaction="1"
onebody_hb_threshold="-0.3" task_operations="init,current,arochi,ex1_ex2,init_layers" />
        #MultiplePoseMover (MPM) is needed because HBNet will pass back multiple
poses -- one for each network, or combination of networks that is tried
        # The MPM collects all poses passed to it by HBNet, and then runs a nested
ROSETTASCRIPTS protocol iteratively on each pose
        # Constraints are automatically turned on to keep the given network fixed in
relative position during downstream design
        <MultiplePoseMover name="MPM_design" max_input_poses="100">
          <SELECT>
```

TABLE 1-continued

```
        </SELECT>
        <ROSETTASCRIPTS>
            <SCOREFXNS>
                <ScoreFunction name="soft_symm" weights="soft_rep_trp_ala" symmetric="1"/>
                <ScoreFunction name="hard_symm" weights="talaris2013_cst" symmetric="1">
                    <Reweight scoretype="coordinate_constraint" weight="0.5" />
                </ScoreFunction>
                <ScoreFunction name="up_ele" weights="talaris2013" symmetric="1">
                    <Reweight scoretype="fa_elec" weight="1.4" />
                    <Reweight scoretype="hbond_sc" weight="2.0" />
                </ScoreFunction>
            </SCOREFXNS>
            <TASKOPERATIONS>
                <InitializeFromCommandline name="init"/>
                <IncludeCurrent name="current"/>
                <LimitAromaChi2 name="arochi" />
                <ExtraRotamersGeneric name="ex1_ex2" ex1="1" cx2="1"/>
                <ExtraRotamersGeneric name="ex1" ex1="1"/>
                <LayerDesign name="all_layers" layer="other" make_pymol_script="0">
                    <TaskLayer>
                        <SelectBySASA name="symmetric_inteface_core" state="bound" mode="mc" core="1" probe_radius="2.0" core_asa="35" surface_asa="45" verbose="1"/>
                        <all copy_layer="core"/>
                        <Helix append="M"/>
                    </TaskLayer>
                    <TaskLayer>
                        <SelectBySASA name="symmetric_inteface_surface" state="bound" mode="mc" surface="1" probe_radius="2.0" core_asa="35" surface_asa="45" verbose="1"/>
                        <all copy_layer="surface" />
                    </TaskLayer>
                    <TaskLayer>
                        <SelectBySASA name="symmetric_inteface_boundary" state="bound" mode="mc" boundary="1" probe_radius="2.0" core_asa="35" surface_asa="45" verbose="1"/>
                        <all copy_layer="boundary" />
                        <Helix exclude="D"/>
                    </TaskLayer>
                </LayerDesign>
                <SelectBySASA name="select_core" state="bound" mode="mc" core="1" probe_radius="2.0" core_asa="35" surface_asa="45" verbose="1"/>
                <SelectBySASA name="select_boundary" state="bound" mode="mc" boundary="1" probe_radius="2.0" core_asa="35" surface_asa="45" verbose="1"/>
                <SelectBySASA name="select_surface" state="bound" mode="mc" surface="1" probe_radius="2.0" core_asa="35" surface_asa="45" verbose="1"/>
                <ConstrainHBondNetwork name="hbnet_task" />
            </TASKOPERATIONS>
            <MOVERS>
                <SymPackRotamersMover name="softpack_core" scorefxn="soft_symm" task_operations="init,all_layers,select_core,current,arochi,hbnet_task"/>
                <SymPackRotamersMover name="softpack_boundary" scorefxn="soft_symm" task_operations="init,all_layers,select_boundary,current,arochi,hbnet_task"/>
                <SymPackRotamersMover name="softpack_surface" scorefxn="soft_symm" task_operations="init,all_layers,select_surface,current,arochi,hbnet_task"/>
                <SymPackRotamersMover name="hardpack_core" scorefxn="hard_symm" task_operations="init,all_layers,select_core,current,arochi,ex1_ex2,hbnet_task"/>
                <SymPackRotamersMover name="hardpack_boundary" scorefxn="hard_symm" task_operations="init,all_layers,select_boundary,current,arochi,ex1_ex2,hbnet_task"/>
                <SymPackRotamersMover name="hardpack_surface" scorefxn="up_ele" task_operations="init,all_layers,select_surface,current,arochi,ex1,hbnet_task"/>
                <SymMinMover name="hardmin_sconly" scorefxn="hard_symm" chi="1" bb="0" bondangle="0" bondlength="0" />
            </MOVERS>
            <APPLY_TO_POSE>
            </APPLY_TO_POSE>
            <PROTOCOLS>
                <Add mover="softpack_core"/>
                <Add mover="softpack_boundary"/>
                <Add mover="softpack_surface"/>
                <Add mover="hardmin_sconly"/>
```

TABLE 1-continued

```
                <Add mover="hardpack_core"/>
                <Add mover="hardpack_boundary"/>
                <Add mover="hardpack_surface"/>
            </PROTOCOLS>
        </ROSETTASCRIPTS>
    </MultiplePoseMover>
    <MultiplePoseMover name="MPM_min_repack" max_input_poses="100">
<ROSETTASCRIPTS>
            <SCOREFXNS>
                <ScoreFunction    name="hard_symm_no_cst"    weights="talaris2013" symmetric="1"/>
                <ScoreFunction    name="talaris_cart_sym"    weights="talaris2013_cart" symmetric="1"/>
            </SCOREFXNS>
            <TASKOPERATIONS>
                <RestrictToRepacking name="repack_only" />
            </TASKOPERATIONS>
            <MOVERS>
                <SymMinMover    name="hardmin_cart"    scorefxn="talaris_cart_sym" type="lbfgs_armijo_nonmonotone" tolerance="0.0001" chi="1" bb="1" bondangle="1" bondlength="1" jump="ALL" cartesian="1"/>
                <SymPackRotamersMover    name="repack" scorefxn="hard_symm_no_cst" task_operations="repack_only" />
            </MOVERS>
            <APPLY_TO_POSE>
            </APPLY_TO_POSE>
            <PROTOCOLS>
                <Add mover="hardmin_cart" />
                <Add mover="repack" />
            </PROTOCOLS>
        </ROSETTASCRIPTS>
    </MultiplePoseMover>
    #minimize and repack without constrainsts on the network residues; if there is good packing around the networks, they should stay
        # in place in absence of the constraints.
    <MultiplePoseMover name="MPM_filters" max_input_poses="100">
        <SELECT>
            <AndSelector>
                <Filter filter="cst_score"/> #this score represent how much the network moved during repacking without constraints
                <Filter filter="uhb"/> #number of buried unsatisfied polar atoms in the entire pose
                <Filter filter="holes"/> #filter out designs with large cavities
            </AndSelector>
        </SELECT>
    </MultiplePoseMover>
 </MOVERS>
<PROTOCOLS>
        #SETUP THE POSE
        #only do these first steps if starting with the python script parametric bockbones
        #generate the symmetric backbone
        <Add mover="setup_symm"/>
        #transform all sidechains to Ala (need CB for minimization), then minimize with coordinate constraints on the backbone
        <Add mover="transform_sc"/>
        #constraints on the backbone
        <Add mover="add_cst"/>
        #minimize away bad torsions that may be present in the "ideal" generated backbone
        <Add mover="hardmin_bb"/>
        <Add mover="clearconstraints"/>
        #if using BGS, start here and comment out above:
        #NOW LOOK FOR NETWORKS
        #find h-bond networks using HBNet
        <Add mover_name="hbnet_interf"/>
        #EVERYTHING AFTER HERE IS WITH MULTPLE_POSE_MOVER (MPM)
        #design the rest of the pose around the networks
        <Add mover_name="MPM_design"/>
        #minimize and repack without the network csts turn on (this acts as a filter for networks with poor packing around them, or bad sidechains)
        <Add mover_name="MPM_min_repack"/>
        #filters
        <Add mover_name="MPM_filters"/>
    </PROTOCOLS>
</ROSETTASCRIPTS>
```

Design Calculations

Parametrically generated backbones were first regularized using Cartesian space minimization in Rosetta™ to alleviate any torsional strain introduced by ideal backbone generation. For each topology, an initial search of only the inner helix was performed to identify parameter ranges that resulted in the most favorable core sidechain packing; outer helix parameters were then extensively sampled in context of these inner helix parameter ranges, generating tens of thousands of backbones. HBNet™ was used to search these backbones for hydrogen bond networks that span the intermolecular interface, have all heavy atom donors and acceptors satisfied, and contain at least three sidechains contributing hydrogen bonds. For buried interface positions, only non-charged polar amino acids were considered; for residue positions that were at least partially solvent-exposed, all polar amino acids were considered. Finer sampling was performed around backbone parameters that could accommodate both favorable hydrogen bond networks and hydrophobic packing. The helices of monomer subunits were connected into a single chain and the assembled proteins were designed using symmetric Rosetta™ sequence design calculations coupled with HBNet™ (FIG. 1F-G).

Selection Criteria and Metrics Used to Evaluate Designs

For the designs described herein, generally on the order of ~100,000 networks were detected after Step 1, but only a handful of networks, if any, passed all of the criteria outlined in Step 2 and were carried forward. After downstream design (Step 3), packing around the networks was evaluated. Because the hydrogen bond networks are constrained during downstream design, models were minimized and sidechains repacked without the constraints to measure how well the networks remained intact in the absence of the constraints.

Lastly, models were evaluated for how closely the designed structure was recapitulated by "fold-and-dock" symmetric Rosetta™ structure predication calculations: starting from an extended chain, the energy of the assembled oligomer was optimized by Monte Carlo sampling of the internal degrees of freedom of the monomer along with the rigid body transforms relating monomer subunits in the target cyclic symmetry group. Precedence was given to designs with funnel-shaped energy landscapes, in which the ab initio predicted structures converge upon the designed structure, serving as an in silico consistency check, and checking for the possibility that the amino acid sequence can adopt alternate states. Many designs with multiple networks and high polar content at the intermolecular interfaces did not exhibit strong "funneling", although they did exhibit large "energy gaps", meaning that the designed structure was significantly lower in energy that any structure sampled during ab initio "fold-and-dock" calculations. Designs with large energy gaps were also considered for selection for experimental testing.

Designs selected for experimental validation were synthesized with the exact amino acid sequence resulting from the computational design method. The only exception to this was for designs lacking a Tyr or Trp residues, a Tyr was added to the surface at non-interface positions in order to monitor $A_{280}$ for purification and concentration measurements. Additionally, in a few cases, charged surface residues were modified to move the estimated isoelectric point (pI) of the protein away from buffer pH.

Loop Closure

To connect helices of the monomer into a single chain, an exhaustive database of backbone samples composed of fragments spanning two helical regions via a loop of five or less residues, as identified by DSSP, in high resolution crystallographic structures was generated. Candidate loops were identified in this database via rigid alignment of the terminal residues of the fragment and target parametrically designed backbone using an optimized superposition algorithm.

Candidates under a stringent alignment tolerance (within 0.35 Å RMSD) were then fully aligned to the target backbone via torsion-space minimization under stringent coordinate constraints to the target backbone heavy-atom coordinates and soft coordinate constraints to the aligned candidate backbone heavy-atom coordinates. Candidate loop sequences were then designed under sequence profile constraints generated via alignment of the loop backbone to the source structure database, and the lowest-scoring candidate selected as the final loop design.

Structural Analysis

Protein BLAST™ searches were performed using the National Center for Biotechnology Information (NCBI) web server, searching against all non-redundant protein sequences ('nr' database) using an Expect threshold (E-value cutoff) of 10.0 and the BLOSUM62 substitution matrix.

Crystal structures and design models were superimposed through structure-based alignment using all heavy atoms. From this alignment, RMSD was calculated across all alpha-carbon atoms, and also across heavy atoms of the hydrogen bond network residues.

To investigate the structural uniqueness of our designs the MICAN alignment algorithm was used to search against homo-oligomer bio-units of the same symmetry group in the Protein Data Bank (PDB).

To calculate parameters for the crystallized two-ring structures, the Coiled-coil Crick Parameterization (CCCP) web server with the "Global symmetric" optimization option as used, as structures of interest are all symmetric homooligomers. As parameters varied between the inner and outer helices of a given structure, parameters were calculated separately for inner ring and the outer ring helices, inputting .pdb files corresponding to either all helical residues of the inner ring helices, or all helical residues of the outer ring helices, for each crystal structure.

All structural images for figures were generated using PyMOL™.

Experimental Methods

Construction of Synthetic Genes

Synthetic genes were ordered from Genscript Inc. (Piscataway, N.J., USA) and delivered in either pET21-NESG or pET-28b+ *E. coli* expression vectors, inserted at the NdeI and XhoI sites of each vector. For the pET21-NESG constructs, synthesized DNA was cloned in frame with the C-terminal hexahistidine tag. For the pET-28b+ constructs, synthesized DNA was cloned in frame with the N-terminal hexahistidine tag and thrombin cleavage site, and a stop codon was introduced at the C-terminus. Plasmids were transformed into chemically competent *E. coli* BL21(DE3) Star or BL21(DE3)Star-pLysS cells (Invitrogen) for protein expression. Constructs for yeast two-hybrid assays were made by Gibson assembly; inserts were generated by PCR from pET-21 or pET-28 *E. coli* expression vectors as templates, or ordered as gBlocks® (IDT). All primers and gBlocks® were ordered from Integrated DNA Technologies (IDT).

Protein Expression and Purification

Starter cultures were grown at 37° C. in either Luria-Bertani (LB) medium overnight, or in Terrific Broth for 8 hours, in the presence of 50 µg/ml carbenicillin (pET21-NESG) or 30 µg/ml kanamycin (pET-28b+). Starter cultures were used to inoculate 500 mL of LB, Terrific Broth, or Terrific Broth II (MP Biomedicals) containing antibiotic. Cultures were induced with 0.2-0.5 mM IPTG at an OD600 of 0.6-0.9 and expressed overnight at 18° C. (many designs were also later expressed at 37° C. for 4 hours with no noticeable difference in yield). Cells were harvested by centrifugation for 15 minutes at 5000 rcf 4° C. and resuspended in lysis buffer (20 mM Tris, 300 mM NaCl, 20 mM Imidazole, pH 8.0 at room temperature), then lysed by sonication in presence of lysozyme, DNAse, and EDTA-free cocktail protease inhibitor (Roche) or 1 mM PMSF. Lysates were cleared by centrifugation at 4° C. 18,000 rpm for at least 30 minutes and applied to Ni-NTA (Qiagen) columns pre-equilibrated in lysis buffer. The column was washed three times with 5 column volumes (CV) of wash buffer (20 mM Tris, 300 mM NaCl, 30 mM Imidazole, pH 8.0 at room temperature), followed by 3-5 CV of high-salt wash buffer (20 mM Tris, 1 M NaCl, 30 mM Imidazole, pH 8.0 at room temperature), and then 5 CV of wash buffer. Protein was eluted with 20 mM Tris, 300 mM NaCl, 250 mM Imidazole, pH 8.0 at room temperature. Proteins were initially screened by SEC-MALS and CD with His tags intact; if possible, the tags were cleaved and samples were further purified for crystallography, SAXS, and GdmCl melts.

N-terminal hexahistidine tags of the pET-28 constructs were cleaved with restriction grade thrombin (EMD Millipore 69671-3) at room temperature for 4 hours or overnight, using a 1:5000 dilution of enzyme into sample solution; full cleavage was observed after 2 hours via SDS-PAGE analysis and no spurious cleavage was observed at time points upwards of 18 hours. Prior to addition of thrombin, buffer was exchanged into lysis buffer (20 mM Tris, 300 mM NaCl, 20 mM Imidazole). After cleavage, the sample was applied to a column of benzamidine resin (GE Healthcare/Pharmacia, Fisher #45-000-280); resin was resuspended and the sample was incubated on the column for 30-60 minutes with nutation. Flow-through was collected and additional sample was obtained by washing the benzamidine resin with 1.5 CV of lysis buffer. 1 mM PMSF was added to inhibit any remaining free thrombin. Sample was then passed over an additional Ni-NTA column and washed with 1.5 CV of lysis buffer. Proteins were further purified by FPLC size-exclusion chromatography (SEC) using a Superdex 75 10/300 column (GE Healthcare). For SAXS, gel filtration buffer was 20 mM Tris pH 8.0 at room temperature, 150 mM NaCl and 2% glycerol; for crystallography, 20 mM Tris pH 8.0, 100 mM NaCl was used. No reducing agents were added, as none of the designed proteins contained cysteines.

Size-Exclusion Chromatography, Multi-Angle Light Scattering (SEC-MALS)

SEC-MALS experiments used a Superdex 75 10/300 column connected to a miniDAWN TREOS multi-angle static light scattering and an Optilab T-rEX (refractometer with Extended range) detector (Wyatt Technology Corporation, Santa Barbara Calif., USA). Protein samples were injected at concentrations of 3-5 mg/mL in TBS (pH 8.0) or PBS (pH 7.4). Data was analyzed using ASTRA™ (Wyatt Technologies) software to estimate the weigh average molar mass ($M_w$) of eluted species, as well as the number average molar mass ($M_n$) to assess monodispersity by polydispersity index (PDI)=$M_w/M_n$.

Circular Dichroism (CD) Measurements

CD wavelength scans (260 to 195 nm) and temperature melts (25 to 95° C.) were measured using a JASCO J-1500 or an AVIV model 420 CD spectrometer. Temperature melts monitored absorption signal at 222 nm and were carried out at a heating rate of 4° C./min; protein samples were at 0.2-0.5 mg/mL in phosphate buffered saline (PBS) pH 7.4 in a 0.1 cm cuvette.

Guanidinium chloride (GdmCl) titrations were performed on the same spectrometers with automated titration apparatus in PBS pH 7.4 at 25° C., monitored at 222 nm, using a protein concentration of 0.025-0.06 mg/mL in a 1 cm cuvette with stir bar; each titration consisted of at least 40 evenly distributed concentration points with one minute mixing time for each step. Titrant solution consisted of the same concentration of protein in PBS+GdmCl; GdmCl concentration was determined by refractive index.

Inner Helix Peptides

Peptides 2L4HC2_9_inner and 2L6HC3_13_inner were ordered from Genscript Inc. (Piscataway, N.J., USA) with N-terminal acetylation and C-terminal amidation. 2L4HC2_9_inner=SSDYLRETIEELRERIRELEREIRRSN EEIERLREEKS (SEQ ID NO: 93) and 2L6HC3_13_inner=TERENNYRNEENNRKIEEEIREJKK EIKKNKERD (SEQ ID NO: 94). Peptides were dissolved in PBS pH 7.4 and further dialyzed into PBS pH 7.4 for CD experiments.

Crystallization of Protein Samples

Purified protein samples were concentrated to approximately 12 mg/ml in 20 mM Tris pH 8.0 and 100 mM NaCl. Samples were screened using the sparse matrix method (Jancarik and Kim, 1991) with a Phoenix Robot (Art Robbins Instruments, Sunnyvale, Calif.) utilizing the following crystallization screens: Berkeley Screen (Lawrence Berkeley National Laboratory), Crystal Screen, PEG/Ion, Index and PEGRx (Hampton Research, Aliso Viejo, Calif.). The optimum conditions for crystallization of the different designs were found as follows: 2L6HC3_6, 0.2 M Sodium Fluoride, 0.1 M MES pH 5.5 and 20% PEG 400; 2L6HC3_12, 2.2 M Sodium Malonate pH 5.0; 2L6HC3_3, 0.06 M Citric acid, 0.04 M BIS-TRIS propane pH 4.1 and 16% PEG 3,350; 2L8HC4_0.12, 0.2 M Sodium Acetate trihydrate, 0.1 M Tris hydrochloride pH 8.5 and 30% PEG 4,000; 3L6HC2_2, 0.1 M Sodium Acetate trihydrate pH 4.5 and 3.0 M Sodium chloride; 2L4HC2_23, 0.2 M Lithium chloride and 20% PEG 3,350; 2L4HC2_9, 0.1 M Sodium citrate tribasic dehydrate pH 5.0, 30% PEG MME 550; 2L4HC2_11, 0.1 M Tris pH 8.5 and 2.0 M Ammonium sulfate; 5L6HC3_1, 0.1 M Citric acid pH 3.5 and 3.0 M Sodium chloride; and 2L4HC2_24 was concentrated to 20 mg/ml and crystallized in 0.1 M Citric acid pH 3.5, 2.0 M Ammonium sulfate. Crystals were obtained after 1 to 14 days by the sitting-drop vapor-diffusion method with the drops consisting of a 1:1 mixture of 0.2 µL protein solution and 0.2 µL reservoir solution.

X-Ray Data Collection and Structure Determination

The crystals of the designed proteins were placed in a reservoir solution containing 15 to 20% (v/v) glycerol, and then flash-cooled in liquid nitrogen. The X-ray data sets were collected at the Berkeley Center for Structural Biology beamlines 5.0.1, 8.2.1 and 8.2.2 of the Advanced Light Source at Lawrence Berkeley National Laboratory (LBNL). Data sets were indexed and scaled using HKL2000. All the design structures were determined by the molecular-replacement method with the program PHASER within the Phenix suite using the design models as the initial search model. The atomic positions obtained from molecular replacement and the resulting electron density maps were used to build the design structures and initiate crystallographic refinement and model rebuilding. Structure refinement was performed using the phenix.refine program. Manual rebuilding using COOT and the addition of water molecules allowed construction of the final models. Root-mean-square deviation differences from ideal geometries for bond lengths, angles and dihedrals were calculated with Phenix. The overall stereochemical quality of all final models was assessed using the program MOLPROBIY.

Small Angle X-Ray Scattering (SAXS)

Samples were purified by gel filtration in 20 mM Tris pH 8.0 at room temperature, 150 mM NaCl and 2% glycerol; fractions preceding the void volume of the column were used as blanks for buffer subtraction. Scattering measurements were performed at the SIBYLS 12.3.1 beamline at the Advanced Light Source. The X-ray wavelength ($\lambda$) was 1 Å, and the sample-to-detector distance of the Mar16S detector was 1.5 m, corresponding to a scattering vector q (q=4$\pi$ sin $\theta$/1, where 2$\theta$ is the scattering angle) range of 0.01 to 0.3 Å-1. Data sets were collected using exposures of 0.5, 1, and 6 seconds at 12 keV. For longer exposures that resulted in saturation of low q signal or radiation damage, datasets were merged with lower exposures from the same sample. For each sample, data was collected for at least two different concentrations to test for concentration-dependent effects; "high" concentration samples ranged from 3-7 mg/ml and "low" concentration samples ranged from 1-2 mg/ml. Data was analyzed using the ScÅtter software package as previously described; for samples that did not exhibit concentration-dependence, the best data set based on signal-to-noise and Guinier fitting was used for analysis. FoXS was used to compare design models to experimental scattering profiles and calculate quality of fit (X) values. For the design models, extra residues introduced by the expression vector were added to the computational models using Rosetta™ Remodel so that the design sequence matched that of the experimental sample. To capture the conformational flexibility of these extra tag residues in solution, 100 independent models were generated per design. These 100 models were then clustered by Rosetta™, and to avoid bias, the cluster center of the largest cluster was selected as the single representative model used for fitting to experimental data.

Yeast Two-Hybrid

Protein binders were cloned into plasmids bearing the GAL4 DNA-binding domain (pOBD2) and or the GAL4 transcription activation domain (poAD) using Gibson assembly and sequence verified. For each pair of binders tested, the yeast strain PJ69-4a was transformed with the appropriate pair of plasmids using a modified LiOAc transformation protocol where rescue and selection of the transformed yeast was performed in minimal liquid media lacking tryptophan and leucine. Before the assay, transformed cells were diluted 1:10 and grown for 16 hours in fresh minimal media lacking tryptophan and leucine. After this initial incubation, cells were diluted again 1:10 and grown—while shaking—in a 96 well plate, this time in 200 µl of minimal media lacking tryptophan, leucine and histidine. Since a protein interaction between the DNA-binding domain and the transcription activation domain is necessary for the cells to grow in the absence of histidine, successful interactions can be approximated by growth rate. The optical density (OD) of cells was measured every 10 minutes over the span of 48 hours, and the growth rate was calculated for every 60-minute span. The maximum growth rate per hour (maxV) was used as a proxy for interactions between binder pairs.

Mass Spectrometry

Gel bands were isolated, washed with ammonium bicarbonate, and reduced with DTT at 60° C. for 15 minutes. After cooling, gel pieces were treated with iodoacetamide for 15 minutes, in the dark at room temperature, to alkylate reduced thiol groups. Protease digestion was accomplished with sequencing grade trypsin at 10:1, substrate to enzyme, concentration for 4 hours at 37° C. Peptide samples were dried under vacuum and resuspended in 0.1% formic acid prior to LCMS/MS analysis. Liquid chromatography consisted of a 60-minute gradient across a 15 cm column packed with C18 resin downstream of a 3 cm kasil frit trap packed with C12 resin. Spectra were collected using data-dependent acquisition on a Thermo Velos Pro mass spectrometer. Each sample was injected with three technical replicates and peptides were identified using SEQUEST and Percolator followed by IDPicker for protein inference.

In a further aspect, a method is provided. A computing device determines a search space for hydrogen bond networks related to one or more molecules. The search space includes a plurality of energy terms related to a plurality of residues related to the hydrogen bond networks. The computing device searches the search space to identify one or more hydrogen bond networks based on the plurality of energy terms. The computing device screens the identified one or more hydrogen bond networks to identify one or more screened hydrogen bond networks based on scores for the one or more identified hydrogen bond networks. The computing device generates an output related to the one or more screened hydrogen bond networks.

In another aspect, a computing device is provided. The computing device includes one or more data processors and a computer-readable medium. The computer-readable medium is configured to store at least computer-readable instructions that, when executed, cause the computing device to perform functions. The functions include: determining a search space for hydrogen bond networks related to one or more molecules, where the search space includes a plurality of energy terms related to a plurality of residues related to the hydrogen bond networks; searching the search space to identify one or more hydrogen bond networks based on the plurality of energy terms; screening the identified one or more hydrogen bond networks to identify one or more screened hydrogen bond networks based on scores for the one or more identified hydrogen bond networks; and generating an output related to the one or more screened hydrogen bond networks.

In another aspect, a computer-readable medium is provided. The computer-readable medium is configured to store at least computer-readable instructions that, when executed by one or more processors of a computing device, cause the computing device to perform functions. The functions include: determining a search space for hydrogen bond networks related to one or more molecules, where the search space includes a plurality of energy terms related to a plurality of residues related to the hydrogen bond networks; searching the search space to identify one or more hydrogen bond networks based on the plurality of energy terms; screening the identified one or more hydrogen bond networks to identify one or more screened hydrogen bond networks based on scores for the one or more identified hydrogen bond networks; and generating an output related to the one or more screened hydrogen bond networks.

In another aspect, an apparatus is provided. The apparatus includes: means for determining a search space for hydrogen bond networks related to one or more molecules, where the search space includes a plurality of energy terms related to a plurality of residues related to the hydrogen bond networks; means for searching the search space to identify one or more hydrogen bond networks based on the plurality of energy terms; means for screening the identified one or more hydrogen bond networks to identify one or more screened hydrogen bond networks based on scores for the one or more identified hydrogen bond networks; and means for generating an output related to the one or more screened hydrogen bond networks.

Example Computing Environment

FIG. 6 is a block diagram of an example computing network. Some or all of the above-mentioned techniques disclosed herein, such as but not limited to techniques disclosed as part of and/or being performed by software, the Rosetta™ software suite, RosettaDesign™, Rosetta™ applications, and/or other herein-described computer software and computer hardware, can be part of and/or performed by a computing device. For example, FIG. 6 shows protein design system 602 configured to communicate, via network 606, with client devices 604a, 604b, and 604c and protein database 608. In some embodiments, protein design system 602 and/or protein database 608 can be a computing device configured to perform some or all of the herein described methods and techniques, such as but not limited to, method 800 and functionality described as being part of or related to Rosetta™. Protein database 608 can, in some embodiments, store information related to and/or used by Rosetta™.

Network 606 may correspond to a LAN, a wide area network (WAN), a corporate intranet, the public Internet, or any other type of network configured to provide a communications path between networked computing devices. Network 606 may also correspond to a combination of one or more LANs, WANs, corporate intranets, and/or the public Internet.

Although FIG. 6 only shows three client devices 604a, 604b, 604c, distributed application architectures may serve tens, hundreds, or thousands of client devices. Moreover, client devices 604a, 604b, 604c (or any additional client devices) may be any sort of computing device, such as an ordinary laptop computer, desktop computer, network terminal, wireless communication device (e.g., a cell phone or smart phone), and so on. In some embodiments, client devices 604a, 604b, 604c can be dedicated to problem solving/using the Rosetta™ software suite. In other embodiments, client devices 604a, 604b, 604c can be used as general purpose computers that are configured to perform a number of tasks and need not be dedicated to problem solving/using Rosetta™. In still other embodiments, part or all of the functionality of protein design system 602 and/or protein database 608 can be incorporated in a client device, such as client device 604a, 604b, and/or 604c.

Computing Environment Architecture

FIG. 7A is a block diagram of an example computing device (e.g., system). In particular, computing device 700 shown in FIG. 7A can be configured to: include components of and/or perform one or more functions of protein design system 602, client device 604a, 604b, 604c, network 606, and/or protein database 608 and/or carry out part or all of any herein-described methods and techniques, such as but not limited to method 800. Computing device 700 may include a user interface module 701, a network-communication interface module 702, one or more processors 703, and data storage 704, all of which may be linked together via a system bus, network, or other connection mechanism 705.

User interface module 701 can be operable to send data to and/or receive data from external user input/output devices. For example, user interface module 701 can be configured to send and/or receive data to and/or from user input devices such as a keyboard, a keypad, a touch screen, a computer mouse, a track ball, a joystick, a camera, a voice recognition module, and/or other similar devices. User interface module 701 can also be configured to provide output to user display devices, such as one or more cathode ray tubes (CRT), liquid crystal displays (LCD), light emitting diodes (LEDs), displays using digital light processing (DLP) technology, printers, light bulbs, and/or other similar devices, either now known or later developed. User interface module 701 can also be configured to generate audible output(s), such as a speaker, speaker jack, audio output port, audio output device, earphones, and/or other similar devices.

Network-communications interface module 702 can include one or more wireless interfaces 707 and/or one or more wireline interfaces 708 that are configurable to communicate via a network, such as network 606 shown in FIG. 6. Wireless interfaces 707 can include one or more wireless transmitters, receivers, and/or transceivers, such as a Bluetooth transceiver, a Zigbee transceiver, a Wi-Fi transceiver, a WiMAX transceiver, and/or other similar type of wireless transceiver configurable to communicate via a wireless network. Wireline interfaces 708 can include one or more wireline transmitters, receivers, and/or transceivers, such as an Ethernet transceiver, a Universal Serial Bus (USB) transceiver, or similar transceiver configurable to communicate via a twisted pair, one or to more wires, a coaxial cable, a fiber-optic link, or a similar physical connection to a wireline network.

In some embodiments, network communications interface module 702 can be configured to provide reliable, secured, and/or authenticated communications. For each communication described herein, information for ensuring reliable communications (i.e., guaranteed message delivery) can be provided, perhaps as part of a message header and/or footer (e.g., packet/message sequencing information, encapsulation header(s) and/or footer(s), size/time information, and transmission verification information such as CRC and/or parity check values). Communications can be made secure (e.g., be encoded or encrypted) and/or decrypted/decoded using one or more cryptographic protocols and/or algorithms, such as, but not limited to, DES, AES, RSA, Diffie-Hellman, and/or DSA. Other cryptographic protocols and/or algorithms can be used as well or in addition to those listed herein to secure (and then decrypt/decode) communications.

Processors 703 can include one or more general purpose processors and/or one or more special purpose processors (e.g., digital signal processors, application specific integrated circuits, etc.). Processors 703 can be configured to execute computer-readable program instructions 706 contained in data storage 704 and/or other instructions as described herein. Data storage 704 can include one or more computer-readable storage media that can be read and/or accessed by at least one of processors 703. The one or more computer-readable storage media can include volatile and/or non-volatile storage components, such as optical, magnetic, organic or other memory or disc storage, which can be integrated in whole or in part with at least one of processors 703. In some embodiments, data storage 704 can be implemented using a single physical device (e.g., one optical, magnetic, organic or other memory or disc storage unit), while in other embodiments, data storage 704 can be implemented using two or more physical devices.

Data storage 704 can include computer-readable program instructions 706 and perhaps additional data. For example, in some embodiments, data storage 704 can store part or all of data utilized by a protein design system and/or a protein database; e.g., protein designs system 602, protein database 608. In some embodiments, data storage 704 can additionally include storage required to perform at least part of the herein-described methods and techniques and/or at least part of the functionality of the herein-described devices and networks.

FIG. 7B depicts a network 606 of computing clusters 709a, 709b, 709c arranged as a cloud-based server system in accordance with an example embodiment. Data and/or software for protein design system 602 can be stored on one or more cloud-based devices that store program logic and/or data of cloud-based applications and/or services. In some embodiments, protein design system 602 can be a single computing device residing in a single computing center. In other embodiments, protein design system 602 can include multiple computing devices in a single computing center, or even multiple computing devices located in multiple computing centers located in diverse geographic locations.

In some embodiments, data and/or software for protein design system 602 can be encoded as computer readable information stored in tangible computer readable media (or computer readable storage media) and accessible by client devices 604a, 604b, and 604c, and/or other computing devices. In some embodiments, data and/or software for protein design system 602 can be stored on a single disk drive or other tangible storage media, or can be implemented on multiple disk drives or other tangible storage media located at one or more diverse geographic locations.

FIG. 7B depicts a cloud-based server system in accordance with an example embodiment. In FIG. 7B, the functions of protein design system 602 can be distributed among three computing clusters 709a, 709b, and 709c. Computing cluster 709a can include one or more computing devices 700a, cluster storage arrays 710a, and cluster routers 711a connected by a local cluster network 712a. Similarly, computing cluster 709b can include one or more computing devices 700b, cluster storage arrays 710b, and cluster routers 711b connected by a local cluster network 712b. Likewise, computing cluster 709c can include one or more computing devices 700c, cluster storage arrays 710c, and cluster routers 711c connected by a local cluster network 712c.

In some embodiments, each of the computing clusters 709a, 709b, and 709c can have an equal number of computing devices, an equal number of cluster storage arrays, and an equal number of cluster routers. In other embodiments, however, each computing cluster can have different numbers of computing devices, different numbers of cluster storage arrays, and different numbers of cluster routers. The number of computing devices, cluster storage arrays, and cluster routers in each computing cluster can depend on the computing task or tasks assigned to each computing cluster.

In computing cluster 709a, for example, computing devices 700a can be configured to perform various computing tasks of protein design system 602. In one embodiment, the various functionalities of protein design system 602 can be distributed among one or more of computing devices 700a, 700b, and 700c. Computing devices 700b and 700c in computing clusters 709b and 709c can be configured similarly to computing devices 700a in computing cluster 709a. On the other hand, in some embodiments, computing devices 700a, 700b, and 700c can be configured to perform different functions.

In some embodiments, computing tasks and stored data associated with protein design system 602 can be distributed across computing devices 700a, 700b, and 700c based at least in part on the processing requirements of protein design system 602, the processing capabilities of computing devices 700a, 700b, and 700c, the latency of the network links between the computing devices in each computing cluster and between the computing clusters themselves, and/or other factors that can contribute to the cost, speed, fault-tolerance, resiliency, efficiency, and/or other design goals of the overall system architecture.

The cluster storage arrays 710a, 710b, and 710c of the computing clusters 709a, 709b, and 709c can be data storage arrays that include disk array controllers configured to manage read and write access to groups of hard disk drives. The disk array controllers, alone or in conjunction with their respective computing devices, can also be configured to manage backup or redundant copies of the data stored in the cluster storage arrays to protect against disk drive or other cluster storage array failures and/or network failures that prevent one or more computing devices from accessing one or more cluster storage arrays.

Similar to the manner in which the functions of protein design system 602 can be distributed across computing devices 700a, 700b, and 700c of computing clusters 709a, 709b, and 709c, various active portions and/or backup portions of these components can be distributed across cluster storage arrays 710a, 710b, and 710c. For example, some cluster storage arrays can be configured to store one portion of the data and/or software of protein design system 602, while other cluster storage arrays can store a separate portion of the data and/or software of protein design system 602. Additionally, some cluster storage arrays can be configured to store backup versions of data stored in other cluster storage arrays.

The cluster routers 711a, 711b, and 711c in computing clusters 709a, 709b, and 709c can include networking equipment configured to provide internal and external communications for the computing clusters. For example, the cluster routers 711a in computing cluster 709a can include one or more internet switching and routing devices configured to provide (i) local area network communications between the computing devices 700a and the cluster storage arrays 701a via the local cluster network 712a, and (ii) wide area network communications between the computing cluster 709a and the computing clusters 709b and 709c via the wide area network connection 713a to network 606. Cluster routers 711b and 711c can include network equipment similar to the cluster routers 711a, and cluster routers 711b and 711c can perform similar networking functions for computing clusters 709b and 709b that cluster routers 711a perform for computing cluster 709a.

In some embodiments, the configuration of the cluster routers 711a, 711b, and 711c can be based at least in part on the data communication requirements of the computing devices and cluster storage arrays, the data communications capabilities of the network equipment in the cluster routers 711a, 711b, and 711c, the latency and throughput of local networks 712a, 712b, 712c, the latency, throughput, and cost of wide area network links 713a, 713b, and 713c, and/or other factors that can contribute to the cost, speed, fault-tolerance, resiliency, efficiency and/or other design goals of the moderation system architecture.

Example Methods of Operation

FIG. 8 is a flow chart of an example method 800. Method 800 can be carried out by a computing device, such as computing device 700 described in the context of at least FIG. 7A Method 800 can begin at block 810, where the computing device can determine a search space for hydrogen bond networks related to one or more molecules, where the search space includes a plurality of energy terms related to a plurality of residues related to the hydrogen bond networks, such as discussed above at least in the "Computational Techniques" section.

In some embodiments, the search space can be configured as a graph having a plurality of nodes connected by one or more edges, where a node of the plurality of nodes is based on a particular residue of the plurality of residues, the particular residue having a residue position, and where an edge of the one or more edges connects a first node and a second node of the plurality of nodes based on a possible interaction between the first and second nodes, such as discussed above at least in the "Computational Techniques" section. In particular of these embodiments, the first node can relate to a first residue of the plurality of residues, where the second node relates to a second residue of the plurality of residues, and where the possible interaction between first and second nodes relate to a possible interaction between a rotamer of the first residue and/or a rotamer of the second residue, such as discussed above at least in the "Computational Techniques" section. In more particular of these embodiments, the possible interaction between the possible interaction between first and second nodes can relate to an interaction energy between the first residue and the second residue, such as discussed above at least in the "Computational Techniques" section. In even more particular of these embodiments, determining the search space can include: determining whether the interaction energy between the first residue and the second residue is less than a threshold interaction energy; and after determining that the interaction energy between the first residue and the second residue is less than the threshold interaction energy, adding a hydrogen bond network including the first node, the second node, and at least one edge between the first and second nodes to the search space, such as discussed above at least in the "Computational Techniques" section. In further more particular of these embodiments, at least one edge between the first and second nodes can include information about the interaction energy between the first residue and the second residue, such as discussed above at least in the "Computational Techniques" section. In even further particular of these embodiments, the information about the interaction energy between the first residue and the second residue can include a plurality of interaction energy values, where each interaction energy value in the plurality of interaction energy values is associated with a particular rotamer of the first residue and a particular rotamer of the second residue, such as discussed above at least in the "Computational Techniques" section.

In other embodiments, determining the search space can include: determining at least a first residue position and a second residue position at an intermolecular interface between a first molecule and a second molecule, the first residue position associated with a first residue of the first molecule and the second residue position associated with a second residue of the second molecule; and determining the search space based on the at least the first residue position and the second residue position, such as discussed above at least in the "Computational Techniques" section. In some of these embodiments, at least one of the first molecule and the second molecule can include a polypeptide chain, such as discussed above at least in the "Computational Techniques" section.

At block 820, the computing device can search the search space to identify one or more hydrogen bond networks based on the plurality of energy terms, such as discussed above at least in the "Computational Techniques" section. In some embodiments, searching the search space includes searching all of the search space, such as discussed above at least in the "Computational Techniques" section. In particular of these embodiments, searching all of the search space using the depth-first search. In other particular of these embodiments, searching all of the search space includes searching all of the search space using a breadth-first search, such as discussed above at least in the "Computational Techniques" section.

In other embodiments, searching the search space can include: performing a first search of the search space to identify one or more initial hydrogen bond networks; and identifying the one or more identified hydrogen bond networks by at least merging a first hydrogen bond network and a second hydrogen bond network of the one or more initial hydrogen bond networks, such as discussed above at least in the "Computational Techniques" section. In particular of these embodiments, merging the first hydrogen bond network and the second hydrogen bond network can include: determining whether the first hydrogen bond network and the second hydrogen bond network share an identical rotamer; and after determining that the first hydrogen bond network and the second hydrogen bond network share an identical rotamer, merging the first hydrogen bond network and the second hydrogen bond network, such as discussed above at least in the "Computational Techniques" section.

At block 830, the computing device can screening the identified one or more hydrogen bond networks to identify one or more screened hydrogen bond networks based on scores for the one or more identified hydrogen bond networks, such as discussed above at least in the "Computational Techniques" section. In some embodiments, a particular score for a particular identified hydrogen bond network of the one or more identified hydrogen bond networks can be based on a number of polar atoms that participate in the particular hydrogen bond network, such as discussed above at least in the "Computational Techniques" section. In other embodiments, a particular score for a particular identified hydrogen bond network of the one or more identified hydrogen bond networks can be based on a background reference structure, such as discussed above at least in the "Computational Techniques" section. In particular of these embodiments, the particular score for the particular identified hydrogen bond network can be based on a score related to one or more sidechain-backbone hydrogen bonds, where the one or more sidechain-backbone hydrogen bonds can be related to the background reference structure, such as discussed above at least in the "Computational Techniques" section. In still other embodiments, a particular score for a particular identified hydrogen bond network of the one or more identified hydrogen bond networks can be based on an energy function, such as discussed above at least in the "Computational Techniques" section.

At block 840, an output related to the one or more screened hydrogen bond networks can be generated. In some embodiments, generating the output related to the one or more screened hydrogen bond networks can include designing one or more molecules based on the screened hydrogen bond networks, such as discussed above at least in the "Computational Techniques" section. In particular of these embodiments, designing the one or more molecules based on the screened hydrogen bond networks includes allowing one or more relatively-small movements of one or more rotamers in a screened hydrogen bond network, such as discussed above at least in the "Computational Techniques" section.

In other embodiments, generating the output related to the one or more screened to hydrogen bond networks can include generating a plurality of outputs related to the one or more screened hydrogen bond networks, such as discussed above at least in the "Computational Techniques" section. In still other embodiments, generating the output related to the one or more screened hydrogen bond networks can include:

generating a synthetic gene that is based on the one or more screened hydrogen bond networks; expressing a particular protein in vivo using the synthetic gene; and purifying the particular protein. In particular of these embodiments, expressing the particular protein sequence in vivo using the synthetic gene includes expressing the particular protein sequence in one or more *Escherichia coli* that include the synthetic gene, such as discussed above in at least in the "Experimental Methods" section.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

The above definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, $3^{rd}$ Edition or a dictionary known to those of skill in the art, such as the Oxford Dictionary of Biochemistry and Molecular Biology (Ed. Anthony Smith, Oxford University Press, Oxford, 2004).

As used herein and unless otherwise indicated, the terms "a" and "an" are taken to mean "one", "at least one" or "one or more". Unless otherwise required by context, singular terms used herein shall include pluralities and plural terms shall include the singular.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural or singular number, respectively. Additionally, the words "herein," "above" and "below" and words of similar import, when used in this application, shall refer to this application as a whole and not to any particular portions of this application.

The above description provides specific details for a thorough understanding of, and enabling description for, embodiments of the disclosure. However, one skilled in the art will understand that the disclosure may be practiced without these details. In other instances, well-known structures and functions have not been shown or described in detail to avoid unnecessarily obscuring the description of the embodiments of the disclosure. The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize.

All of the references cited herein are incorporated by reference. Aspects of the disclosure can be modified, if necessary, to employ the systems, functions and concepts of the above references and application to provide yet further embodiments of the disclosure. These and other changes can be made to the disclosure in light of the detailed description.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The above detailed description describes various features and functions of the disclosed systems, devices, and methods with reference to the accompanying figures. In the figures, similar symbols typically identify similar components, unless context dictates otherwise. The illustrative embodiments described in the detailed description, figures, and claims are not meant to be limiting. Other embodiments can be utilized, and other changes can be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

With respect to any or all of the ladder diagrams, scenarios, and flow charts in the figures and as discussed herein, each block and/or communication may represent a processing of information and/or a transmission of information in accordance with example embodiments. Alternative embodiments are included within the scope of these example embodiments. In these alternative embodiments, for example, functions described as blocks, transmissions, communications, requests, responses, and/or messages may be executed out of order from that shown or discussed, including substantially concurrent or in reverse order, depending on the functionality involved. Further, more or fewer blocks and/or functions may be used with any of the ladder diagrams, scenarios, and flow charts discussed herein, and these ladder diagrams, scenarios, and flow charts may be combined with one another, in part or in whole.

A block that represents a processing of information may correspond to circuitry that can be configured to perform the specific logical functions of a herein-described method or technique. Alternatively or additionally, a block that represents a processing of information may correspond to a module, a segment, or a portion of program code (including related data). The program code may include one or more instructions executable by a processor for implementing specific logical functions or actions in the method or technique. The program code and/or related data may be stored on any type of computer readable medium such as a storage device including a disk or hard drive or other storage medium.

The computer readable medium may also include non-transitory computer readable media such as computer-readable media that stores data for short periods of time like register memory, processor cache, and random access memory (RAM). The computer readable media may also include non-transitory computer readable media that stores program code and/or data for longer periods of time, such as secondary or persistent long term storage, like read only memory (ROM), optical or magnetic disks, compact-disc read only memory (CD-ROM), for example. The computer readable media may also be any other volatile or non-volatile storage systems. A computer readable medium may be considered a computer readable storage medium, for example, or a tangible storage device. Moreover, a block that represents one or more information transmissions may correspond to information transmissions between software and/or hardware modules in the same physical device. However, other information transmissions may be between software modules and/or hardware modules in different physical devices.

Numerous modifications and variations of the present disclosure are possible in light of the above teachings.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

We claim:

1. A polypeptide comprising the amino acid sequence of Formula I:

Z1-Z2-Z3-Z4-Z5, wherein:

Z1 is a helix initiating sequence comprising the amino acid sequence of Formula 2: J1-J2-J3, wherein
  J1 is selected from the group consisting of S, T, N, and D;
  J2 is selected from the group consisting of P, E, R, K, L, A; and
  J3 is selected from the group consisting of E, D, R, K, L, V, A, S, T, Y, or is absent;

Z3 is a helix connecting sequence having the amino acid sequence of Formula 3:

(SEQ ID NO: 1)
[RKED]-L-[NQEDRKST]-[NQEDRKST]-[NQEDRKST]-G-
[STNQED]-[STNQED]-[STND]-E-[EDRK]-V-[RKED];

Z5 is a helix terminating sequence comprising the amino acid sequence of Formula 4:

xx-xx-[RKEDSTNQYA];

Z2 is selected from the group consisting of general formulae $BX_1BX_2$, $X_1BBX_2$, $X_1BX_2B$, $X_1X_2BB$, $BX_1X_2B$, and $BBX_1X_2$, wherein:
  B is xx-S-L-xx-xx-Q-xx;
  $X_1$ and $X_2$ independently have the amino acid sequence of Formula 5:

$O_1O_2O_3O_4O_5O_6O_7$ wherein:

$O_1$, $O_4$, $O_5$, and $O_7$ are xx;
  $O_2$ and $O_3$ are independently selected from the group consisting of I, L, and A; and
  $O_6$ is L; and Z4 is selected from the group consisting of general formulae $B_2X_3B_2X_4$, $X_3B_2B_2X_4$, $X_3B_2X_4B_2$, $X_3X_4B_2B_2$, $B_2X_3X_4B_2$, and $B_2B_2X_3X_4$, wherein
  $B_2$ is xx-L-A-xx-xx-Q-xx; and
  $X_3$ and $X_4$ independently have the amino acid sequence of Formula 6:

$O_{10}O_{11}O_{12}O_{13}O_{14}O_{15}O_{16}$ wherein $O_{10}$, $O_{13}$, $O_{14}$, and $O_{16}$ are xx;
  $O_{11}$ is L; and
  $O_{12}$ and $O_{15}$ are independently selected from e group consisting of I, L, V, and A;

wherein xx is any amino acid; and
wherein:
  (i) when Z2 is $BX_1BX_2$ then Z4 is $X_3B_2X_4B_2$;
  (ii) when Z2 is $X_1BBX_2$ then Z4 is $X_3B_2B_2X_4$;
  (iii) when Z2 is $X_1BX_2B$ then Z4 is $BX_3B_2X_4$;
  (iv) when Z2 is $X_1X_2BB$ then Z4 is $B_2B_2X_3X_4$;
  (v) when Z2 is $BX_1X_2B$ then Z4 is $B_2X_3X_4B_2$;
  (vi) when Z2 is $BBX_1X_2$ then Z4 is $X_3X_4B_2B_2$; and
  (vii) "and" is not used interchangeably with "or".

2. The polypeptide of claim 1, wherein J3 is present.

3. The polypeptide of claim 1, wherein Z1 is TRT.

4. The polypeptide of claim 1, wherein Z3 is RLQREGSSDEDVR (SEQ ID NO: 81).

5. The polypeptide of claim 1, wherein Z5 is RQD.

6. The polypeptide of claim 1, wherein B is RSLREQE (SEQ ID NO: 82).

7. The polypeptide of claim 1, wherein $O_1$, $O_4$, $O_5$, and $O_7$ are independently selected from the group consisting of E, R, and K; wherein "and" is not used interchangeably with "or".

8. The polypeptide of claim 1, wherein $X_1$ and $X_2$ are independently selected from the group consisting of EIIRELE (SEQ ID NO: 83), ELLRELE (SEQ ID NO: 84), and ELAKRLK (SEQ ID NO: 85); wherein "and" is not used interchangeably with "or".

9. The polypeptide of claim 1, wherein $B_2$ is KLAREQK (SEQ ID NO: 86).

10. The polypeptide of claim 1, wherein $O_{12}$ and $O_{15}$ are independently selected from the group consisting of I, L, and V; wherein "and" is not used interchangeably with "or".

11. The polypeptide of claim 1, wherein $X_3$ and $X_4$ are independently selected from the group consisting of [YE]-LVEELK (SEQ ID NO: 87), [YE]-LLREIK (SEQ ID NO: 88), [YE]-LVEEIE (SEQ ID NO: 89), ELVEELK (SEQ ID NO: 90), ELLREIK (SEQ ID NO: 91), and ELVEEIE (SEQ ID NO: 92); wherein "and" is not used interchangeably with "or".

12. The polypeptide of claim 1, wherein Z2 is selected from the group consisting of general formulae $BX_1BX_2$, $X_1BBX_2$, $X_1BX_2B$, and $X_1X_2BB$; and Z4 is selected from the group consisting of general formulae $B_2X_3B_2X_4$, $X_3B_2B_2X_4$, $X_3B_2X_4B_2$, and $X_3X_4B_2B_2$; wherein "and" is not used interchangeably with "or".

13. The polypeptide of claim 1, comprising a polypeptide that is at least 75% identical over its full length to the amino acid sequence selected from the group consisting of SEQ ID NOS:2-5.

14. The polypeptide of claim 1, linked to a cargo.

15. The polypeptide of claim 1, comprising a homo-oligomer of the polypeptide.

16. A polypeptide that is at least 75% identical over its full length to the amino acid sequence selected from the group consisting of SEQ ID NOS:2-79.

17. The polypeptide of claim 16, which is at least 90% identical over its full length to the amino acid sequence selected from the group consisting of SEQ ID NOS:2-79.

18. The polypeptide of claim 16, which is at least 95% identical over its full length to the amino acid sequence selected from the group consisting of SEQ H) NOS:2-79.

19. The polypeptide of claim 16, which is at least 100% identical over its full length to the amino acid sequence selected from the group consisting of SEQ ID NOS:2-79.

20. A polypeptide that is at least 75% identical over its full length to the amino add sequence of SEQ ID NO: 24.

21. The polypeptide of claim 20, wherein the polypeptide comprises the amino acid sequence of SEQ ID NO:24.

* * * * *